US012577219B2

(12) United States Patent
Shao et al.

(10) Patent No.: US 12,577,219 B2
(45) Date of Patent: Mar. 17, 2026

(54) MACROLIDE BREFELDIN A ESTER DERIVATIVES AND USE THEREOF

(71) Applicant: OCEAN UNIVERSITY OF CHINA, Qingdao (CN)

(72) Inventors: Changlun Shao, Qingdao (CN); Yaoyao Jiang, Qingdao (CN); Ming Liu, Qingdao (CN); Changyun Wang, Qingdao (CN); Meiyan Wei, Qingdao (CN); Cuifang Wang, Qingdao (CN)

(73) Assignee: OCEAN UNIVERSITY OF CHINA, Qingdao (CN)

( * ) Notice: Subject to any disclaimer, the term of this patent is extended or adjusted under 35 U.S.C. 154(b) by 1089 days.

(21) Appl. No.: 17/523,459

(22) Filed: Nov. 10, 2021

(65) Prior Publication Data

US 2022/0064138 A1 Mar. 3, 2022

Related U.S. Application Data

(63) Continuation-in-part of application No. PCT/CN2020/137696, filed on Dec. 18, 2020.

(30) Foreign Application Priority Data

Nov. 28, 2019 (CN) ........................ 201911188758.1
Nov. 24, 2020 (CN) ........................ 202011327700.3

(51) Int. Cl.
*C07D 313/00* (2006.01)
*A61P 35/00* (2006.01)

(52) U.S. Cl.
CPC ............ *C07D 313/00* (2013.01); *A61P 35/00* (2018.01)

(58) Field of Classification Search
CPC .. C07D 313/00; C07D 405/12; C07D 405/14; C07D 407/12; C07D 407/14
See application file for complete search history.

(56) References Cited

U.S. PATENT DOCUMENTS

| | | | |
|---|---|---|---|
| 4,328,245 A | 5/1982 | Yu et al. | |
| 4,409,239 A | 10/1983 | Yu | |
| 4,410,545 A | 10/1983 | Yu et al. | |
| 6,350,458 B1 | 2/2002 | Modi | |

FOREIGN PATENT DOCUMENTS

| | | | | |
|---|---|---|---|---|
| CN | 102731573 A | 10/2012 | | |
| CN | 103788053 A * | 5/2014 | ........... C07D 313/00 | |
| CN | 105153136 A | 12/2015 | | |
| CN | 110028477 A | 7/2019 | | |
| CN | 110028478 A | 7/2019 | | |
| WO | WO-9600726 A2 * | 1/1996 | ........... C07D 313/00 | |
| WO | 96/09299 A1 | 3/1996 | | |
| WO | 98/33498 A1 | 8/1998 | | |

OTHER PUBLICATIONS

Han, H., AAPS Pharmsci., 2000, 2, 1-11 (Year: 2000).*
Purser, S. et al., Chem. Soc. Rev., 2008, 37, 320-330 (Year: 2008).*
Written Opinion of PCT/CN2020/137696, mailed on Mar. 17, 2021, with translation.
He et al., Synthesis and cytotoxic evaluation of acylated brefeldin A derivatives as potential anticancer agents, Chemical Biology & Drug Design, vol. 82, No. 3, (2013) pp. 307-316.
International Search Report in PCT/CN2020/137696, mailed on Mar. 17, 2021.

* cited by examiner

*Primary Examiner* — John S Kenyon
*Assistant Examiner* — Sara Elizabeth Bell
(74) *Attorney, Agent, or Firm* — LEASON ELLIS LLP

(57) ABSTRACT

The ester derivatives of brefeldin A represented by Formula (I) in the inhibition of tumor proliferation. The compounds are prominent in the prevention or treatment of hyperproliferative diseases, including liver cancer, leukemia, breast cancer, colon adenocarcinoma, gastric cancer, lung cancer, Bart's esophageal cancer, cervical cancer, pancreatic cancer, endometrial cancer, bone cancer, lymphoma, kidney cancer, brain cancer, nerve cancer, nasopharyngeal cancer, oral cancer and colorectal cancer, and have the potential to be developed as antitumor agents.

10 Claims, No Drawings

MACROLIDE BREFELDIN A ESTER DERIVATIVES AND USE THEREOF

CROSS-REFERENCE TO RELATED APPLICATIONS

The present application is a continuation-in-part application based on International Patent Application No. PCT/CN2020/137696, which claims priorities to Chinese Patent Application No. 201911188758.1, filed on Nov. 28, 2019 and entitled "Macrolide Brefeldin A Derivatives and Use thereof" as well as Chinese Patent Application No. 202011327700.3, filed on Nov. 24, 2020 and entitled "Macrolide Brefeldin A Derivatives and Use thereof", all of which are incorporated herein by reference in their entireties.

TECHNICAL FIELD

The present disclosure belongs to the field of pharmaceutical technology and specifically relates to a class of brefeldin A ester derivatives, compositions, preparation methods and uses thereof, wherein the compound or composition has the use of inhibiting tumor proliferation activity and can be used to prevent or treat hyperproliferative diseases.

BACKGROUND ART

Brefeldin A (BFA), a kind of macrolide fungal metabolite, was isolated from *Penicillium decumbens* in 1958 by Singleton et al. (Singleton, V. L. et al., *Nature,* 1958, 181, 1072-1073). Its absolute configuration was determined in 1971 by Weber et al. (Weber, H. P. et al., *Helv. Chim. Acta.,* 1971, 54, 2763-2766) by single crystal, CD, and asymmetric synthesis.

BFA is not ideal due to its own pharmacokinetic properties (low bioavailability, poor water solubility, low plasma exposure, short plasma half-life and high toxicity) and cannot be used as a drug in clinical applications. Hitherto, there have been no reports for the BFA derivatives with effectively improved pharmacokinetic properties, increased solubility and/or reduced toxicity.

SUMMARY OF THE DISCLOSURE

The following only summarizes some aspects of the present disclosure, and is not limited there. These aspects and other parts are explained more fully later. All references in this specification are hereby cited in their entirety. When there is a discrepancy between the disclosure content of this specification and the cited documents, the disclosure content of this specification shall prevail.

The present disclosure provides a new class of BFA ester derivatives for the prevention or treatment of hyperproliferative diseases, such as liver cancer, leukemia, breast cancer, colon adenocarcinoma, gastric cancer, lung cancer, Bart's esophageal cancer, cervical cancer, pancreatic cancer, endometrial cancer, bone cancer, lymphoma, kidney cancer, brain cancer, nerve cancer, nasopharyngeal cancer, oral cancer and colorectal cancer. The compounds of the present disclosure have stable properties, high solubility and good safety, which thereby possess a good clinical application prospect.

The present disclosure also provides a pharmaceutical composition comprising said compounds, and methods for using said compounds or compositions to treat the above-mentioned diseases in mammals, especially in humans.

Specifically, in one aspect, the present disclosure relates to an ester derivative of brefeldin A, wherein the ester derivative of brefeldin A is a compound represented by Formula (I), or a stereoisomer, a tautomer, a nitrogen oxide, a solvate, a metabolite or a pharmaceutical acceptable salt of the compound, or a prodrug thereof:

(I)

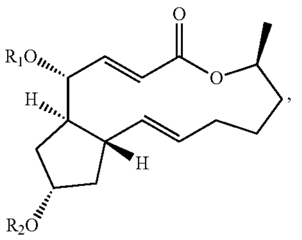

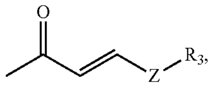

wherein $R_1$ and $R_2$ are each independently H or $R_1$ and $R_2$ are not H simultaneously; Z is selected from the group consisting of benzene ring, pyridine ring, quinoline ring, and isoquinoline ring; $R_3$ is selected from the group consisting of hydrogen, deuterium, halogen, hydroxy, amino, nitro, cyano, carboxyl, alkyl, haloalkyl, alkoxy, alkylamino, alkanoyl, hydroxyalkoxy, hydroxyalkylamino, hydroxyalkanoyl, haloalkoxy, haloalkylamino, haloalkanoyl, aminoalkoxy, cycloalkyl, cycloalkyloxy, cycloalkylamino, cycloalkanoyl, alkenyl, alkenylalkoxy, alkenylalkylamino, alkenylalkanoyl, alkynyl, alkynylalkoxy, alkynylalkylamino, alkynylalkanoyl, aryl, aryloxy, aroyl, arylamino, arylalkoxy, arylalkylamino, heteroaryl, heteroaryloxy, heteroaroyl, heteroarylamino, heteroarylalkoxy, heteroarylalkylamino, heteroarylalkanoyl, heterocycloalkyl, heterocyclyloxy, heterocyclylamino, heterocyclylanoyl, heterocyclylalkoxy, heterocyclylalkylamino, heterocyclylalkanoyl, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylaminoC(=O)—, fused heterobicyclylamino-C(=O)—, fused bicyclyl-C(=O)N($R_4$)—, fused heterobicyclyl-C(=O)N($R_4$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C (═O)—, spiro bicyclyl-C(═O)O—, spiro heterobicyclyl-C(═O)—, spiro heterobicyclyl-C(═O)O—, spiro bicyclylamino-C(═O)—, spiro heterobicyclylamino-C(═O)—, spiro bicyclyl-C(═O)N($R_4$)—, spiro heterobicyclyl-C(═O)N($R_4$)—, $R_5R_4$N—, —C(═O)N$R_4R_5$, —OC(═O)N$R_4R_5$, —OC(═O)O$R_4$, —N($R_4$)C(═O)N$R_4R_5$, —N($R_4$)C(═O)O$R_5$, —N($R_4$)C(═O)—$R_5$, $R_4R_5$N—S(═O)t-, $R_4$S(═O)$_t$—, $R_4$S(═O)$_t$N($R_5$)—, $R_5R_4$N-alkyl, $R_4$S(═O)$_t$-alkyl, $R_4R_5$N—C(═O)-alkyl, $R_5R_4$N- alkoxy, $R_4$S(═O)t-alkoxy, $R_4R_5$N—C(═O)-alkoxy, aryl-(CH$_2$)$_p$-G-(CH$_2$)$_m$—, heteroaryl-(CH$_2$)$_p$-G-(CH$_2$)$_m$—, heterocyclyl-(CH$_2$)$_p$-G-(CH$_2$)$_m$—, and cycloalkyl-(CH$_2$)$_p$-G-(CH$_2$)$_m$—, wherein G is selected from the group consisting of O, S, N$R_6$, S(═O), S(═O)$_2$, C(═O), —C(═O)N($R_4$)—, —OC(═O)N($R_4$)—, —OC(═O)—, —N($R_4$)C(═O)N($R_4$)—, —($R_4$)N—S(═O)t-, —OS(═O)t-, and —OS(═O)tN($R_4$)—, wherein each t is 1 or 2, p and m are each independently 0, 1, 2, 3 or 4, wherein the aryl-(CH$_2$)$_p$-G-(CH$_2$)$_m$—, heteroaryl-(CH$_2$)$_p$-G-(CH$_2$)$_m$—, heterocyclyl-(CH$_2$)$_p$-G-(CH$_2$)$_m$—, or cycloalkyl-(CH$_2$)$_p$-G-(CH$_2$)$_m$— is optionally substituted by one or more substituents selected from the group consisting of F, Cl, Br, I, alkyl, alkenyl, alkynyl, alkoxy and cyano; when Z is a benzene ring, $R_3$ is not H;

$R_6$ is selected from the group consisting of hydrogen, $R_5R_4$NC(═O)—, $R_5$OC(═O)—, $R_5$C(═O)—, $R_5R_4$NS(═O)—, $R_5$OS(═O)—, $R_5$S(═O)—, $R_5R_4$NS(═O)$_2$—, $R_5$OS(═O)$_2$—, $R_5$S(═O)$_2$—, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl and carbocyclyl;

$R_5$ and $R_4$ are each independently selected from the group consisting of hydrogen, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl and cycloalkyl; with the proviso that where $R_5$ and $R_4$ are bonded to a same nitrogen atom, $R_5$ and $R_4$ together with the nitrogen atom optionally form an optionally substituted 3-8 membered ring, an optionally substituted fused bicyclic ring or an optionally substituted spiro bicyclic ring, wherein hetero atoms in the heterocyclyl, heteroaryl, fused heterobicyclyl and/or spiro heterobicyclyl are independently selected from the group consisting of N, O, S, and/or Se, and number of the hetero atoms is 1-5;

wherein $R_3$, $R_4$, $R_5$, $R_6$ are optionally substituted by one or more substituents selected from the group consisting of hydroxyl, hydroxymethyl, carboxyl, acetylamino, alkyl, alkoxy, alkylamino, cycloalkyl, alkenyl, alkynyl, trifluoromethyl, trifluoroacetyl, thiol, halogen, nitro, amino, azido (—N$_3$), guanidyl, cyano, tert-butoxycarbonyl (-Boc), carbonyl (—C═O), oxo (═O), thio (═S), sulfonyl, aryl, heteroaryl, and heterocyclyl.

In some embodiments, $R_3$ is selected from the group consisting of H, D, F, Cl, Br, I, hydroxy, amino, nitro, cyano, C1-C20 alkyl, C1-C20 haloalkyl, C1-C20 alkoxy, C1-C20 alkylamino, C1-C20 alkanoyl, hydroxy-substituted C1-C20 alkoxy, hydroxy-substituted C1-C20 alkylamino, hydroxy-substituted C1-C20 alkanoyl, C1-C20 haloalkoxy, C1-C20 haloalkylamino, C1-C20 haloalkanoyl, C1-C20 aminoalkoxy, C3-C10 cycloalkyl, C3-C10 cycloalkyloxy, C3-C10 cycloalkylamino, C3-C10 cycloalkanoyl, C2-C8 alkenyl, C2-C8 alkynyl, C6-C10 aryl, C6-C10 aryloxy, C6-C10 aroyl, C6-C10 arylamino, C6-C10 aryl-C1-C6 alkoxy, C6-C10 arylalkylamino, C5-C12 heteroaryl, C5-C12 heteroaryloxy, C5-C12 heteroaroyl, C5-C12 heteroarylamino, C5-C12 heteroaryl-C1-C6 alkoxy, C5-C12 heteroaryl-C1-C6 alkylamino, C4-C12 heterocyclyl-C1-C6 alkanoyl, C4-C12 heterocycloalkyl, C4-C12 heterocyclyloxy, C4-C12 heterocyclylamino, C4-C12 heterocyclylanoyl, C4-C12 heterocyclyl-C1-C6 alkoxy, C4-C12 heterocyclyl-C1-C6 alkylamino, C4-C12 heterocyclyl-C1-C6 alkanoyl, $R_5R_4$N—, —C(═O)N$R_4R_5$, —OC(═O)N$R_4R_5$, —OC(═O)O$R_4$, —N($R_4$)C(═O)N$R_4R_5$, —N($R_4$)C(═O)O$R_5$, —N($R_4$)C(═O)—$R_5$, $R_4R_5$N—S(═O)$_t$—, $R_4$S(═O)$_t$—, $R_4$S(═O)$_t$—N$R_5$—, $R_5R_4$N—C1-C6 alkyl, $R_4$S(═O)$_t$—C1-C6 alkyl, $R_4R_5$N—C(═O)$_t$—C1-C6 alkyl, $R_5R_4$N—C1-C6 alkoxy, $R_4$S(═O)$_t$—C1-C6 alkoxy, $R_4R_5$N—C(═O)—C1-C6 alkoxy, C6-C10 aryl-(CH$_2$)$_p$-G-(CH$_2$)$_m$—, C5-C12 heteroaryl-(CH$_2$)$_p$-G-(CH$_2$)$_m$—, C4-C12 heterocyclyl-(CH$_2$)$_p$-G-(CH$_2$)$_m$—, and C3-C10 cycloalkyl-(CH$_2$)$_p$-G-(CH$_2$)$_m$—, wherein G is selected from the group consisting of O, S, N$R_6$, S(═O), S(═O)$_2$, C(═O), —C(═O)N($R_4$)—, —OC(═O)N($R_4$)—, —OC(═O)—, —N($R_4$)C(═O)N($R_4$)—, —($R_4$)N—S(═O)$_t$—, —OS(═O)$_t$—, and —OS(═O)$_t$N($R_4$)—; wherein each t is 1 or 2, p and m are each independently 0, 1, 2, 3 or 4, wherein the C6-C10 aryl-(CH$_2$)$_p$-G-(CH$_2$)$_m$—, C5-C12 heteroaryl-(CH$_2$)$_p$-G-(CH$_2$)$_m$—, C4-C12 heterocyclyl-(CH$_2$)$_p$-G-(CH$_2$)$_m$—, and C3-C10 cycloalkyl-(CH$_2$)$_p$-G-(CH$_2$)$_m$— are each optionally substituted by one or more substituents selected from the group consisting of F, Cl, Br, I, alkyl, alkenyl, alkynyl, alkoxy and cyano; when Z is a benzene ring, $R_3$ is not H;

$R_6$ is selected from the group consisting of H, D, $R_5R_4$NC(═O)—, $R_5$OC(═O)—, $R_5$C(═O)—, $R_5R_4$NS(═O)—, $R_5$OS(═O)—, $R_5$S(═O)—, $R_5R_4$NS(═O)$_2$—, $R_5$OS(═O)$_2$—, $R_5$S(═O)$_2$—, C1-C3 aliphatic, C1-C3 haloaliphatic, C1-C3 hydroxyaliphatic, C1-C3 aminoaliphatic, C1-C3 alkoxy-C1-C3 aliphatic, C1-C3 alkylamino-C1-C3 aliphatic, C1-C3 alkylthio-C1-C3 aliphatic, C6-C10 aryl-C1-C3 aliphatic, C5-C9 heteroaryl-C1-C3 aliphatic, C4-C10 heterocyclyl-C1-C3 aliphatic, C3-C10 cycloalkyl-C1-C3 aliphatic, C6-C10 aryloxy-C1-C3 aliphatic, C4-C10 heterocyclyloxy-C1-C3 aliphatic, C3-C10 cycloalkyloxy-C1-C3 aliphatic, C6-C10 arylamino-C1-C3 aliphatic, C4-C10 heterocyclylamino-C1-C3 aliphatic, C3-C10 cycloalkylamino-C1-C3 aliphatic, C6-C10 aryl, C5-C10 heteroaryl, C4-C10 heterocyclyl and C3-C10 cycloalkyl;

wherein $R_5$ and $R_4$ are each independently selected from the group consisting of H, D, C1-C3 aliphatic, C1-C3 haloaliphatic, C1-C3 hydroxyaliphatic, C1-C3 aminoaliphatic, C1-C3 alkoxy-C1-C3 aliphatic, C1-C3 alkylamino-C1-C3 aliphatic, C1-C3 alkylthio-C1-C3 aliphatic, C6-C10 aryl-C1-C3 aliphatic, C5-C9 heteroaryl-C1-C3 aliphatic, C4-C10 heterocyclyl-C1-C3 aliphatic, C3-C10 cycloalkyl-C1-C3 aliphatic, C6-C10 aryloxy-C1-C3 aliphatic, C4-C10 heterocyclyloxy-C1-C3 aliphatic, C3-C10 cycloalkyloxy-C1-C3 aliphatic, C6-C10 arylamino-C1-C3 aliphatic, C4-C10 heterocyclylamino-C1-C3 aliphatic, C3-C10 cycloalkylamino C1-C3 aliphatic, C6-C10 aryl, C5-C10 heteroaryl, C4-C10 heterocyclyl and C3-C10 cycloalkyl; with the proviso that where $R_5$ and $R_4$ are bonded to a same nitrogen atom, $R_5$ and $R_4$, together with the nitrogen atom, optionally form an optionally substituted 3-8 membered ring, an optionally substituted fused bicyclic ring or an optionally substituted spiro bicyclic ring, wherein hetero atoms in the heterocyclyl, heteroaryl, fused heterobicyclyl and/or spiro heterobicyclyl are independently selected from the group consisting of N, O, S, and/or Se, and number of the hetero atoms is 1-5;

wherein $R_3$, $R_4$, $R_5$, $R_6$ are optionally substituted by one or more substituents selected from the group consisting of hydroxyl, hydroxymethyl, carboxyl, acetylamino, alkyl, alkoxy, alkylamino, cycloalkyl, alkenyl, alkynyl, trifluoromethyl, trifluoroacetyl, thiol, halogen, nitro, amino, azido (—$N_3$), guanidyl, cyano, tert-butoxycarbonyl (-Boc), carbonyl (—C═O), oxo (═O), thio (═S), sulfonyl, aryl, heteroaryl, and heterocyclyl.

In some embodiments, $R_3$ is selected from the group consisting of H, D, F, Cl, Br, I, hydroxy, amino, nitro, cyano, methyl, ethyl, propyl, isopropyl, butyl, tert-butyl, $C_5H_{11}$, $C_6H_{13}$, $C_8H_{17}$, trifluoromethyl, hydroxymethyl, aminomethyl, methoxy, ethoxy, tert-butoxy, methylamino, ethylamino, isopropylamino, 3-hydroxypropyl, acetyl, trifluoroacetyl, cyanoacetyl, methylaminoacetyl, propionyl, isopropionyl, 2-hydroxypropanoyl, 2-aminopropanoyl, 2-chloropropanoyl, 2-bromopropanoyl, pentanoyl, hexanoyl, heptanoyl, methacryloyl, phenyl, benzoyl, p-nitrophenyl, p-methylbenzoyl, m-fluorobenzoyl, p-aminobenzoyl, p-methoxybenzoyl, 2,4-dimethylbenzoyl, m-azidobenzoyl, benzyl, p-chlorobenzyl, vinyl, propenyl, allyl, n-butenyl, isobutenyl, n-pentenyl, isopentenyl, cyclopropyl, cyclopropanoyl, cyclopentanoyl, cyclohexanoyl, 3-pyridineformyl, naphthyl, phenethylimidazolyl, pyridyl, pyrrolyl, oxazolyl, isoxazolyl, triazolyl, tetrazolyl, furyl, thienyl, thiazolyl, piperidinyl, piperazinyl, indolyl, carbazolyl, benzofuranyl, tetrahydrofuranyl, tetrahydropyranyl, pyrimidine, purine, —$N(CH_3)_2$, —C(C═O)NH—C1-C4 alkyl, —OC(C═O)—NH—C1-C4 alkyl, —OC(O═O)O—C1-C4 alkyl, —NHC(═O)NH—C1-C4 alkyl, —NHC(═O)O—C1-C4 alkyl, —NHC(═O)—C1-C4 alkyl, C1-C4 alkyl-NH—$S(═O)_2$—, C1-C4 alkyl-$S(═O)_2$—, C1-C4 alkyl-S$(═O)_2$NH—, phenyl-$(CH_2)_p$-G-$(CH_2)_m$—, fluorophenyl-$(CH_2)_p$-G-$(CH_2)_m$—, thiazolyl-$(CH_2)_p$-G-$(CH_2)_m$—, pyridyl-$(CH_2)_p$-G-$(CH_2)_m$—, phenylethyl, and cyclohexyl-$(CH_2)_p$-G-$(CH_2)_m$—, wherein G is selected from the group consisting of O, S, S(═O), $S(═O)_2$, and C(═O), p and m are each independently 0, 1, 2 or 3, wherein the $C_6$-C10 aryl-$(CH_2)_p$-G-$(CH_2)_m$— is optionally substituted by one or more substituents selected from the group consisting of F, Cl, Br, I, methyl, ethyl, propyl, ethynyl, propynyl, butynyl, methoxy, ethoxy and cyano, wherein $R_3$ is optionally substituted by one or more substituents selected from the group consisting of F, Cl, Br, I, hydroxy, hydroxymethyl, carboxy, acetylamino, C1-C6 alkyl, C1-C6 alkoxy, C1-C6 alkylamino, trifluoromethyl, trifluoroacetyl, thiol, nitro, amino, azido (—$N_3$), guanidyl, cyano, tert-butoxycarbonyl (-Boc), carbonyl (—C═O), oxo (═O), thio (═S), sulfonyl and phenyl; when Z is a benzene ring, $R_3$ is not H.

In some embodiments, $R_1$ and $R_2$ are each independently H or

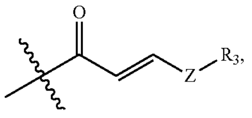

$R_1$ and $R_2$ are not H simultaneously, and Z is selected from the group consisting of benzene ring, pyridine ring, or quinoline ring and isoquinoline ring; when Z is a benzene ring, $R_3$ is selected from

| | | | | | |
|---|---|---|---|---|---|
| F | Cl | Br | I | $CH_3$ | $OCH_3$ |
| OH | CN | $CF_3$ | $OCF_3$ | $NO_2$ | $SO_2CH_3$ |
| $NH_2$ | COOH | $NHOCH_3$ | $COOCH_3$ | $N(CH_3)_2$ | $C_2H_5$ |
| $COOC_2H_5$ | $NHOC_2H_5$ | $CONH_2$ | $CONHCH_3$ | $CON(CH_3)_2$ | $CH_2CH_2OH$ |
| $CH(CH_3)OH$ | $C(CH_3)_3$ | $CH_2Br$ | 2-F-3-Cl | 2-CN-5-F | 2-F-3-Br |
| 3-Cl-4-F | 2-Cl-5-$CF_3$ | 2-F-3-Cl | 2-Cl-4-F | 3-Cl-5-F | 2-Br-5-F |
| 3-F-4-$OCH_3$ | 3-$OCH_3$-4-$OC_6H_5$ | 2-Cl-3-F | 2-Cl-4,5-2F | 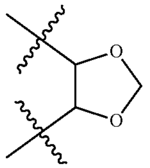 [SMILES: *C1OCOC1*] | 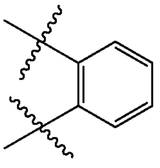 [SMILES: *c1ccccc1*] |
| 2,3-2OH | 2,4-2OH | 2,5-2OH | 2,6-2OH | 3,4-2OH | 3,5-2OH |
| 2,3,4-3OH | 2,3,5-3OH | 2,3,6-3OH | 2,4,5-3OH | 2,4,6-3OH | 2,5,6-3OH |
| 3,4,5-3OH | 3,4,6-3OH | 3,5,6-3OH | 2,3,4,5-4OH | 2,3,4,6-4OH | 2,3,4,5,6-5OH |
| 2,3-2F | 2,3-2Cl | 2,3-2Br | 2,3-2I | 2,3-2$CH_3$ | 2,3-2$OCH_3$ |
| 2,4-2F | 2,4-2Cl | 2,4-2Br | 2,4-2I | 2,4-2$CH_3$ | 2,4-2$OCH_3$ |
| 2,5-2F | 2,5-2Cl | 2,5-2Br | 2,5-2I | 2,5-2$CH_3$ | 2,5-2$OCH_3$ |
| 2,6-2F | 2,6-2Cl | 2,6-2Br | 2,6-2I | 2,6-2$CH_3$ | 2,6-2$OCH_3$ |
| 3,4-2F | 3,4-2Cl | 3,4-2Br | 3,4-2I | 3,4-2$CH_3$ | 3,4-2$OCH_3$ |
| 3,5-2F | 3,5-2Cl | 3,5-2Br | 3,5-2I | 3,5-2$CH_3$ | 3,5-2$OCH_3$ |
| 2,3,4-3F | 2,3,4-3Cl | 2,3,4-3Br | 2,3,4-3I | 2,3,4-3$CH_3$ | 2,3,4-3$OCH_3$ |
| 2,3,5-3F | 2,3,5-3Cl | 2,3,5-3Br | 2,3,5-3I | 2,3,5-3$CH_3$ | 2,3,5-3$OCH_3$ |
| 2,3,6-3F | 2,3,6-3Cl | 2,3,6-3Br | 2,3,6-3I | 2,3,6-3$CH_3$ | 2,3,6-3$OCH_3$ |
| 2,4,5-3F | 2,4,5-3Cl | 2,4,5-3Br | 2,4,5-3I | 2,4,5-3$CH_3$ | 2,4,5-3$OCH_3$ |
| 2,4,6-3F | 2,4,6-3Cl | 2,4,6-3Br | 2,4,6-3I | 2,4,6-3$CH_3$ | 2,4,6-3$OCH_3$ |
| 2,5,6-3F | 2,5,6-3Cl | 2,5,6-3Br | 2,5,6-3I | 2,5,6-3$CH_3$ | 2,5,6-3$OCH_3$ |
| 3,4,5-3F | 3,4,5-3Cl | 3,4,5-3Br | 3,4,5-3I | 3,4,5-3$CH_3$ | 3,4,5-3$OCH_3$ |
| 3,4,6-3F | 3,4,6-3Cl | 3,4,6-3Br | 3,4,6-3I | 3,4,6-3$CH_3$ | 3,4,6-3$OCH_3$ |
| 3,5,6-3F | 3,5,6-3Cl | 3,5,6-3Br | 3,5,6-3I | 3,5,6-3$CH_3$ | 3,5,6-3$OCH_3$ |
| 2,3,4,5-4F | 2,3,4,5-4Cl | 2,3,4,5-4Br | 2,3,4,5-4I | 2,3,4,5-4$CH_3$ | 2,3,4,5-4$OCH_3$ |

-continued

| | | | | | |
|---|---|---|---|---|---|
| 2,3,4,6-4F | 2,3,4,6-4Cl | 2,3,4,6-4 Br | 2,3,4,6-4I | 2,3,4,6-4 $CH_3$ | 2,3,4,6-4 $OCH_3$ |
| 2,3,4,5,6-5F | 2,3,4,5,6-5Cl | 2,3,4,5,6-5Br | 2,3,4,5,6-5I | 2,3,4,5,6-5$CH_3$ | 2,3,4,5,6-5$OCH_3$ |
| 2,3-2$CF_3$ | 2,3,4-3$CF_3$ | 3,4,5-3$CF_3$ | 2,3-2$OCF_3$ | 2,3,4-3$OCF_3$ | 3,4,5-3$OCF_3$ |
| 2,4-2$CF_3$ | 2,3,5-3$CF_3$ | 3,4,6-3$CF_3$ | 2,4-2$OCF_3$ | 2,3,5-3$OCF_3$ | 3,4,6-3$OCF_3$ |
| 2,5-2$CF_3$ | 2,3,6-3$CF_3$ | 3,5,6-3$CF_3$ | 2,5-2$OCF_3$ | 2,3,6-3$OCF_3$ | 3,5,6-3$OCF_3$ |
| 2,6-2$CF_3$ | 2,4,5-3$CF_3$ | 2,3,4,5-4$CF_3$ | 2,6-2$OCF_3$ | 2,4,5-3$OCF_3$ | 2,3,4,5-4$OCF_3$ |
| 3,4-2$CF_3$ | 2,4,6-3$CF_3$ | 2,3,4,6-4$CF_3$ | 3,4-2$OCF_3$ | 2,4,6-3$OCF_3$ | 2,3,4,6-4$OCF_3$ |
| 3,5-2$CF_3$ | 2,5,6-3$CF_3$ | 2,3,4,5,6-5$CF_3$ | 3,5-2$OCF_3$ | 2,5,6-3$OCF_3$ | 2,3,4,5,6-5$OCF_3$ |

when Z is a pyridine ring, a quinoline ring, or a isoquinoline ring, at least one of $R_3$ is selected from:

| | | | | | |
|---|---|---|---|---|---|
| F | Cl | Br | I | $CH_3$ | $OCH_3$ |
| OH | CN | $CF_3$ | $OCF_3$ | $NO_2$ | $SO_2CH_3$ |
| $NH_2$ | COOH | $NHOCH_3$ | $COOCH_3$ | $N(CH_3)_2$ | $C_2H_5$ |
| $COOC_2H_5$ | $NHOC_2H_5$ | $CONH_2$ | $CONHCH_3$ | $CON(CH_3)_2$ | $CH_2CH_2OH$ |
| $CH(CH_3)OH$ | $C(CH_3)_3$ | $CH_2Br$ | H | | |

Optionally, the stereoisomer of the compound represented by Formula (I) comprises a geometric isomer of the compound represented by Formula (I).

Optionally, the solvate of the compound represented by Formula (I) comprises a hydrate of the compound represented by Formula (I).

In some embodiments, the present disclosure relates to a pharmaceutical composition comprising the compounds disclosed herein.

In some embodiments, the pharmaceutical compositions in the present disclosure further comprise a pharmaceutically acceptable excipient, a carrier, an adjuvant, a solvent or a combination thereof.

Optionally, the excipient is selected from a diluent, a filler, a binder, disintegrant, a lubricant, a glidant, a granulating agent, a coating agent, a wetting agent, a solvent, a co-solvent, a suspending agent, a emulsifier, a sweetener, a corrigent, a taste masking agent, a colorant, an anti-caking agent, a humectant, a chelating agent, a plasticizer, a tackifier, an antioxidant, a preservative, a stabilizer, a surfactant or a buffer.

Optionally, the carrier is selected from a disintegrant, a controlled-release polymer, a lubricant, a diluent or a colorant.

In another aspect, the present disclosure relates to a method for treatment of hyperproliferative diseases in mammals, comprising administering an effective amount of the compound or the pharmaceutical composition of the present disclosure to the mammals.

Optionally, the mammals comprise humans.

Optionally, the hyperproliferative diseases are selected from the group consisting of liver cancer, leukemia, breast cancer, colon adenocarcinoma, gastric cancer, lung cancer, Bart's esophageal cancer, cervical cancer, pancreatic cancer, endometrial cancer, bone cancer, lymphoma, kidney cancer, brain cancer, nerve cancer, nasopharyngeal cancer, oral cancer and colorectal cancer.

The biological test results show that the compounds in the present disclosure can inhibit tumor proliferation.

Any embodiment of any aspect of the present disclosure can be combined with other embodiments as long as they do not appear contradictory. In addition, in any embodiment of any aspect of the present disclosure, any technical feature can be applied to the technical feature in other embodiments, as long as they do not appear contradictory.

The foregoing description merely summarizes certain aspects of the disclosure, but is not limited to these aspects. These and other aspects will be described in more detail below.

DETAILED DESCRIPTION OF THE INVENTION

Definitions and General Terms

Some embodiments disclosed herein will now be described in detail, examples of which are illustrated by the accompanying structural and chemical formulas. The disclosure is intended to cover all alternative, modified and equivalent technical solutions, all of which are included within the scope disclosed herein as defined by the claims. One skilled in the art will recognize that many methods and materials similar or equivalent to those described herein can be used in the practice disclosed herein. Disclosed herein is in no way limited to the methods and materials. In the event that one or more of the incorporated literature, patents and similar materials differ from or contradict this application (including but not limited to the term definition, term usage and/or described techniques, and the like), the present application shall prevail.

It should be further recognized that certain features disclosed herein have been described in multiple independent embodiments for clarity, but may be also provided in combination in a single embodiment. On the contrary, various features disclosed herein have been described in a single embodiment for the sake of brevity, but can be also provided individually or in any suitable sub combination.

Unless otherwise stated, all technical terms used in the present disclosure have the same meanings as those of the skilled in the art to which the disclosure belongs. All patents and public publications involved in the disclosure are incorporated into the present disclosure as a whole by reference.

Unless otherwise stated, the following definitions used in the present application should be used. For purposes of the present disclosure, the chemical elements are identified in accordance with the Periodic Table of the Elements, CAS version and the *Handbook of Chemistry and Physics*, $75^{th}$ Ed. 1994. Additionally, general principles of organic chemistry are described in "Organic Chemistry", Thomas Sorrell, University Science Books, Sausalito: 1999, and "*March's Advanced Organic Chemistry*" by Michael B. Smith and Jerry March, John Wiley & Sons, New York: 2007, all of which are incorporated herein by reference in their entireties.

As described herein, compounds may be optionally substituted with one or more substituents, such as those illustrated above, or as exemplified by particular classes, subclasses and species disclosed herein. It will be appreciated that the term "optionally substituted" is used interchangeably with the term "substituted or unsubstituted". In general, the term "substituted" whether preceded by the term "optionally" or not, refers to the replacement of one or more hydrogen radicals in a given structure with the radical of a specific substituent. Unless otherwise indicated, an optionally substituted group may have a substituent at each substitutable position of the group. When more than one position in a given structure may be substituted with more than one substituent selected from a specific group, the substituent may be either the same or different at each position, wherein the substituents may be, but are not limited to, haloalkyl, hydroxyl, halo, cyano, aryl, alkyl, alkenly, alkynyl, heteroaryl, alkylamino, alkylthio, alkoxy, heterocyclyl, thiol, nitro, amino, aryloxy, heteroaryloxy, oxo (═O), carboxy, hydroxyl-substituted alkoxy, hydroxyl-substituted alkyl-C(═O)—, alkyl-C(═O)—, alkyl-S(═O)—, alkyl-S(═O)$_2$—, hydroxyl-substituted alkyl-S(═O)—, hydroxyl-substituted alkyl-S(═O)$_2$— and/or carboxyl alkoxy, and the like.

The term "subject" used refers to animals. The animal is typically a mammal. Subjects, for example, also refer to primates (such as human, male or female), bovines, sheep, goats, horses, dogs, cats, rabbits, rats, mice, fish, birds, and the like. In some embodiments, the subject is primate. In other embodiments, the subject is human.

The term "patient" as used herein refers to human beings (including adults and children) or other animals. In some embodiments, "patient" refers to human.

The term "comprising" used herein is an open expression, which includes the contents specific in the present disclosure, but does not exclude other aspects.

The term "stereoisomer" refers to compounds with the same chemical structure but different arrangement of atoms or groups in space. The compounds disclosed herein can contain asymmetric centers or chiral centers, so there are different stereoisomers. All stereoisomeric forms of compounds disclosed herein, including but not limited to enantiomers, diastereomers, conformational isomers (rotational isomers), geometric isomers (cis/trans) isomers, rotation-hindered isomers and mixtures thereof, such as racemic mixtures, form a part of the disclosure.

The term "chirality" refers to a molecule which cannot overlap with its mirror image; the term "non-chirality" refers to a molecule that can overlap with its mirror image.

The term "enantiomer" refers to two isomers of a compound that cannot overlap but mirror each other.

The term "diastereomers" refers to stereoisomers with two or more chiral centers and their molecules are not mirror images of each other. Diastereomers have different physical properties, such as melting point, boiling point, spectral properties and reactivity. Diastereomeric mixtures can be separated by high-resolution analytical operations such as electrophoresis and chromatography, e.g., HPLC.

The stereochemistry definitions and rules used herein generally follow S. P. Parker, Ed., McGraw Hill Dictionary of chemical terms (1984) McGraw Hill Book Company, New York; and Eliel, E. and Wilen, S., "*Stereochemistry of Organic Compounds*", John Wiley & Sons, Inc., New York, 1994.

Many organic compounds exist in the form of optical activity, i.e., they have the ability to rotate the plane of plane-polarized light. When describing optically active compounds, the prefixes D and L or R and S are used to express the absolute configuration of molecules with respect to one or more chiral centers. The prefixes d and/or (+) and (−) are symbols used to specify the rotation of planar polarized light caused by a compound, where (−) or l denotes that the compound is left-handed. Compounds prefixed with (+) or dare dextral. A specific stereoisomer is an enantiomer, and the mixture of these isomers is called an enantiomer mixture. The 50:50 mixture of enantiomers is called racemic mixture or racemic, which can occur when there is no stereoselectivity or stereospecificity in the process of chemical reaction.

Any asymmetric atom (e.g., carbon, and the like) of the compounds disclosed herein can exist in racemic or enantiomeric enriched forms, such as (R)-, (S)- or (R,S)-configurations. In some embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in (R)- or (S)-configuration.

Depending on the choice of starting materials and methods, the compounds disclosed herein may exist in the form of one of possible isomers or a mixture thereof, such as a mixture of racemates and diastereomers, depending on the number of asymmetric carbon atoms. Optically active (R)- or (S)-isomers can be prepared using chiral synthons or chiral reagents, or resolved using conventional techniques. If the compound contains a double bond, the substituent may be in E or Z configuration. If the compound contains disubstituted naphthenic groups, the substituents of naphthenic groups may have cis or trans configuration.

The mixture of any stereoisomers can be separated into pure or substantially pure geometric isomers, enantiomers and/or diastereomers, for example, by chromatography and/or fractional crystallization, depending on the differences in the physicochemical properties of the components.

The raceme of any end product or intermediate obtained can be separated into optical enantiomers by known methods, such as separation of its diastereomeric salts. Racemic products can be also separated by chiral chromatography, such as high performance liquid chromatography (HPLC) using chiral adsorbents. In particular, enantiomers can be prepared by asymmetric synthesis, for example, with reference to Jacques, et al., Enantiomers, Racemates and Resolutions (Wiley Interscience, New York, 1981); Principles of Asymmetric Synthesis ($2^{nd}$ Ed. Robert E. Gawley, Jeffrey Aubé, Elsevier, Oxford, U K, 2012); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, IN 1972); Chiral Separation Techniques: A Practical Approach (Subramanian, G. Ed., Wiley-VCH Verlag Gmbh & Co. KGaA, Weinheim, Germany, 2007).

As described herein, compounds may be optionally substituted with one or more substituents, such as those illustrated above, or as exemplified by particular classes, subclasses and species disclosed herein.

In addition, it should be noted that unless it is explicitly pointed out in other ways, the description methods adopted herein "each . . . independently" and " . . . independently" and " . . . independently" are interchangeable, which should be understood in a broad sense. It can mean that in different groups, the specific options expressed by the same symbols do not affect each other. It can also indicate that in the same group, the specific options expressed by the same symbols do not affect each other.

The term "aliphatic" or "aliphatic group" refers to a straight-chain (i.e., unbranched) or branched substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms. In yet other embodiments, aliphatic groups contain 1-4 carbon atoms and in yet other embodiments, aliphatic groups contain 1-3 carbon atoms. Suitable aliphatic groups comprise, but are not limited to, linear or branched, substituted or unsubstituted alkyl, alkenyl, or alkynyl groups, such as methyl, ethyl, propyl, isopropyl, butyl, tert-butyl, hexyl, isobutyl, sec-butyl, vinyl, and the like.

The term "haloaliphatic" refers to an aliphatic group substituted by one or more of the same or different halogen atoms, wherein the aliphatic group is as defined herein, halogen atoms refer to F, Cl, Br or I. Some non-limiting examples comprise trifluoromethyl, trifluoroethyl, chloromethyl, 2-chloroethylene, and the like.

The term "hydroxyaliphatic" refers to an aliphatic group substituted by one or more hydroxy groups, wherein the aliphatic group is as defined herein. Some non-limiting examples comprise hydroxyethyl, 2-hydroxypropyl, hydroxymethyl, and the like.

The term "aminoaliphatic" refers to an aliphatic group substituted by one or more amino groups, wherein the aliphatic group is as defined herein. Some non-limiting examples comprise aminomethyl, 2-aminoethyl, 2-aminoisopropyl, and the like.

The term "alkyl" refers to a saturated linear or branched-chain monovalent hydrocarbon radical of 1-20 carbon atoms, 1-10 carbon atoms, 1-6 carbon atoms, 1-4 carbon atoms, or 1-3 carbon atoms, wherein the alkyl radical may be optionally substituted independently with one or more substituents described below. Further examples of alkyl groups comprise, but are not limited to methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimety-2-butyl ($—C(CH_3)_2CH(CH_3)_2$), 3,3-dimethyl-2-butyl ($—CH(CH_3)C(CH_3)_3$), 1-heptyl, 1-octyl, and the like. The terms "alkyl" and the prefix "alk-" are inclusive of both straight chain and branched saturated carbon chain.

The term "alkenyl" refers to a linear or branched-chain monovalent hydrocarbon radical of 2-12 carbon atoms, 2-8 carbon atoms, 2-6 carbon atoms, or 2-4 carbon atoms, with at least one site of unsaturation i.e., a carbon-carbon, $sp^2$ double bond, wherein the alkenyl radical may be optionally substituted independently with one or more substituents described herein, and comprises radicals having "cis" and "trans" orientations, or alternatively, "E" and "Z" orientations. Some non-limiting examples comprise ethenyl or vinyl ($—CH═CH_2$), allyl ($—CH_2CH═CH_2$), and the like.

The term "alkynyl" refers to a linear or branched-chain monovalent hydrocarbon radical of 2-12 carbon atoms, 2-8 carbon atoms, 2-6 carbon atoms, or 2-4 carbon atoms, with at least one site of unsaturation, i.e., a carbon-carbon, sp triple bond, wherein the alkynyi radical may be optionally substituted independently with one or more substituents described herein. Some non-limiting examples comprise ethynyl ($—C≡CH$), 2-propynyl ($—CH_2C≡CH$), and the like.

The term "hydroxy-substituted alkyl" refers to an alkyl group substituted with one or more hydroxy groups, wherein the alkyl group is as defined herein. Some non-limiting examples comprise hydroxymethyl, hydroxyethyl, 1,2-dihydroxyethyl, and the like.

The term "carbocycle", "carbocyclyl", "cycloalkyl" refers to a monovalent or multivalent, non-aromatic, saturated or partially unsaturated ring, and not containing heteroatoms, having 3 to 12 carbon atoms as a monocyclic ring or 7 to 12 carbon atoms as a bicyclic ring or a tricyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system. Some non-limiting examples of cycloaliphatic groups comprise cycloalkyl, cycloalkenyl, and cycloalkynyl. Further examples of cycloaliphatic groups comprise cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantly, and the like. The "cycloaliphatic", "carbocycle", "carbocyclyl", or "cycloalkyl" may be substituted or unsubstituted, wherein the substituent may be, but is not limited to, haloalkyl, hydroxy, amino, halo, cyano, aryl, heteroaryl, alkoxy, alkylamino, alkyl, alkenyl, alkynyl, heterocyclyl, thiol, nitro, arloxy, hydroxy-substituted alkoxy, hydroxy-substituted-$C(═O)—$, alkyl-$C(═O)$, alkyl-$S(═O)$, alkyl-$S(═O)_2—$, hydroxy-substituted alkyl-$S(═O)—$, hydroxy-substituted alkyl-$S(═O)_2—$, carboxyalkoxy, and the like.

The term "cycloalkyloxy" or "carbocyclyloxy" refers to an optionally substituted cycloalkyl radical or carbocyclyl radical, as defined hererin, attached to an oxygen atom, which is connected to the rest of the molecule. Some non-limiting examples comprise cyclopropyloxy, cyclopentyloxy, cyclohexyloxy, hydroxy-substituted cyclopropyloxy and the like.

The term "cycloalkylamino" refers to an amino group substituted with one or two cycloalkyl groups, wherein the cycloalkyl groups as defined herein. Some non-limiting examples comprise cyclopropylamino, cyclopentylamino, cyclohexylamino, hydroxy-substituted cyclopropylamino, dicyclohexylamino, dicyclopropylamino, and the like.

The term "cycloalkyloxyaliphatic" refers to an aliphatic group substituted with one or more cycloalkyloxy groups, wherein the aliphatic group and cycloalkyloxy group are as defined herein. Some non-limiting examples comprise cyclopropyloxymethyl, cyclopropyloxyethyl, cyclopentyloxymethyl, cyclopentyloxyethyl, cyclohexyloxyethyl, halocyclopropyloxyetryl, anxd the like.

The term "cycloalkylaminoaliphatic" refers to an aliphatic group substituted with one or more cycloalkylamino groups, wherein the aliphatic group and cycloallylamino group are as dedined herein Some non-limiting examples comprise cyclopropy laminomethyl, cyclopropylaminethyl, cyclopentylaminomethyl, cyclopentylaminoethyl, cyclohexylaminoethyl, halocyclopropylaminoethyl, and thelike.

The term "cycloalkylaliphatic" or "carbocyclylaliphatic" refers to an aliphatic group substituted with one or more cycloalkyl Igroups or carbocyclyl groups, wherein the carbocyclyl, cycloalkyl group and aliphatic group are as defined herein. Some non-limiting examples comprise cyclopropylmethyl, cyclopropylethyl, cyclopropylpropyl.

The term "heterocycle", "heterocyclyl", "heterocycloaliphatic" or "heterocyclic" as used interchangeably herein refers to a monocyclic, bicyclic, or tricyclic ring system in which one or more ring members are an independently selected heteroatom and that is completely saturated or that contains one or more units of unsaturation, but not aromatic having a single point of attachment to the rest of the molecule. One or more ring atoms are optionally substituted independently with one or more substituents described herein. In some embodiments, the "heterocycle", "heterocyclyl", "heterocycloaliphatic" or "heterocyclic" group is a monocycle having 3 to 7 ring members (e.g., 1 to 6 carbon atoms and 1 to 3 heteroatoms selected from N, O, P or S, wherein the S or P is optionally substituted with one or more oxo to provide the group SO or $SO_2$, PO or $PO_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P or S, wherein the S or P is optionally substituted with one or more oxo to provide the group SO or $SO_2$, PO or $PO_2$).

The heterocyclyl may be a carbon radical or heteroatom radical. "Hetetocyclyl" also comprises radicals, wherein heterocycle radicals are fused with a saturated, partially unsaturated ring, or heterocyclic ring. Some non-limiting examples of heterocyclic rings comprise pyrrolidinyl, tetrahydrofuranyl, tetrahydrothienyl, dihydrofuranyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, piperidino, homopiperidinyl, epoxypropyl, azepanyl, oxepanyl, thiepanyl, 4-methoxy-piperidin-1-yl, 1,2,3,6-tetrahydropyridin-1-yl, oxazepinyl, diazepinyl, thiazepinyl, pyrrolin-1-yl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydrothienyl, pyrazolidinylimidazolinyl, imidazolidinyl, 1,2,3,4-tetrahydroisoquinolinyl, 1,2,6-thiadiazane-1,1-dioxo-2-yl, 4-hydroxy-1,4-azaphosphine-4-oxid-1-yl, 2-hydroxy-1-(piperazin-1-yl)ethanon-4-yl, 2-hydroxy-1-(5,6-dihydro-1,2,4-triazin (4H)enthanon-4-yl, 5,6-dihydro-4H-1,2,4-oxadiazin-4-yl, 2-hydroxy-1-(5,6-dihydropyridin-1 (2H)-yl)ethanon-4-yl, 3-azabicyco[3,1,0]hexanyl, 3-azabicyclo[4,1,0]heptanyl, azabicyclol[2.2.2]hexanyl, 2-methyl-5,6,7,8-tetrahydro-[1,2,4]triazolo[1,5-c]pyrimidin-6-yl, 4,5,6,7-tetrahydroisoxazol[4,3-c]pyridin-5-yl, 3H-indolyl-2-oxo-azabicyclo[2,2,1]heptan-5-yl, 2-oxo-5-azabicyclo[2,2,2]octan-5-yl, quinolizinyl and N-pyridyl urea. Some non-limiting examples of a heterocyclic ring comprise 1,1-dioxo-thiomorpholinyl and heterocyclic group wherein two carbon atoms on the ring are substituted with oxo (=O) moieties are pyrimidindionyl. The heterocyclic group herein may be substituted or unsubstituted, wherein the substituted may be, but is not limited to, oxo (=O), hydroxy, amino, halo, cyano, heteroaryl, alkoxy, alkylamino, alkyl, haloallkyl, alkenyl, alkynyl, heterocyclyl, thiol, nitro, aryloxy, hydroxyl-substituted alkoxy, hydroxyl-substituted alkyl-C(=O)—, alkyl-C(=O)—, alkyl-S(=O), hydroxyl-substituted alkyl-S(=O), hydroxyl-substituted alkyl-$S(=O)_2$—, carboxyalkoxy, and the like.

The term "heterocyclylaliphatic" refers to heterocyclic-substituted aliphatic group, wherein the heterocyclic radical and aliphatic group are as defined herein. Some non-limiting examples comprise pyrrol-2-ylmethyl, piperidin-2-ylethyl, piperazin-2-ylethyl, piperidin-2-ylmethyl, and the like.

The term "heterocyclyloxy" refers to optionally substituted heterocyclyl radical, as defined herein, connected to an oxygen atom, and the oxygen atom serves as the attaching point to the rest of the molecule. Some non-limiting examples comprise pyrrol-2-yloxy, pyrrol-3-yloxy, piperidin-2-yloxy, piperidin-3-yloxy, piperazin-2-yloxy, piperidin-4-yloxy and the like.

The term "heterocyclylamino" refers to an amino group substituted with one or two heterocyclyl groups, wherein the heterocyclyl group is as defined herein. Some non-limiting examples comprise pyrrol-2-ylamino, pyrrol-3-ylamino, piperidin-2-ylamino, piperidin-3-ylamnino, piperidin-4-ylamino, piperazin-2-ylamino, diprrol-2-ylamino, and the like.

The term "hetcrocyclyloxyaliphatic" relers to an aliphatic group substituted with one or more heterocyclyloxy groups, wherein the aliphatic group and heterocyclyloxy group are as defined herein. Some non-limiting examples comprise pyrrol-2-yloxymethyl, piperazin-3-yloxyethyl, piperazin-2-yloxyethyl, morpholin-2-yloxymethyl, piperidin-2-yloxyethyl, and the like. The term "heterocyclylaminoaliphatic" refers to an aliphatic group substituted with one or more heterocyclylamino groups, wherein the aliphatic group and heterocyclylamino group are as defined herein. Some non-limiting examples comprise pyrrol-2-yl-aminomethyl, piperazin-3-yl-aminoethyl, piperazin-2-yl-aminoethyl, piperidin-2-yl-aminoethyl, morpholin-2-yl-aminomethyl, and the like.

The term "heteroatom" refers to one or more of oxygen, sulfur, nitrogen, phosphorus, and selenium, including the forms of any oxidized state of nitrogen, sulfur, and phosphorus; the forms of primary, secondary, and tertiary amines and quaternary ammonium salts; or a substitutable nitrogen of a heterocyclic ring, for example, N (such as N in 3,4-dihydro-2H-pyrrolyl), NH (such as NH in pyrrolidinyl) or $NR^{10}$ (such as $NR^{10}$ in N-substituted pyrrolidinyl).

The term "halogen" refers to F, Cl, Br or I.

The term "unsaturated" refers to a moiety having one or more degrees of unsaturation.

The term "alkoxy" refers to an alkyl group, as previously defined, attached to the principal carbon chain through an oxygen ("alkoxy") atom. Some non-limiting examples comprise methoxy, ethoxy, propoxy, butoxy, and the like. The alkoxy defined above may be substituted or unsubstituted, wherein the substituent may be, but is not limited to, hydroxy, amino, halo, cyano, alkoxy, alkyl, alkenyl, alkynyl, thiol, nitro, and the like.

The term "hydroxy-substituted alkoxy" or "hydroxy-alkoxy" refers to an alkoxy group substituted with one or more hydroxy groups, wherein the alkoxy group is as defined above. Some non-limiting examples comprise hydroxymethoxy, 2-hydroxyethoxy, 2-hydroxypropoxy, 2-hydroxyisopropoxy, and the like.

The term "aminoalkoxy" refers to an alkoxy group substituted with one or more amino groups, wherein the alkoxy group is as defined above. Some non-limiting examples comprise aminomethoxy, 2-aminoethoxy, 2-aminopropoxy, 2-aminoisopropoxy, and the like.

The term "haloalkyl", "haloalkenyl" or "haloalkoxy" refers to an alkyl group, alkenyl group or alkoxy group substituted with one or more halogen atoms. Some non-limiting examples comprise trifluoromethyl, 2-chloro-ethenyl, trifluoromethoxy, and the like.

The term "aryl" refers to monocyclic, bicyclic, and tricyclic carbocyclic ring systems having a total of 6 to 14 ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of aryl rings comprise phenyl, naphthyl, and anthracene. The aryl defined herein may be substituted or unsubstituted, wherein the substituent may be, but is not limited to, hydroxy, amino, halogen, cyano, aryl, heteroaryl, alkoxy, alkylamino, alkyl, haloalkyl, alkenyl, alkenyl, alkynyl heterocyclyl, thiol, nitro, aryloxy, hydroxy-substituted alkoxy, hydroxy substituted alkyl-C(═O)—, alkyl-C(═O)—, alkyl-S(═O)—, alkyl-S(═O)$_2$—, hydroxy substituted alkyl-S(═O)—, hydroxy-substituted alky-S(═O)$_2$—, carboxyalkoxy, and the like.

The term "fluoro-substituted phenyl" refers to a phenyl group substituted with one or more fluorine atoms.

The term "arylaliphatic" refers to an aliphatic group substituted with one or more aryl groups, wherein the aliphatic group and the aryl group are as defined herein. Some non-limiting examples comprise phenylethyl, phenylmethyl, (p-toly) ethyl, styryl, and the like.

The term "aryloxy" refers to optionally substituted aryl radicals, as defined herein, attached to an oxygen atom, wherein the oxygen atom serves as the attaching point to the rest of the molecule, wherein the aryl radical is as defined herein. Some non-limiting examples comprise phenyloxy, methylphenyloxy, ethylphenyloxy, and the like.

The term "arylamino" refers to an amino group substituted with one or two aryl groups, wherein the aryl group is as defined herein. Some non-limiting examples comprise phenylamino, (p-fluoropheny) amino, diphenylamino, ditolylamino, (di-p-tolyl)amino, and the like.

The term "aryloxyaliphatic" refers to an aliphatic group substituted with one or more aryloxy groups, wherein the alkoxy group and the aliphatic group are as defined herein. Some no-limiting examples comprise phenyloxymethoxy, phenyloxyethyl, tolyloxyethyl, phenyloxypropoxy, and the like.

The term "heteroaryloxyaliphatic" refers to an aliphatic group may be substituted with one or more heteroaryloxy groups, wherein the heteroaryloxy group and the aliphatic group are as defined herein. Some non-limiting examples comprise furanyloxymethyl, pyrimidinyloxyethyl, and the like.

The term "arylaminoaliphatic" refers to an aliphatic group substituted with one or more arylamino groups, wherein the arylamino group and the aliphatic group are as defined herein. Some non-limiting examples comprise phenylaminomethyl, phenylaminoethyl, tolylaminoethyl, phenylaminopropyl, phenylaminoallyl, and the like.

The term "arylalkoxy" refers to an alkoxy group substituted with one or more aryl groups, wherein the aryl group and the alkoxy group are as defined herein. Some non-limiting examples, comprise phenylmethoxy, phenylethoxy, (p-tolyl) methoxy, phenylpropoxy, and the like. The aryl defined herein may be substituted or unsubstituted, wherein the substituent may be, but is not limited to, hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkox, hydroxyl-substituted alkyl-C(═O)—, alkyl-C(═O)—, alkyl-S(═O)—, alkyl-S(═O)$_2$—, hydroxy-substituted alkyl-S(═O)—, hydroxy-substituted alkyl-S(═O)$_2$—, carboxyalkoxy, and the like.

The term "arylalkylamino" refers to an alkylamino group substituted with one or more aryl groups, wherein the aryl group and the alkylamino group are as defined herein. Some non-limiting examples comprise phenylmethylamino, phenylethylamino, phenylpropylamino, (p-tolyl)methylamino, and the like.

The term "heteroaryl" used alone or as part of a larger moiety as in "heteroaralkyl" or "heteroarylalkoxy" refers to monocyclic, bicyclic, and tricyclic ring systems having a total of 5 to 14 ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic". The heteroaryl defined herein may be substituted or unsubstituted, wherein the substituent may be, but is not limited to, hydroxy, amino, halogen, cyano, aryl, heteraryl, alkoxy, alkylamino, alkyl, haloalkyl, alkenyl, alkynyl, heterocyclyl, thiol, nitro, aryloxy, hydroxy-substituted alkoxy, hydroxy substituted alkyl-C(═O)—, alkyl-C(═O)—, alkyl S(═O)—, alkyl-S(═O)$_2$—, hydroxy-substituted alkyl-S(═O)—, hydroxy-substituted alky-S(═O)$_2$—, carboxyalkoxy, and the like.

In other embodiments, some non-limiting examples of suitable heteroaryl rings comprise the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 4-methylisoxazol-5-yl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazoly), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, 1,3,4-thiadiazol-2-yl, pyrazinyl, 2-pyrazinyl, 1,3,5-triazinyl, benzo[d]thiazol-2-yl, imidazo[1,5-a]pyridyl and also comprise the following bicycles: benzimidazolyl, benzofuryl, benzothiophenyl, benzothiazolyl, indolyl (e.g., 2-indolyl), purinyl, quinolinyl (e.g., 2-quinolinyl, 3-quinolinyl, 4-quinolinyl), or isoquinolinyl (e.g., 1-isoquinolinyl, 3-isoquinolinyl, or 4-isoquinolinyl).

The term "heteroaryloxy" refers to optionally substituted aryl radicals, as defined herein, attached to an oxygen atom, wherein the oxygen atom serves as the attaching point to the rest of the molecule. Some non-limiting examples comprise pyrid-2-yloxy, thiazol-2-yloxy, imidazol-2-yloxy, pyrimidin-2-yloxy, and the like.

The term "carboxyalkoxy" refers to an alkoxy group substituted with one or more carboxy groups, wherein the alkoxy group and the carboxy group are as defined herein. Some non-limiting examples comprise carboxymethoxy, carboxyethoxy, and the like.

The term "alkylthio" refers to radicals containing a linear or branched alkyl radical, of one to ten carbon atoms, attached to a divalent sulfur atom. In other embodiments, alkylthio radicals are lower alkylthio radicals having one to three carbon atoms. Some non-limiting examples of "alkylthio" comprise methylthio ($CH_3S$—). The term "haloalklthio" refers to radicals containing a haloalkyl radical, of one to ten carbon atoms, attached to a divalent sulfur atom. In other embodiments, haloalkylthio radicals are lower haloalkylthio radicals having one to three carbon atoms. Some non-limiting examples of "haloalkylthio" comprise trifluoromethylthio.

The term "alkylamino" refers to N-alkylamino" and "N,N-dialkylamino", wherein amino groups are independently substituted with one alkyl radical or with two alkyl radicals, respectively. In other embodiments, alkylamino radicals are "lower alkylamino" radicals having one or two alkyl radicals of one to six carbon atoms, attached to a nitrogen atom. In still other embodiments, alkylamino radicals are lower alkylamino radicals having one to three carbon atoms. Some non-limiting examples of suitable alkylamino radicals comprise mono or dialky lamino such as N-methylamino, N-ethylamino, N, N-dimethylamino, N, N-diethylamino, and the like.

The term "heteroarylamino" refers to amino groups substituted with one or two heteroaryl radicals, wherein the heteroaryl radicali as defined herein. Some non-limiting examples of heteroarylamino comprise N-thienylamino, and the like. In other embodiments, the "heteroarylamino" radicals comprise substituted on the heteroaryl ring portion of the radical.

The term "heteroarylaliphatic" refers to aliphatic groups substituted with one or more heteroaryl radicals, wherein the heteroaryl radical and the aliphatic group are as defined herein. Some non-limiting examples of heteroarylaliphatic comprise thiophen-2-ylpropenyl, pyridin-4-ylethyl, imidazol-2-methyl, furan-2-ethyl, indole-3-methyl, and the like.

The term "heteroarylalkyl" refers to alkyl groups substituted with one or more heteroaryl radicals, wherein the heteroaryl radical and the alkyl group are as defined herein. Some non-limiting examples of heteroarylalkyl comprise imidazol-2-methyl, furan-2-ethyl, indole-3-methyl, and the like.

The term "heteroarylalkylamino" refers to nitrogen-containing heteroarylalkyl radicals attached through a nitrogen atom to other radicals, wherein the heteroarylalkyl radicals is as defined herein. Some non-limiting examples of heteroarylalkylamino comprise pyridin-2-methylamino, thiazol-2-ethylamino, imidazol-2-ethylamino, pyrimidin-2-propylamino, pyrimidin-2-methylamino, and the like.

The term "heteroarylalkoxy" refers to oxy-containing heteroarylalkyl radicals attached through an oxygen atom to other radicals, wherein the heteroarylalkyl radical is as defined herein. Some non-limiting examples of such radicals comprise pyridin-2-ylmethoxy, thiazol-2-ylethoxy, imidazol-2-ylethoxy, pyrimidin-2-ylpropoxy, pyrimidin-2-ylmethoxy, and the like, The term "fused bicyclic", "fused cyclic", "fused bicyclyl" or "fused cyclyl" refers to saturated or unsaturated fused ring system, which involves a bicyclic ring system that is not aromatic. Such a system may contain isolated or conjugated unsaturated moiety, but does not contain aromatic or heteroaromatic rings in its core structure (but may have aromatic substitution thereon). Each cyclic ring in the fused bicyclyl can be either a carbocyclic or a heteroalicyclic. Some non-limiting examples of fused bicyclic ring system comprise hexahydro-furo[3,2-b]furan, 2,3,3a,4,7,7a-hexahydro-1H-indene, 7-azabicyclo[2.3.0]heptane, fused bicyclo[3.3.0]octane, fused bicyclo[3.1.0]hexane, 1,2,3,4,4a,5,8,8a-octahydro naphthalene, and the like. The fused bicyclyl defined herein may be substituted or unsubstituted, wherein the substituents comprise, but are not limited to, oxo (═O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(═O)—, alkyl-C(═O)—, alkyl-S(═O)—, alklyl-S(═O)$_2$—, hydroxy-substituted alkyl-S(═O)—, hydroxy-substituted alkyl-S(═O)$_2$—, carboxy alkoxy, and the like.

The term "fused heterobicyclyl" refers to saturated or unsaturated bridged ring system, which refers to a bicyclic ring system that is not aromatic. Such a system may contain isolated or conjugated unsaturation, but not aromatic or heteroaromatic rings in its core structure (but may have aromatic substitution thereon), wherein at least one ring in the system contains one or more heteroatoms, wherein each ring in the system contains 3 to 7 ring members and that contains one to six carbon atoms and one to three heteroatoms selected from N, O, P, S, wherein the S or P is optionally substituted with one or more oxo to provide the group SO, $SO_2$, PO or $PO_2$, Some non-limiting examples of fused heterobicyclic ring system comprise hexahydro-furo[3.2-b]furan, 7-azabicyclo[2.3.0]heptane, and the like. The fused heterobicyclyl defined herein may be substituted or unsubstituted, wherein the substituents comprise, but are not limited to, oxo (═O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(═O)—, alkyl-C(═O)—, alky-S(═O)—, alkyl-S(═O)$_2$—, hydroxy-substituted alkyl-S(═O)—, hydroxy-substituted alkyl-S(═O)$_2$—, carboxyalkoxy, and the like.

The term "fused bicyclylaliphatic" refers to aliphatic groups substituted with one or more fused bicyclyl groups, wherein the aliphatic group and the fused bicyclyl group are as defined herein. Some non-limiting examples comprise, 1,2,3,4,4a,5,8,8a-octahydro-naphthylethyl, 1,2,3,4,4a,5,8,8a-octahydro-naphthylmethyl, 1,2,3,4,4a,5,8,8a-octahydro-naphthylpropyl, fused bicyclo[3.3.0]octylmethyl, fused bicyclo[3.1.0]hexylethyl, and the like.

The term "fused heterobicyclylaliphatic" refers to aliphatic groups substituted with one or more fused heterobicyclyl groups, wherein the aliphatic group and the fused heterobicyclyl group are as defined herein. Some non-limiting examples comprise hexahydro-furo[3,2-b]furan-2-ylethyl, hexahydro-furo[3,2-b]furan-2-ylmethyl, 7-azabicyclo[2.3.0]hept-2-ylmethyl, 7-azabicyclo[2.3.0]hept-2-yethyl, 7-azabicyclo[2.3.0]hept-4-ylmethyl, and the like.

The term "fused bicycloxy" refers to optionally substituted fused bicyclyl radicals, as defined herein, oxy-containing fused bicyclyl radicals attached through an oxygen atom to other radicals, wherein the fused bicyclyl radical is as defined herein. Some non-limiting examples comprise 1,2,3,4,4a,5,8,8a-octahydro-naphthyloxy, fused bicyclo[3.3.0]oct-2-yloxy, fused bicyclo[3.1.0]hex-2-yloxy, and the like.

The term "fused heterobicycloxy" refers to optionally substituted fused heterobicyclyl radicals, as defined herein, oxy-containing fused heterobicyclyl radicals attached through an oxygen atom to other radicals. Some non-limiting examples comprise hexahydro-furo[3,2-b]furan-2-yloxy, 7-azabicyclo[2.3.0]hept-2-yloxy, 7-azabicyclo[2.3.0]hept-4-yloxy, and the like.

The term "fused bicyclylamino" refers to an amino group substituted with one or two fused bicyclyl groups, wherein the fused bicyclyl group is as defined herein. Some non-limiting examples comprise 1,2,3,4,4a,5,8,8a-octalydronaphthylamino, di(1,2,3,4a,5,8,8a-octahydro-naphthyl) amino, fused bicyclo[3.3.0]octylamino, fused bicyclo[3.1.0] hexylamino, and the like.

The term "fused heterobicyclylalkyamino" refers to alkylamino groups substituted with one or more fused heterobicyclyl groups, wherein the fused heterobicyclyl group as defined herein. Some non-limiting examples comprise hexahydro-furo[3,2-b]furan-2-ylmethylamino, 7-azabicyclo [2.3.0]hept-2-ylmethylamino, 7-azabicyclo[2.3.0]hept-4-ylmethylamino, and the like.

The term "fused bicyclylalkoxy" refers to alkoxy groups substituted with one or more fused bicyclyl groups, wherein the fused bicyclyl group is as defined herein. Some non-limiting examples comprise 1,2,3,4,4a,5,8,8a-octahydro-naphthylmethoxy, 1,2,3,4,4a,5,8,8a-octahydro-naphthylethoxy, fused bicyclo[3.3.0]octylethoxy, fused bicyclo [3.1.0]hexylpropoxy, and the like.

The term "fused heterobicyclylalkoxy" refers to alkoxy groups substituted with one or more fused heterobicyclyl group, wherein the alkoxy group and the fused heterobicyclyl group is as defined herein. Some non-limiting examples comprise hexalydro-furo[3,2-b]furan-2-ylpropoxy, 7-azabicyclo[2.2.1]hept-2-ylethoxy, 7-azabicyclo[2.3.0]hept-4-ylpropoxy, hexahydro-furo[3,2-b]furan-2-ylethoxy, 7-azabicyclo[2.3.0]hept-2-ylpropoxy, 7-azabicyclo[2.3.0]hept-4-ylethoxy, and the like.

The term "fused bicycloxyalkoxy" refers to alkoxy groups substituted with one or more fused bicycloxy groups, wherein the alkoxy group and the fused bicycloxy group are as defined herein. Some non-limiting examples comprise 1,2,3,4,4a,5,8,8a-octahydro-naphthyloxymethoxy, 1,2,3,4,4a,5,8,8a-octahydro-naphthyloxymethoxy, 1,2,3,4,4a,5,8,8a-octahydro-naphthyloxyethoxy, fused bicyclo[3.3.0]oct-2-yloxyethoxy, fused bicyclo[3.1.0]hex-2-yloxypropoxy, and the like.

The term "fused heterobicycloxyalkoxy" refers to alkoxy groups substituted with one or more fused heterobicycloxy groups, wherein the alkoxy group and the fused hecrobicyclyl group is as defined herein. Some non-limiting examples comprise hexahydro-furo[3,2-b]furan 2-yloxypropoxy, 7-azabicyclo[2.2.1]hept-2-yloxyethoxy, 7-azabicyclo[2.3.0] hept-4-yloxypropoxy, hexahydro-furo[3,2-b]furan-2-yloxyethoxy, 7-azabicyclo[2.3.0]hept-4-yloxypropoxy, 7-azabicyclo[2.3.0]hept-4-yloxyethoxy, and the like.

The term "fused bicyclylaminoalkoxy" refers to alkoxy groups substituted with one or more fused bicyclylamino groups, wherein the alkoxy group and the fused bicyclylamino group are as defined herein. Some non-limiting examples comprise 1,2,3,4,4a,5,8,8a-octahydro-naphthylaminoethoxy, 1,2,3,4,4a,5,8,8a-octahydro-naphthylaminopropoxy, di(1,2,3,4,4a,5,8,8a-octahydro-naphthylaminopropoxy, fused bicyclo[3.3.0]oct-2-ylaminoethoxy, fused bicyclo[3.1.0]hex-2-ylaminopropoxy, and the like.

The term "fused heterobicyclylaminoalkoxy" refers to alkoxy groups substituted with one or more fused heterobicyclylamino groups, wherein the alkoxy group and the fused heterobicyclylamino group are as defined herein. Some non-limiting examples comprise 7-azabicyclo[2.2.1]hept-2-ylaminoethoxy, 7-azabicyclo[2.3.0]hept-4-ylaminopropoxy, hexahydro-furo[3,2-b]furan-2-ylaminoethoxy, hexahydro-furo[3,2-b]furan-2-ylaminopropoxy, hexahydro-furo[3,2-b] furan-2-ylaminomethoxy, and the like.

The term "spirocycyl", "spirocyclic", "spiro bicyclyl" or "spiro bicyclic" refers to a ring originating from a particular annular carbon of another ring. For example, as depicted below, a saturated bridged ring system (ring B and B') is termed as "fused bicyclic", whereas ring A and ring B share an atom between the two saturated ring system, which terms as a "spirocyclyl" or "spiro bicyclyl". Each cyclic ring in the spirocyclyl or spiro bicyclyl can be either a carbocyclic or a heteroalicyclic. Some non-limiting examples comprise 2,7-diaza-spiro[4.4]non-2-yl, 7-oxo-2-azaspiro[4.5]dec-2-yl, 4-azaspiro[2.4]hept-5-yl, 4-oxaspiro[2.4]hept-5-yl, 5-azaspiro[2.4]hept-5-yl, spiro[2.4]heptyl, spiro[4.4]nonyl, 7-hydroxy-5-azaspiro[2.4]hept-5-yl, and the like. The spirocyclyl or spirobicyclyl can be optionally substituted, wherein the substituents can be, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxysubstitute alkoxy, hydroxy-substituted alkyl-C(=O), alkyl-C(=O)—, alkyl-S(=O)—, alkyl-S(=O)$_2$, hydroxy-substituted alkyl-S(=O)—, hydroxy-substituted alkyl-S(=O)$_2$—, carboxy alkoxy, and the like.

The term "spiro heterobicyclyl" refers to a ring originating from a particular annular carbon of another ring. For example, as depicted above, a saturated bridged ring system (ring B and B') is termed as "fused bicyclic", whereas ring A and ring B share an carbon atom between the two saturated ring system, which terms as a "spirocyclyl" or "spiro bicyclyl". In addition, at least one ring in the system contains one or more heteroatoms, wherein each ring in the system contains 3 to 7 ring members and that contains one to six carbon atoms and one to three heteroatoms selected from N, O, P, S, wherein the S or P is optionally substituted with one or more oxo to provide the group SO, $SO_2$, PO or $PO_2$. Some non-limiting examples of spiro heterobicyclic ring system comprise 4-azaspiro[2.4]hept-5-yl, 4-oxaspiro [2.4]hept-5-yl, 5-azaspiro[2.4]hept-5-yl, 7-hydroxy-5-azaspiro[2.4]hept-5-yl, and the like. The spiro heterobicyclyl defined herein may be substituted or unsubstituted, wherein the substituents comprise, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alklyl-C(=O)—, alkyl-C(=O)—, alkyl-S(=O)—, alkyl (S=O)$_2$—, hydroxy-substituted alkyl-S(=O)—, hydroxy-subtituted alkyl-S(=O)$_2$, carboxyalkoxy, and the like.

The term "spiro bicyclylaliphatic" refers to aliphatic groups substituted with one or more spiro bicyclyl groups, wherein the aliphatic group and the spiro bicyclyl group are as defined herein. Some non-limiting examples comprise spiro[2.4]heptylmethyl, spiro[2.4]heptylethyl, spiro[2.4] heptylpropyl, spiro[4.4]nonylmethyl, spiro[4.4]nonylethyl, 4-azaspiro[2.4]hept-5-yl-methyl, 4-azaspiro[2.4]hept-5-yl-ethyl, 4-oxaspiro[2.4]hept-5-yl-ethyl, 5-azaspiro[2.4]hept-5-yl-propyl, 7-hydroxy-5-azaspiro[2.4]hept-5-yl-propyl, and the like.

The term "spiro heterobicyclylaliphatic" refers to aliphatic groups substituted with one or more spiro heterobicyclyl groups, wherein the aliphatic group and the fused heterobicyclyl group are as defined herein. Some non-limiting examples comprise 4-azaspiro[2.4]hept-5-yl-methyl, 4-azaspiro[2.4]hept-5-yl-ethyl, 4-oxaspiro[2.4]hept-5-ethyl, 5-azaspiro[2.4]hept-5-yl-propyl, 7-hydroxy-5-azaspiro[2.4]hept-5-yl-propyl, and the like.

The term "spiro bicycloxy" comprises optionally substituted spiro bicyclyl radicals, as defined herein, attached to an oxygen atom, and the spiro bicycloxy is attached to other radicals through the oxygen atom. Some non-limiting examples comprise spiro[2.4]heptyl-2-oxy, spiro[2.4]heptyl-3-oxy, spiro[2.4]hepty-4-oxy, spiro[4.4]nonyl-2-oxy, spiro[4.4]nonyl-4-oxy, 4-azaspiro[2.4]hept-5-oxy, and the like.

The term "spiro heterobicycloxy" comprises optionally substituted spiro heterobicyclyl radicals, as defined herein, attached to an oxygen atom, and the spiro heterobicycloxy is attached to other radicals through the oxygen atom. Some non-limiting examples comprise 4-azaspiro[2.4]hept-5-yloxy, 4-oxaspiro[2.4]hept-5-yloxy, 5-azaspiro[2.4]hept-5-yloxy, and the like.

The term "spiro bicyclylamino" refers to an amino group substituted with one or two spiro bicyclyl groups, wherein the spiro bicyclyl group is as defined herein. Some non-limiting examples comprise spiro[2.4]heptyl-2-amino, spiro[2.4]heptyl-3-amino, spiro[2.4]heptyl-4-amino, spiro[4.4]nonyl-2-amino, spiro[4.4]nonyl-4-amino, 4-azaspiro[2.4]hept-5-amino, and the like.

The term "spiro heterobicyclylamino" refers to an amino group substituted with one or two spiro heterobicyclyl groups, wherein the spiro heterobicyclyl group is as defined herein. Some non-limiting examples comprise 4-azaspiro[2.4]hept-5-ylamino, 4-oxaspiro[2.4]hept-2-ylamino, 4-oxaspiro[2.4]hept-5-ylamino, 5-azaspiro[2.4]hept-5-ylamino, and the like.

The term "spiro bicyclylalkoxy" refers to alkoxy groups substituted with one or more spiro bicyclyl groups, wherein the spiro bicyclyl group is as defined herein. Some non-limiting examples comprise spiro[2.4]heptyl-2-methoxy, spiro[2.4]heptyl-3-ethoxy, spiro[2.4]heptyl-4-ethoxy, spiro[4.4]nonyl-2-methoxy, spiro[4.4]nonyl-4-propoxy, 4-azaspiro[2.4]hept-5-methoxy, and the like.

The term "spiro heterobicyclylalkoxy" refers to alkoxy groups substituted with one or more spiro heterobicyclyl groups, wherein the spiro heterobicyclyl group is as defined herein. Some non-limiting examples comprise 4-azaspiro[2.4]hept-5-yl-methoxy, 4-azaspiro[2.4]hept-2-yl-ethoxy, 4-oxaspiro[2.4]hept-5-yl-ethoxy, 5-azaspiro[2.4]hept-5-yl-propoxy, and the like.

The term "spiro bicyclylalkyamino" refers to alkylamino groups substituted with one or more spiro bicyclyl groups, wherein the spiro bicyclyl group is as defined herein. Some non-limiting examples comprise spiro[2.4]heptyl-2-methylamino, spiro[2.4]heptyl-3-ethylamino, spiro[2.4]heptyl-4-ethylamino, spiro[4.4]nonyl-2-methylamino, spiro[4.4]nonyl-4-propylamino, 4-azaspiro[2.4]hept-5-methylamino, and the like.

The term "spiro heterobicyclylalkyamino" refers to alkylamino groups substituted with one or more spiro heterobicyclyl groups, wherein the spiro heterobicyclyl group is as defined herein. Some non-limiting examples comprise 4-azaspiro[2.4]hept-5-yl-methylamino, 4-azaspiro[2.4]hept-2-yl-ethylamino, 4-oxaspiro[2.4]hept-5-yl-ethylamino, 5-azaspiro[2.4]hept-5-yl-propylamino, and the like.

The term "spiro bicycloxyalkoxy" refers to alkoxy groups substituted with one or more spiro bicycloxy groups, wherein the alkoxy group and the spiro bicyclyl group are as defined herein. Some non-limiting examples comprise spiro[2.4]heptyl-2-oxyethoxy, spiro[2.4]heptyl-3-oxypropoxy, spiro[2.4]heptyl-4-oxypropoxy, spiro[4.4]nonyl-2-oxyethoxy, spiro[4.4]nonyl-4-oxypropoxy, 4-azaspiro[2.4]hept-5-oxypropoxy, and the like.

The term "spiro heterobicycloxyalkoxy" refers to alkoxy groups substituted with one or more spiro heterobicycloxy groups, wherein the alkoxy group and the spiro heterobicyclyl group are as defined herein. Some non-limiting examples comprise 4-azaspiro[2.4]hept-5-yloxyethoxy, 4-oxaspiro[2.4]hept-5-yloxyethoxy, 5-azaspiro[2.4]hept-5-yloxyethoxy, 4-azaspiro[2.4]hept-5-yloxypropoxy, 4-oxaspiro[2.4]hept-5-yloxypropoxy, 5-azaspiro[2.4]hept-5-yloxypropoxy, and the like.

The term "spiro bicyclylaminoalkoxy" refers to alkoxy groups substituted with one or more spiro bicyclylamino groups, wherein the alkoxy group and the spiro bicyclylamino group are as defined herein Some non-limiting examples comprise spiro[2.4]heptyl-2-aminoethoxy, spiro[2.4]heptyl-3-aminopropoxy, spiro[2.4]heptyl-4-aminoethoxy, spiro[4.4]nonyl-2-aminoethoxy, spiro[4.4]nonyl-4-aminopropoxy, 4-azaspiro[2.4]hept-5-aminopropoxy, and the like.

The term "spiro heterobicyclylaminoalkoxy" refers to alkoxy groups substituted with one or more spiro heterobicyclylamino groups, wherein the alkoxy group and the spiro heterobicyclylamino group are as defined herein. Some non-limiting examples comprise 4-azaspiro[2.4]hept-5-ylaminoethoxy, 4-oxaspiro[2.4]hept-2-ylaminopropoxy, 4-oxaspiro[2.4]hept-5-ylaminoethoxy, 5-azaspiro[2.4]hept-5-ylaminopropoxy, and the like.

The term "protecting group" or "PG" refers to the reaction of a substituent with other functional groups, which is usually used to block or protect special functions. For example, "amino protecting group" refers to a substituent group connected with an amino group to block or protect the functionality of the amino group in a compound. Suitable amino protecting groups include acetyl group, trifluoroacetyl group, tert-butoxycarbonyl group (BOC, Boc), benzyloxycarbonyl group (CBZ, Cbz) and 9-fluorenylmethyleneoxycarbonyl group (Fmoc). Similarly, "hydroxyl protecting group" refers to the substituent of hydroxyl group used to block or protect the functionality of hydroxyl group. Suitable protecting groups include acetyl group and methylsilyl group. "Carboxyl protecting group" refers to the substituent of carboxyl group used to block or protect the functionality of carboxyl group. General carboxyl protecting groups include $—CH_2CH_2SO_2Ph$, cyanoethyl, 2-(trimethylsilyl)ethyl, 2-(trimethylsilyl) ethoxymethyl, 2-(p-toluenesulfonyl)ethyl, 2-(p-nitrobenzenesulfonyl)ethyl, 2-(diphenylphosphino) ethyl and nitroethyl, and the like. For the general description of protective groups, please refer to T W. Greene, Protective Groups in Organic Synthesis, John Wiley & Sons, New York, 1991; and P. J. Kocienski, Protecting Groups, Thieme, Stuttgart, 2005.

The term "prodrug" refers to a compound that is transformed in vivo into a compound of Formula I. Such a transformation can be affected by hydrolysis in blood or enzymatic transformation of the prodrug form to the parent form in blood or tissue. Prodrugs of the compounds disclosed herein may be, for example, esters. Esters that may be utilized as prodrugs in the present disclosure are phenyl esters, aliphatic ($C_1$-$C_{24}$) esters, acyloxymethyl esters, carbonates, carbamates, and amino acid esters. For example, a compound disclosed herein that contains a hydroxyl group, may be acylated to provide a compound of prodrug form. Other prodrug forms comprise phosphates. For example, these phosphates are obtained from the phosphorylation of a hydroxyl group in the parent compound. A thorough discussion of prodrugs is provided in T. Higuchi and V. Stella, Pro-drugs as Novel Delivery Systems, Vol. 14 of the A.C.S. Symposium Series. Edward B. Roche, ed., Bioreversible Carriers in Drug Design, American Pharmaceutical Association and Pergamon Press, 1987, J. Rautio et al, Prodrugs: Design and Clinical Applications. *Nature Review Drug Discovery,* 2008, 7, 255-270, and S. J. Hecker et al, Prodrugs of Phosphates and Phosphonates, *Journal of Medicinal Chemistry,* 2008, 51, 2328-2345, all of which are incorporated herein by reference.

The term "metabolite" refers to the product obtained by the metabolism of a specific compound or the salt thereof in vivo. A metabolite of a compound can be identified by a well-known technique in the art, and its activity can be characterized by an experimental method as described herein. Such products can be obtained by oxidation, reduction, esterification, hydrolysis, degreasing, enzymatic hydrolysis, amidation and/or deamidation of the compound. Accordingly, the disclosure includes metabolites of compounds, comprising metabolites produced by full contact of the compounds disclosed herein with mammals for a period of time.

A "pharmaceutically acceptable salts" used in the present disclosure refer to organic or inorganic salts of a compound disclosed herein pharmaceutically acceptable salts are well known in the art. For example, S. M. Berge et al. describe pharmaceutically acceptable salts in detail in *J. Pharmaceutical Sciences,* 1977, 66:1-19, which is incorporated herein by reference. The pharmaceutically acceptable and nontoxic salts comprise, but are not limited to the inorganic acid salts formed by the reactions with an amino group, such as hydrochloride, hydrobromide, phosphate, sulfate and perchlorate, and organic acid salts, such as acetates, oxalates, maleates, tartrates, citrates, succinates, and malonate, or the salts obtained by other methods used in the literatures, such as ion exchange. Other pharmaceutically acceptable salts comprise adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases comprise alkali metal, alkaline earth metal, ammonium and $N^+(C_{1-4}\ alkyl)_4$ salts. This disclosure also envisions the quaternization of any basic nitrogen-containing groups of the compounds disclosed herein. Water- or oil-soluble or dispersable products may be obtained by such quaternization. Representative alkali or alkaline earth metal salts comprise sodium, lithium, potassium, calcium, magnesium, and the like. Pharmaceutically acceptable salts further comprise, appropriate and nontoxic ammonium, quaternary ammonium, and ammonium cations formed using counterions such as halide, hydroxide, carboxylate, sulfate, phosphate, nitrate, $C_{1-8}$ sulfonate or aryl sulfonate.

A "solvate" in the present disclosure refers to a complex formed by one or more solvent molecules with a compound disclosed herein. The solvents that form solvates comprise, but are not limited to water, isopropanol, ethanol, methanol, dimethyl sulfoxide, ethyl acetate, acetic acid and ethanolamin. The term "hydrate" refers to the complex wherein the solvent molecule is water.

When the solvent is water, the term "hydrate" may be used. In some embodiments, a compound disclosed herein may be combined with a water molecule, such as a hydrate. In other embodiments, a compound disclosed herein can be combined with more than one water molecule, such as dehydrate. In some embodiments, a compound molecule disclosed herein can be combined with less than one water molecule, such as hemihydrate. It should be noted that the hydrate described in the disclosure retains the bioavailability of the compound in a non-hydrated form.

The term "solubility" refers to the mass of solute dissolved when a solid substance reaches saturation state in 100 g solvent at a certain temperature. Solubility test refer to the following references: ZHU Shang-bin, et al. Preparation, characterization, and physicochemical properties of arbutin phospholipid complex [J]. Chinese Traditional and Herbal Drugs. 2020, 1-10.

The term "acute toxicity" refers to the toxic effect or even death caused by the body (human or experimental animal) once (or several times within 24 hours) exposed to foreign compounds. However, it should be pointed out that the speed and intensity of toxic effects of compounds on experimental animals may vary with the quality and quantity of the compounds. Some compounds can cause poisoning symptoms or even death within a few minutes of exposure to lethal dose. Some compounds showed poisoning symptoms and death only after a few days, that is, delayed death. In addition, the meaning of "once" varies according to the way or route of exposure of experimental animals. For oral contact and injection contact in various ways, "once" refers to the instantaneous injection of the tested compound into the body of the experimental animal. The "once" refers to the process that the experimental animals continuously contact with the tested compounds in a specific period of time, so the "once" contains the time factor.

The term "treatment" of any disease or disorder refers to all conditions that can slow, interrupt, prevent, control or stop the progress of the disease or disorder, but does not necessarily mean that all symptoms of the disease or disorder have disappeared, and it also includes preventive treatment of the symptoms, especially in patients prone to such disease or disorder. In some embodiments, it means a disease or condition improved (i.e., slowing or preventing or alleviating the development of a disease or at least one of its clinical symptoms). In other embodiments, "treatment" refers to the alleviation or improvement of at least one body parameter, including a body parameter that may not be perceived by the patient. In other embodiments, "treatment" refers to the regulation of a disease or condition from a physical (e.g., stabilizing perceptible symptoms) or physiological (e.g., stabilizing body parameters) or both. In other embodiments, "treatment" means preventing or delaying the onset, occurrence, or deterioration of a disease or condition.

The term "therapeutically effective dose" refers to the amount of the compound disclosed herein capable of eliciting a biological or medical response of an individual (e.g., reducing or inhibiting enzyme or protein activity, or improving symptoms, alleviating symptoms, slowing or delaying disease progression, or preventing disease, and the like). In a non-limiting embodiment, the term "therapeutically effective dose" refers to the amount that, when administered to an individual, is effective for: (1) at least partially alleviating, inhibiting, preventing and/or improving tumor proliferation. In other embodiments, the term "therapeutically effective dose" refers to the amount of an effective compound disclosed herein capable of at least partially reducing or inhibiting tumor proliferation when administered to a cell, or organ, or non-cellular biological substance, or medium.

The terms "give" and "administer" compound shall be understood as providing a compound disclosed herein or a prodrug of a compound disclosed herein for an individual in need thereof. It should be appreciated that those skilled in the art can have an impact on tumor proliferation by using an effective amount of the disclosed compound to treat a patient currently suffering from the disorder or to prophylactically treat a patient suffering from the disorder.

The term "composition" refers to a product containing a prescribed amount of prescribed ingredients, and any product produced directly or indirectly by a combination of prescribed amounts of prescribed ingredients. The meaning of this term related to pharmaceutical compositions includes products containing active ingredients (single or multiple) and inert ingredients (single or multiple) that make up the carrier, as well as mixtures, combinations or aggregations of any two or more ingredients, or decomposition of one or more ingredients, or any product produced directly or indirectly by other types of reactions or interactions of one or more components. Accordingly, the pharmaceutical compositions disclosed herein include any compositions prepared by mixing the compounds disclosed herein with a pharmaceutical carrier.

The compounds disclosed in the present disclosure may contain asymmetric or chiral centers, and therefore may exist in different stereoisomeric forms. The present disclosure aims to make all stereoisomeric forms of the compound represented by Formula (I), including but not limited to diastereomers, enantiomers, atropisomers and geometric (or conformational) isomers and their mixtures, such as racemic mixtures, become an integral part of the present disclosure.

In the structure disclosed in the present disclosure, when the stereochemistry of any specific chiral atom is not specified, all stereoisomers of the structure are considered in the present disclosure and are included in the present disclosure as the compound disclosed in the present disclosure in. When stereochemistry is indicated by a solid wedge or dashed line representing a specific configuration, then the stereoisomer of the structure is clear and defined.

The compound represented by Formula (I) may exist in different tautomeric forms, and all these tautomers are included in the scope of the present disclosure.

The compound represented by Formula (I) may exist in the form of a salt. In some embodiments, the salt refers to a pharmaceutically acceptable salt. The term "pharmaceutically acceptable" means that a substance or composition must be chemically and/or toxicologically compatible with other ingredients containing the product and/or with the mammals in which it is treated. In other embodiments, the salt may not necessarily be pharmaceutically acceptable salts and may be an intermediate used for the preparation and/or purification of the compound represented by Formula (I) and/or for the separation of the enantiomers of the compound represented by Formula (I).

Pharmaceutically acid addition salts may be formed by the reaction of the disclosed compounds with inorganic or organic acids, such as acetic acid salt, aspartate, benzoic acid salt, benzene sulfonate salt, bromide/hydrobromide, bicarbonate/carbonate, hydrogen sulfate salt/sulfate, camphor sulfonic acid salt, chloride/hydrochloride salt, chlorine theophylline salt, citric acid salt, ethanedisulphonate, fumaric acid salt salt, portuguese heptanoic acid salt, gluconic acid salt, sugar glucuronic acid salt, hippuric acid salt, hydroiodic acid salt/iodide, hydroxyethyl sulfonic acid salt, lactic acid salt, lactobionic aci salt, lauryl sulfate salt, malic acid salt, maleic acid salt, malonate, mandelic acid salt, mesilate, methyl sulfate salt, naphthalene formate, naphthalene sulfonate, nicotinic acid salt, nitrate, stearic acid salt, oleic acid salt, oxalic acid salt, hexadecanoic acid salt, embonate, phosphate/hydrogen phosphate salt/dihydrogen phosphate salt, poly-galactose acid salt, propionic acid salt, stearic acid salt, succinate, sulfosalicylate, tartrate, toluene sulfonate and trifluoroacetate.

Pharmaceutically alkali addition salts may be formed by the reaction of the disclosed compounds with an inorganic base or an organic base.

Inorganic bases from which salts can be derived include, for example, ammonium salts and metals of group I to group XII of the periodic table. In some embodiments, the salt is derived from sodium, potassium, ammonium, calcium, magnesium, iron, silver, zinc and copper; Particularly suitable salts include ammonium, potassium, sodium, calcium, and magnesium salts.

Organic bases derived from them include primary amines, secondary amines and tertiary amines, and substituted amines include naturally occurring substituted amines, cyclic amines, basic ion exchange resins, etc. Some organic amines include, for example, isopropylamine, benzathine, cholinate, diethanolamine, diethylamine, lysine, meglumine, piperazine, and ambutriol.

The pharmaceutically acceptable salts of the present disclosure can be synthesized from the parent compound, basic or acidic moieties using conventional chemical methods. Generally speaking, such salts can be prepared by reacting the free acid form of these compounds with a stoichiometric amount of a suitable base (such as hydroxide, carbonate, bicarbonate of Na, Ca, Mg or K, and the like) or by reacting the free base form of these compounds with a stoichiometric amount of a suitable acid. The type of reaction is usually carried out in water or an organic solvent or a mixture of the two. Generally, when appropriate, it is necessary to use a non-aqueous medium such as diethyl ether, ethyl acetate, ethanol, isopropanol, or acetonitrile. For example, "*Remington's Pharmaceutical Sciences*", $20^{th}$ Version, Mack Publishing Company, Easton, Pa., (1985); and "*Handbook of Pharmaceutical Salts: Properties, Selection, and Use*", a list of other suitable salts can be found in Stahl and Wermuth (Wiley-VCH, Weinheim, Germany, 2002).

In addition, the compounds disclosed in the present disclosure, including their salts, can be also obtained in the form of their hydrates or in the form of containing their solvents (for example, ethanol or DMSO, and the like), and used for their crystallization. The compounds disclosed in the present disclosure may form solvates inherently or by design with pharmaceutically acceptable solvents (including water); therefore, the present disclosure is intended to include both solvated and unsolvated forms of the compounds disclosed in the present disclosure.

Any structural formula given in the present disclosure is also intended to represent the non-isotopically enriched form and the isotopically enriched form of these compounds. The isotope-enriched compound has the structure depicted by the general formula given in this disclosure, except that one or more atoms are replaced by atoms having the selected atomic weight or mass number. Exemplary isotopes that can be introduced into the compounds of the present disclosure include isotopes of hydrogen, carbon, nitrogen, oxygen, phosphorus, sulfur, fluorine, and chlorine, such as $^{2}H$, $^{3}H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$ and $^{125}I$.

On the other hand, the compounds described in the present disclosure include isotopically enriched compounds defined in the present disclosure, for example, those compounds in which radioisotopes such as $^{3}H$, $^{14}C$, and $^{18}F$ are present, or those in which non-radioactive isotopes such as $^{2}H$ and $^{13}C$. Compounds enriched in this type of isotope can be used for metabolism studies (using $^{14}C$), reaction kinetics studies (using, for example, $^{2}H$ or $^{3}H$), detection or imaging techniques, such as positron emission tomography (PET), or tissues including drugs or substrates single-photon emission computed tomography (SPECT), which is used for distribution measurement, may be used in radiotherapy of patients. Compounds enriched in $^{18}F$ are particularly ideal for PET or SPECT research. The isotope-enriched compound represented by Formula (I) can be prepared by conventional techniques familiar to those skilled in the art or as described in the examples and preparation procedures in this disclosure, using a suitable isotope-labeled reagent instead of the previously used unlabeled reagent.

In addition, the substitution of heavier isotopes, particularly deuterium (i.e., $^2H$ or D), can provide certain therapeutic advantages due to higher metabolic stability. For example, increased half-life in vivo or decreased dosage requirements or improved therapeutic index. It should be appreciated that deuterium in the present disclosure is regarded as a substituent of the compound represented by Formula (I). The isotope enrichment factor can be used to define the concentration of such heavier isotopes, especially deuterium. The term "isotopic enrichment factor" as used in the present disclosure refers to the ratio between the isotopic abundance and the natural abundance of the specific isotope. If the substituent of the compound of the present disclosure is designated as deuterium, the compound has at least 3500 (52.5% deuterium incorporation at each designated deuterium atom), at least 4000 (60% deuterium incorporation), for each designated deuterium atom, At least 4500 (67.5% deuterium doping), at least 5000 (75% deuterium doping), at least 5500 (82.5% deuterium doping), at least 6000 (90% deuterium doping), at least 6333.3 (95% deuterium doping) Deuterium incorporation), at least 6466.7 (97% deuterium incorporation), at least 6600 (99% deuterium incorporation), or at least 6633.3 (99.5% deuterium incorporation) isotope enrichment factor. Pharmaceutically acceptable solvates of the present disclosure include those in which the crystallization solvent may be isotopically substituted, such as $D_2O$, acetone-$d_6$, and/or DMSO-$d_6$.

On the other hand, the disclosure provides a pharmaceutically acceptable composition that contains the disclosed compounds. In some embodiments, the pharmaceutically acceptable compositions further include a pharmaceutically acceptable carrier, excipient, adjuvant, solvent or a combination thereof. In other embodiments, the pharmaceutically acceptable composition may be in liquid, solid, semisolid, gel or aerosol form.

Pharmaceutical Compositions, Formulations and Administration

The pharmaceutically acceptable compositions of the present disclosure further comprise a pharmaceutically acceptable carrier, excipient, or excipient, which may be in liquid, solid, semi-solid, gel, or spray dosage form.

The disclosure provides a pharmaceutically acceptable composition, containing compounds disclosed in this disclosure, such as those listed in examples; and pharmaceutically acceptable excipients, carriers, adjuvants, solvents or combinations thereof.

The disclosure provides methods for treating, preventing or improving a disease or disorder, including administering a safe and effective amount of a combination drug comprising a compound disclosed in the present disclosure and one or more therapeutic active agents. Among them, the combination drugs include one or more drugs for the prevention or treatment of liver cancer, leukemia, breast cancer, colon adenocarcinoma, gastric cancer, lung cancer, Bart's esophageal cancer, cervical cancer, pancreatic cancer, endometrial cancer, bone cancer, lymphoma, kidney cancer, brain cancer, nerve cancer, nasopharyngeal cancer, oral cancer and colorectal cancer. The active ingredient of the drug is different from the compound disclosed herein.

Drugs for the prevention or treatment of liver cancer, leukemia, breast cancer, colon adenocarcinoma, gastric cancer, lung cancer, Bart's esophageal cancer, cervical cancer, pancreatic cancer, endometrial cancer, bone cancer, lymphoma, kidney cancer, brain cancer, nerve cancer, nasopharyngeal cancer, oral cancer and colorectal cancer include but are not limited to: aromatase inhibitors, topoisomerase I inhibitors, topoisomerase II inhibitors, microtubule activators, alkylating agent, histone deacetylase inhibitors, compounds that induce cell differentiation, cyclooxygenase inhibitors, MMP inhibitors, Mtor inhibitors, anti-tumor and anti-metabolic drugs, platinum compounds, compounds that target/reduce protein or lipid phosphokinase activity and other anti-vascular production compounds, anti-proliferative antibodies, heparanase inhibitors, Ras carcinogenic inhibitors, telomerase inhibitors, proteasome inhibitors or any combination of them.

The dose of the active component in the disclosed composition can be changed, but the amount of the active component must be the amount in which the appropriate dosage form can be obtained. The active components can be administered to patients (animals and people) in need of such treatment at doses that provide the best drug efficacy. The dosage chosen depends on the desired therapeutic effect, the route of administration and the duration of treatment. The dose will vary with the patient, depending on the nature and severity of the disease, the patient's weight, the patient's specific diet, the drugs used at the same time, and other factors that will be recognized by those skilled in the art. The dosage range is usually about 0.5 mg to 1.0 g per patient per day, which can be given in single or multiple doses. In one embodiment, the dose ranges from about 0.5 mg to 500 mg per patient per day. In another embodiment, about 0.5 mg to 200 mg every patient per day. In another embodiment, about 5 mg to 50 mg per day for each patient.

It should be also recognized that certain compounds of the present disclosure may exist in free form for therapeutic use or, if appropriate, in the form of their pharmaceutically acceptable derivatives. Pharmaceutically acceptable derivatives include pharmaceutically acceptable prodrugs, salts, esters and salts of these esters, or any other adducts or derivatives that can directly or indirectly provide the compounds or metabolites or residues of the present disclosure when administered to patients in need.

The medicine or pharmaceutical composition disclosed in the present disclosure can be prepared and packaged in bulk form, in which a safe and effective amount of compound represented by Formula (I) can be extracted and then given to the patient in the form of powder or syrup. In general, patients are given doses ranging from 0.0001 to 10 mg/kg body weight per day to achieve an effective effect. Alternatively, the pharmaceutical composition disclosed in the present disclosure can be prepared and packaged as a unit dosage form, in which each physically discrete unit contains a safe and effective amount of the compound represented by Formula (I). When prepared in a unit dosage form, the pharmaceutical compositions disclosed in the present disclosure can generally contain, for example, 0.5 mg to 1 g, or 1 mg to 700 mg, or 5 mg to 100 mg of the compounds disclosed in the present disclosure.

When the pharmaceutical composition of the present disclosure contains one or more other active components in addition to the compounds of the present disclosure, the weight ratio of the compounds of the present disclosure to the second active component may vary and depend on the effective dose of each component. Usually, the effective dose of each is used. Therefore, for example, when a compound of the present disclosure is mixed with another agent, the weight ratio of the compound of the present disclosure to another agent usually ranges from about 1000:1 to about 1:1000, for example, from about 200:1 to about 1:200. Mixtures of the compounds of the present disclosure with other active components are generally within the above range, but in each case an effective dose of each active component should be used.

"Pharmaceutically acceptable excipient" as used in the present disclosure means a pharmaceutically acceptable material, mixture or solvent related to the consistency of the dosage form or pharmaceutical composition. Each excipient must be compatible with other components of the pharmaceutical composition when mixed, so as to avoid interactions that will greatly reduce the efficacy of the compounds disclosed in the present disclosure and lead to interactions that are not pharmaceutically acceptable pharmaceutical compositions when administered to patients. In addition, each excipient must be pharmaceutically acceptable, for example, of sufficiently high purity.

The appropriate pharmaceutically acceptable excipients will vary according to the specific dosage form selected. In addition, pharmaceutically acceptable excipients can be selected according to their specific functions in the composition. For example, certain pharmaceutically acceptable excipients that can contribute to the production of uniform dosage forms may be selected. Some pharmaceutically acceptable excipients that can contribute to the production of stabilizer type can be selected. Certain pharmaceutically acceptable excipients that assist in carrying or transporting the disclosed compounds from one organ or part of the body to another organ or part of the body when administered to a patient may be selected. Some pharmaceutically acceptable excipients can be selected to enhance patient compliance.

Suitable pharmaceutically acceptable excipients include the following types of excipients: diluents, fillers, adhesives, disintegrating agents, lubricants, flow aids, granulating agents, coating agents, wetting agents, solvents, cosolvents, suspension aids, emulsifiers, sweeteners, flavor correctors, taste masking agents, colorants, anti-caking agents, humectants, chelators, plasticizers, tackifiers, antioxidants preservatives, stabilizers, surfactants and buffers. Technicians may recognize that some pharmaceutically acceptable excipients can provide more than one function and provide alternative functions, depending on how much of the excipient is present in the preparation and what other excipients are present in the preparation.

Those skilled in the art have the knowledge and skills to enable them to select an appropriate amount of a suitable pharmaceutically acceptable excipient for use in the present disclosure. In addition, there are a large number of resources available to technicians who describe pharmaceutically acceptable excipients and use them to select appropriate pharmaceutically acceptable excipients. Examples include Remington's Pharmaceutical Sciences (Mack publishing company), the Handbook of pharmaceutical additions (Gower Publishing Limited), and the Handbook of pharmaceutical exceptions (the American Pharmaceutical Association and the pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, various carriers used for the preparation of pharmaceutically acceptable compositions and the publicly known techniques used for their preparation are disclosed, and the respective contents of these literatures are incorporated into this disclosure by citation. Its use is covered by the scope of this disclosure except for any conventional carrier medium that is incompatible with the disclosed compound, such as producing any adverse biological effects or otherwise interacting in a harmful manner with any other component of a pharmaceutically acceptable composition.

The pharmaceutical composition disclosed in the present disclosure is prepared using techniques and methods known to those skilled in the art. For the description of some common methods in the art, please refer to Remington's Pharmaceutical Sciences (Mack publishing company).

Therefore, on the other hand, the present disclosure relates to a process for preparing a pharmaceutical composition comprising a compound disclosed in the present disclosure and a pharmaceutically acceptable excipient, carrier, adjuvant, solvent or a combination thereof, and the process comprising a mixture of various ingredients. The pharmaceutical compositions containing the compound disclosed in the present disclosure may be prepared by mixing at, for example, at ambient temperature and atmospheric pressure.

The compounds disclosed in the present disclosure are generally formulated into a dosage form suitable for administration to patients through a desired route. For example, dosage forms include those suitable for the following routes of administration: (1) Oral administration, such as tablets, capsules, lozenges, pills, capsetst, powders, syrups, elixirs, suspensions, solutions, emulsions, sachets and cachets; (2) Parenteral administration, such as sterile solutions, suspensions and reconstituted powders; (3) Transdermal administration, such as transdermal patches; (4) Rectal administration, such as suppositories; (5) Inhalation, such as aerosols, solutions and dry powders; (6) Topical administration, such as ointments, lotions, creams, solutions, sprays, pastes, foams and gels.

In some embodiments, the compounds disclosed herein can be formulated into oral dosage forms. In some embodiments, the compounds disclosed herein can be formulated into inhaled dosage forms. In some other embodiments, the compounds disclosed herein can be formulated for transnasal dosage forms. In some other embodiments, the compounds disclosed herein can be formulated for transdermal dosage forms. In some embodiments, the compounds disclosed herein can be formulated into a topical dosage forms.

The pharmaceutical compositions provided herein can be provided as pressed tablet, a manufactured tablet, a chewable spindle, an instant tablet, a multiple compressed tablet, an enteric-coated tablet, icing or film coating. Enteric coated tablet is a kind of pressed tablet coated with substances that can resist gastric acid but dissolve or disintegrate in the intestine, so as to prevent the active ingredients from contacting the acidic environment of the stomach. Intestinal coating includes, but is not limited to, fatty acid, fat, phenyl salicylate, wax, lac, ammoniated lac and cellulose phthalate. The sugar coated tablet is a pressed tablet surrounded by sugar coating, which can help to cover up the unpleasant taste or smell and prevent the tablet from oxidation. The film coated tablet is a thin layer of water-soluble substance or a pressed tablet covered by a film. The film coating includes, but is not limited to, hydroxyethyl cellulose, sodium carboxymethyl cellulose, PEG 4000 and cellulose phthalate acetate. Film coating has the same general characteristics as sugar coating. The compound compression tablet is a compression tablet prepared after more than one compression cycle, including multi-layer tablets compression coated or dry coated tablets.

Tablet formulations may be prepared from active ingredients in powder, crystalline or granular form, individually or in combination with one or more carriers or excipients disclosed herein, including adhesives, disintegrant agents, controlled release polymers, lubricants, diluents and/or colorants. Flavor enhancers and sweeteners are particularly useful in the formation of chewable tablets and pastilles.

The pharmaceutical composition provided by the present disclosure can be provided in soft capsules or hard capsules, which can be prepared from gelatin, methylcellulose, starch or calcium alginate. The hard gelatin capsule, also known as dry filled capsule (DFC), is composed of two sections, one of which is inserted into the other section, thus completely encapsulating the active ingredient. Soft elastic capsules (SEC) are soft spherical shells, such as gelatin shells, which are plasticized by adding glycerol, sorbitol or similar polyols. Soft gelatin shells can contain preservatives to prevent microbial growth. Suitable preservatives are those as described in the present disclosure, including methylparaben and propyl paraben, and sorbic acid. The liquid, semi-solid and solid dosage forms provided by the present disclosure can be encapsulated in capsules. Suitable liquid and semi-solid dosage forms include solutions and suspensions in propylene carbonate, vegetable oil or triglycerides. Capsules containing such a solution may be as described in U.S. patent U.S. Pat. Nos. 4,328,245; 4,409,239 and 4,410,545. The capsule can be also coated as known by those skilled in the art, so as to improve or maintain the dissolution of the active ingredient.

The pharmaceutical compositions provided by the present disclosure can be provided in liquid and semi-solid dosage forms, including emulsions, solutions, suspensions, elixirs and syrups. The emulsion is a two-phase system, in which one liquid is completely dispersed in the other liquid in the form of small balls, which can be oil in water or water in oil. Emulsions may include pharmaceutically acceptable non-aqueous liquids and solvents, emulsifiers and preservatives. Suspensions may include pharmaceutically acceptable suspension aids and preservatives. Aqueous alcohol solutions may include pharmaceutically acceptable acetals, such as di-(lower alkyl)-acetals of lower alkyl aldehydes, such as acetaldehyde diethyl acetals. A water-soluble solvent having one or more hydroxyl groups, such as propylene glycol and ethanol. Elixir is a transparent, sweet water alcohol solution. Syrups are aqueous solutions of concentrated sugars, such as sucrose, and can also contain preservatives. For liquid dosage forms, for example, solutions in polyethylene glycol may be diluted with a sufficient amount of a pharmaceutically acceptable liquid carrier, such as water, for accurate and convenient administration.

Other useful liquid and semi-solid dosage forms include, but are not limited to, those containing the active ingredient provided in the present disclosure and the secondary mono or poly alkylene glycol, which includes: 1,2-dimethoxymethane, diethylene glycol dimethyl ether, triethylene glycol dimethyl ether, tetraethylene glycol dimethyl ether, polyethylene glycol-350-dimethyl ether, polyethylene glycol-550-dimethyl ether PEG-750-dimethyl ether, in which 350, 550 and 750 refer to the approximate average molecular weight of PEG. These preparations may further include one or more antioxidants, such as butylated hydroxytoluene (BHT), butylated hydroxyanisole (BHA), propyl gallate, vitamin E, hydroquinone, hydroxycoumarin, ethanolamine, lecithin, cephalin, ascorbic acid, malic acid, sorbitol, phosphoric acid, bisulfite, sodium pyrosulfite, thiodipropionic acid and its esters, and dithiocarbamates.

As appropriate, the dosage unit of oral administration can be encapsulated in microcapsules. It can be also prepared into compositions that extend or maintain the release, for example by coating or embedding the particulate material in a polymer, wax or similar.

The oral pharmaceutical composition provided by the present disclosure can be also provided in the form of liposomes, micelles, microspheres or nanosystems. Micellar formulations can be prepared by the method described in U.S. Pat. No. 6,350,458.

The pharmaceutical compositions provided by the present disclosure can be provided in non-effervescent or effervescent granules and powders to reconstitute liquid dosage forms. Pharmaceutically acceptable carriers and excipients used in non-effervescent granules or powders may include diluents, sweeteners and wetting agents. Pharmaceutically acceptable carriers and excipients used in effervescent granules or powders may include organic acids and carbon dioxide sources.

Colorants and flavorings can be used in all of the above formulations.

The compounds disclosed in the present disclosure can be also combined with soluble polymers as targeted drug carriers. Such polymers include polyvinylpyrrolidone, pyran copolymers, poly (hydroxypropyl methylacrylamide)-phenol, poly (hydroxyethyl asparagine)-phenol, or poly (oxyethylene)-polylysine substituted with palmityl residues. In addition, the disclosed compounds can be used in drug control release of a class of biodegradable polymers, for example, polylactic acid, ε-poly epsilon-caprolactone, poly hydroxybutyrate, get together the original acid ester, polyacetal, dihydro pyran, cyanoacrylate and hydrogel crosslinking or amphiphilic block copolymer.

The pharmaceutical compositions provided by the present disclosure can be formulated or modified release dosage forms, including delayed, sustained-release, pulse, controlled, targeted and programmed release forms.

The pharmaceutical composition provided by the present disclosure can be formulated with other active ingredients that do not impair the expected therapeutic effect, or with substances that supplement the expected effect.

The pharmaceutical composition provided by the present disclosure can be administered by injection, infusion or implantation outside the intestines and stomach for local or systemic administration. Parenteral administration as used in the present disclosure includes intravenous, intra-arterial, intraperitoneal, intrathecal, intraventricular, intraurethral, intrasternal, intracranial, intramuscular, synovial and subcutaneous administration.

The pharmaceutical composition provided by the present disclosure can be formulated into any dosage form suitable for parenteral administration, including solution, suspension, emulsion, micelle, liposome, microsphere, nano system and solid form suitable for making solution or suspension in liquid before injection. Such dosage forms can be prepared according to the conventional methods known to the technical personnel in the field of pharmaceutical science (see Remington: The science and Practice of Pharmacy, above).

Pharmaceutical compositions intended for parenteral administration may include one or more pharmaceutically acceptable carriers and excipients, including, but not limited to, water carriers, water miscible carriers, non-water carriers, antimicrobial agents or antimicrobial growth inhibitors, stabilizers, solubilizing enhancers, isotonic agents, buffers, antioxidants, local anesthetics, suspending agent and dispersant, wetting agent or emulsifier, complexing agent, multivalent chelating agent or chelating agent, antifreeze, cryoprotectant, thickener, pH regulator and inert gas.

Suitable water containing carriers include, but are not limited to, water, saline, normal saline or phosphate buffered saline (PBS), sodium chloride injection, Ringers injection, isotonic glucose injection, sterile water injection, glucose and lactated Ringers injection. Non waterborne carriers include, but are not limited to, non-volatile oils of plant origin, castor oil, corn oil, cottonseed oil, olive oil, peanut oil, peppermint oil, safflower oil, sesame oil, soybean oil, hydrogenated vegetable oil, medium chain triglycerides of hydrogenated soybean oil and coconut oil, and palm seed oil. Water miscible carriers include, but are not limited to, ethanol, 1,3-butanediol, liquid polyethylene glycol (e.g., PEG 300 and PEG 400), propylene glycol, glycerol, N-methyl-2-pyrrolidone, N,N-dimethylacetamide, and dimethyl sulfoxide.

Suitable antimicrobial agents or preservatives include, but are not limited to, phenol, mercury, benzyl alcohol, cresol, chlorobutanol, methyl p-hydroxybenzoate and propyl p-hydroxybenzoate, benzalkonium chloride (e.g., benzalkonium chloride), thiomersal, methyl and propyl nipagin, and sorbic acid. Suitable isotonic agents include, but are not limited to, sodium chloride, glycerol and glucose. Suitable buffers include, but are not limited to, phosphate and citrate. Suitable antioxidants are those as described in the present disclosure, including bisulfite and sodium metabisulfite. Suitable local anesthetics include, but are not limited to, procaine hydrochloride. Suitable suspension aids and dispersants are those as described in the present disclosure, including sodium carboxymethyl cellulose, hydroxypropyl methyl cellulose and polyvinylpyrrolidone. Suitable emulsifiers include those described in the present disclosure, including polyoxyethylene dehydrated sorbitol monolaurate, polyoxyethylene dehydrated sorbitol monooleate 80, and triethanolamine oleate. Suitable multivalent chelating agents or chelating agents include, but are not limited to, EDTA. Suitable pH regulators include, but are not limited to, sodium hydroxide, hydrochloric acid, citric acid and lactic acid. Suitable complexing agents include, but are not limited to, cyclodextrins, including α-cyclodextrin, β-cyclodextrin, hydroxypropyl-β-cyclodextrin, sulfobutyl ether-β-cyclodextrin and sulfobutyl ether 7-β-cyclodextrin (Captisol®, CyDex, Lenexa, KS).

The pharmaceutical composition provided by the present disclosure can be formulated into single dose or multi dose administration. The single dose preparation is packaged in ampoules, vials or syringes. The multi dose parenteral preparation must contain an antimicrobial agent with bacteriostatic or antifungal concentration. All parenteral preparations must be sterile, as known and practiced in the art.

In one embodiment, the pharmaceutical composition is provided in a ready to use sterile solution. In another embodiment, the pharmaceutical composition is provided as a sterile dry soluble product, including a lyophilized powder and a subcutaneous injection tablet, which is reconstituted with a carrier before use. In another embodiment, the pharmaceutical composition is formulated as a ready to use sterile suspension. In a further embodiment, the pharmaceutical composition is formulated as a sterile dry insoluble product reconstituted with a carrier prior to use. In another embodiment, the pharmaceutical composition is formulated as a ready to use sterile emulsion.

The pharmaceutical composition can be configured as suspension, solid, semi-solid or thixotropic liquid which is used as a reservoir for implantable drug delivery. In one embodiment, the pharmaceutical composition disclosed in the present disclosure is dispersed in a solid internal matrix surrounded by an external polymeric membrane that is insoluble in body fluids but allows the active ingredients in the pharmaceutical composition to diffuse through.

Suitable internal substrates include polymethylmethacrylate, polybutylacrylate, plasticized or unplasticized polyvinyl chloride, plasticized nylon, plasticized polyethylene terephthalate, plasticized polyethylene terephthalate, natural rubber, polyethylene, polyisoprene, polyisobutylene, polybutadiene, polydimethylsiloxane, ethylene vinyl acetate copolymer Silicone rubber, silicone carbonate copolymer, hydrophilic polymer such as acrylic acid and methacrylic acid ester hydrogel, collagen, cross-linked polyvinyl alcohol and crosslinked partially hydrolyzed polyvinyl acetate.

Suitable external polymeric films include polyethylene, polypropylene, ethylene/propylene copolymer, ethylene/ethyl acrylate copolymer, ethylene/vinyl acetate copolymer, silicone rubber, polydimethylsiloxane, chloroprene rubber, chlorinated polyethylene, polyvinyl chloride, copolymer of ethylene chloride and vinyl acetate, vinylidene chloride, ethylene and propylene, ionic crosslinking polymers include polyethylene terephthalate, butyl rubber, chlorohydrin rubber, ethylene/vinyl alcohol copolymer, ethylene/vinyl acetate/vinyl alcohol trimer and ethylene/vinyl alcohol copolymer.

On the other hand, the pharmaceutical composition disclosed in the present disclosure can be formulated into any dosage form suitable for inhalation administration to patients, such as dry powder, aerosol, suspension or solution composition. In one embodiment, the pharmaceutical composition disclosed in the present disclosure can be formulated into a dosage form suitable for inhalation administration to patients with dry powder. In another embodiment, the pharmaceutical composition disclosed in this disclosure can be formulated into a dosage form suitable for inhalation of a patient through a sprayer. A dry powder composition delivered to the lung by inhalation typically comprises a fine powder like compound as disclosed in the present disclosure and one or more fine powder like pharmaceutically acceptable excipients. Pharmaceutically acceptable excipients particularly suitable for use as dry powders are known to those skilled in the art, including lactose, starch, mannitol, and mono-, di- and polysaccharides. Fine powders can be prepared by, for example, micronization and grinding. In general, a reduced size (e.g., micronized) compound can be defined by a $D_{50}$ value of about 1 to 10 microns (e.g., measured by laser diffraction).

The aerosol can be prepared by suspending or dissolving the compounds disclosed in the present disclosure in a liquefied propellant. Suitable propellants include chlorinated hydrocarbons, hydrocarbons and other liquefied gases. Representative propellants include: trichlorofluoromethane (propellant 11), difluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane Isobutane and pentane. Aerosols containing the compounds disclosed in the present disclosure are generally administered to patients through a metered dose inhaler (MDI). Such a device is known to those skilled in the art.

Aerosols may contain additional pharmaceutically acceptable excipients that can be used by MDIs, such as surfactants, lubricants, cosolvents, and other excipients, to improve the physical stability, valve characteristics, solubility, or taste of the preparation.

The pharmaceutical composition suitable for transdermal drug delivery can be prepared into discontinuous patch, which is intended to keep close contact with the epidermis of the patient for a prolonged period of time. For example, the active ingredient can be delivered from the patch by ion permeation as generally described in *Pharmaceutical Research,* 3 (6), 318 (1986).

The pharmaceutical composition suitable for local administration can be formulated as ointment, cream, suspension, lotion, powder, solution, paste, gel, spray, aerosol or oil. For example, ointments, creams and gels can be formulated with water or oil matrix, and suitable thickeners and/or gels and/or solvents. Such a matrix may include water and/or oil, such as liquid paraffin and vegetable oil (such as peanut oil or castor oil) or a solvent such as polyethylene glycol. Thickeners and gels based on matrix properties include soft paraffin, aluminum stearate, cetyl stearyl alcohol, polyethylene glycol, lanolin, beeswax, polycarboxyethylene and cellulose derivatives and/or monostearic acid glyceride and/or nonionic emulsifiers.

Lotion can be prepared with water or oil base, and usually contains one or more emulsifiers, stabilizers, dispersants, suspending agents or thickeners.

The external powder can be formed in the presence of any suitable powder matrix such as talc, lactose or starch. Drops may be prepared from an aqueous or nonaqueous matrix containing one or more dispersants, solubilizers, suspending agents or preservatives.

Local preparations can be administered once or more a day in the affected area. Closed dressings covering the skin are preferred. Adhesive storage system can achieve continuous or extended drug delivery.

Use of Compounds and Compositions

The compounds or pharmaceutical compositions disclosed in the present disclosure can be used to prepare for the treatment, prevention, improvement, control or alleviation of hyperproliferative diseases in mammals, including humans.

In particular, the compounds of the present disclosure can be used as drugs for the preparation of prevention or treatment of human hyperproliferative diseases, including liver cancer, leukemia, breast cancer, colon adenocarcinoma, gastric cancer, lung cancer, Bart's esophageal cancer, cervical cancer, pancreatic cancer, endometrial cancer, bone cancer, lymphoma, kidney cancer, brain cancer, nerve cancer, nasopharyngeal cancer, oral cancer and colorectal cancer.

The compounds or compositions of the present disclosure can be applied to, but are not limited to, the use of effective amounts of the compounds or compositions disclosed herein for administration to patients to prevent, treat or alleviate hyperproliferative diseases in mammals, including humans.

In addition to being beneficial to human treatment, the compounds and pharmaceutical compositions disclosed herein can be also applied to veterinary treatment of pets, imported animals and mammals in farm animals. Other examples of animals include horses, dogs and cats. Herein, compounds of the present disclosure include pharmaceutically acceptable derivatives thereof.

Therapeutic Method

In one embodiment, the treatment method disclosed in the present disclosure includes giving a safe and effective amount of the compound or a pharmaceutical composition containing the disclosed compound to a patient in need. The embodiments of the present disclosure include methods for treating the above-mentioned diseases by giving a safe and effective amount of the compounds of the present disclosure or a pharmaceutical composition containing the compounds of the present disclosure to patients in need.

In an embodiment, a compound disclosed in the present disclosure or a pharmaceutical composition comprising the compound disclosed in the present disclosure may be administered by any suitable route of administration, including systemic administration and local administration. Systemic administration includes oral administration, parenteral administration, transdermal administration and rectal administration. Typical parenteral administration refers to administration by injection or infusion, including intravenous, intramuscular and subcutaneous injection or infusion. Topical administration includes administration to the skin as well as to the eyes, ears, vagina, inhalation and nose. In one embodiment, a compound disclosed in the present disclosure or a pharmaceutical composition comprising the compound disclosed in the present disclosure may be administered orally. In another embodiment, a compound disclosed in the present disclosure or a pharmaceutical composition comprising the compound disclosed in the present disclosure may be an inhalation administration. In another embodiment, the compound disclosed in the present disclosure or containing the compound disclosed in the present disclosure may be intranasal administration.

In one embodiment, the compound disclosed in the present disclosure or the pharmaceutical composition containing the compound disclosed in the present disclosure can be administered once, or several times at different time intervals within a specified time period according to the administration scheme. For example, once, twice, three or four times a day. In one embodiment, the drug is administered once a day. In another implementation, the drug was administered twice a day. It can be administered until the desired therapeutic effect is achieved or maintained indefinitely. The appropriate dosage regimen of a compound disclosed in the present disclosure or a pharmaceutical composition containing the compound disclosed in the present disclosure depends on the pharmacokinetic properties of the compound, such as dilution, distribution and half-life, which can be determined by a skilled person. In addition, the suitable administration scheme of the compounds disclosed in the present disclosure or the pharmaceutical composition containing the compounds disclosed in the present disclosure, including the duration of implementing the scheme, depends on the disease being treated, the severity of the disease being treated, the age and physical condition of the patient being treated, the medical history of the patient being treated, the nature of the simultaneous therapy, and the dosage regimen The desired therapeutic effect and other factors are within the scope of technical personnel's knowledge and experience. Such a technician should also understand that the individual patient's response to the dosing regimen, or the individual patient's need to change over time, may require adjustment of the dosing regimen.

The compounds disclosed in the present disclosure can be administered at the same time with one or more other therapeutic agents, or before or after. The compounds of the present disclosure can be administered separately or together with other therapeutic agents in the form of pharmaceutical compositions through the same or different administration routes.

For an individual of about 50-70 kg, the disclosed pharmaceutical compositions and combinations of the disclosure can be in a unit dose form containing about 1-1000 mg, or about 1-500 mg, or about 1-250 mg, or about 1-150 mg, or about 0.5-100 mg, or about 1-50 mg of the active ingredient. The therapeutically effective amount of a compound, a pharmaceutical composition or a combination thereof depends on the species, weight, age and condition of the individual, the disorder or disease being treated or the severity thereof. Doctors, clinicians or veterinarians with common skills can easily decide the effective amount of each active ingredient needed in the development process to prevent, treat or suppress disorders or diseases.

The above cited dose characteristics have been confirmed in vitro and in vivo experiments using advantageous mammals (e.g., mice, rats, dogs, monkeys) or their organs, tissues and specimens in vitro. The compounds disclosed in the present disclosure can be used in vitro in the form of solutions, such as aqueous solutions, or in the form of suspensions or aqueous solutions in vivo, enteral or parenteral, especially intravenously.

In one embodiment, the therapeutically effective dose of the compounds disclosed in the present disclosure ranges from about 0.1 mg to about 2000 mg per day. The pharmaceutical composition thereof should provide a dose of the compound of about 0.1 mg to about 2000 mg. In a particular embodiment, the prepared drug dose unit form can provide about 1 mg to about 2000 mg, about 10 mg to about 1000 mg, about 20 mg to about 500 mg, or about 25 mg to about 250 mg of the main active ingredients or a combination of the main ingredients in each dose unit form. In a particular embodiment, the prepared drug dose unit form can provide about 10 mg, 20 mg, 25 mg, 50 mg, 100 mg, 250 mg, 500 mg, 1000 mg or 2000 mg of the main active ingredient.

In addition, the compounds disclosed in the present disclosure can be administered in a prodrug form. In the present disclosure, the "prodrugs" of the compounds disclosed herein are functional derivatives that can eventually release the compounds disclosed in the present disclosure in vivo when administered to patients. When a compound disclosed herein is given in the form of a prodrug, a person skilled in the art may implement one or more of the following modes: (a) change the in vivo onset time of the compound; (b) change the duration of action of the compound in vivo; (c) change the internal transport or distribution of compounds; (d) change the solubility of the compound in vivo; and (e) overcome the side effects or other difficulties faced by the compounds. Typical functional derivatives used in the preparation of prodrugs include variants of compounds that are cleaved chemically or enzymatically in vivo. These variants including the preparation of phosphates, amides, esters, thioesters, carbonates and carbamates are well known to those skilled in the art.

Detailed Description of Embodiments The following examples are used to further illustrate the present disclosure, but the present disclosure is not limited to these examples.

Example 1

7-O-(3-fluorocinnamic acid)acyl BFA (Compound 1a), 4-O-(3-fluorocinnamic acid)acyl BFA (Compound 1b) and 4,7-O-bis(3-fluorocinnamic acid)acyl BFA (Compound 1c)

BFA (40 mg, 1 eq), DMAP (1 eq) and EDC·HCl (4 eq) were dissolved in 8 ml of anhydrous DCM under nitrogen. After stirring at 40° C. for 10 min, a DCM solution of 3-fluorocinnamic acid (2 eq) was added. The reaction was continued for 2 h. After TLC detection, water was added for extraction. Organic phase was concentrated under reduced pressure, and the crude extract was separated and purified to give white solids 1a, 1b and 1c in yields of 20%, 40% and 30%, respectively.

Structural characterization: Compound 1a: $^1$H NMR (600 MHz, Chloroform-d) δ=7.59 (d, J=16.0, 1H), 7.39-7.31 (m, 2H), 7.29 (s, 1H), 7.21 (dt, J=9.6, 2.0, 1H), 7.07 (td, J=8.3, 2.5, 1H), 6.39 (d, J=15.9, 1H), 5.93 (dd, J=15.6, 1.9, 1H), 5.73 (ddd, J=15.0, 10.2, 4.6, 1H), 5.32-5.18 (m, 2H), 4.85 (ddd, J=12.2, 6.8, 3.5, 1H), 4.15 (d, J=9.1, 1H), 2.42 (p, J=8.6, 1H), 2.35 (ddd, J=14.7, 9.3, 5.6, 1H), 2.29 (ddd, J=11.6, 7.1, 2.9, 1H), 2.01 (dtt, J=17.4, 8.9, 3.8, 1H), 1.98-1.88 (m, 2H), 1.84 (td, J=15.3, 13.2, 4.3, 2H), 1.73 (ddd, J=17.5, 9.1, 4.0, 1H), 1.67 (dt, J=12.7, 5.6, 1H), 1.53 (dddd, J=14.1, 10.2, 7.4, 2.3, 1H), 1.25 (d, J=6.3, 3H), 0.99-0.90 (m, 1H). $^{13}$C NMR (125 MHz, Chloroform-d) δ=166.4, 164.1, 162.1, 151.6, 143.5, 136.8, 136.1, 131.1, 130.6, 124.2, 119.8, 117.9, 117.4, 114.5, 75.9, 75.7, 71.9, 52.3, 44.1, 40.3, 38.8, 34.2, 31.9, 26.8, 21.0. ESI-MS m/z 429.21 $[M+H]^+$.

Compound 1b: $^1$H NMR (500 MHz, Chloroform-d) δ=7.67 (d, J=15.9, 1H), 7.37 (td, J=8.0, 5.7, 1H), 7.33-7.27 (m, 2H), 7.23 (dt, J=9.7, 2.0, 1H), 7.09 (td, J=8.2, 2.5, 1H), 6.46 (d, J=16.0, 1H), 5.79-5.66 (m, 2H), 5.39 (ddd, J=10.5, 3.4, 1.9, 1H), 5.31 (dd, J=15.2, 9.5, 1H), 4.84 (dqd, J=12.5, 6.2, 1.7, 1H), 4.32 (p, J=4.7, 1H), 2.45 (qd, J=9.2, 6.9, 1H), 2.29-2.19 (m, 2H), 2.06-1.93 (m, 2H), 1.85 (td, J=11.2, 4.4, 2H), 1.71 (m, 2H), 1.53 (dddt, J=13.6, 6.8, 4.5, 2.7, 2H), 1.24 (d, J=6.3, 3H), 0.98-0.88 (m, 1H). $^{13}$C NMR (125 MHz, Chloroform-d) δ=165.8, 165.6, 164.1, 162.1, 147.3, 144.5, 136.5, 130.8, 130.7, 124.3, 118.9, 118.4, 117.6, 114.6, 76.8, 72.5, 72.0, 49.7, 44.5, 43.3, 41.1, 34.2, 31.9, 26.7, 20.9. HRESIMS m/z 429.2065 $[M+H]^+$ (calcd. for $[C_{25}H_{30}FO_5]^+$, 429.2072).

Compound 1c: $^1$H NMR (600 MHz, Chloroform-d) δ=7.64 (dd, J=40.5, 16.0, 2H), 7.38-7.27 (m, 5H), 7.22 (dddd, J=9.6, 4.3, 2.5, 1.6, 2H), 7.08 (qdd, J=8.2, 2.5, 1.0, 2H), 6.43 (dd, J=35.1, 16.0, 2H), 5.82-5.71 (m, 2H), 5.43 (ddd, J=10.2, 3.4, 1.9, 1H), 5.32-5.25 (m, 2H), 4.86 (dqd, J=10.9, 6.2, 1.7, 1H), 2.55 (qd, J=9.4, 6.7, 1H), 2.41 (ddd, J=15.0, 9.7, 5.6, 1H), 2.28-2.14 (m, 2H), 2.03 (dddd, J=13.0, 9.6, 4.9, 2.2, 1H), 1.91-1.68 (m, 5H), 1.59-1.51 (m, 1H), 1.25 (d, J=6.3, 3H), 1.01-0.92 (m, 1H). $^{13}$C NMR (150 MHz, Chloroform-d) δ=166.2, 165.7, 165.5, 163.9, 162.3, 147.1, 144.6, 143.5, 136.7, 136.4, 135.9, 131.4, 130.6, 124.3, 124.2, 119.7, 118.7, 118.6, 117.6, 117.5, 117.4, 117.2, 114.5, 76.6, 75.7, 72.0, 50.1, 44.2, 40.2, 38.6, 34.2, 31.9, 26.7, 20.9. ESI-MS m/z 577.64 $[M+H]^+$.

Example 2

7-O-(2-fluorocinnamic acid)acyl BFA (Compound 2a), 4-O-(2-fluorocinnamic acid)acyl BFA (Compound 2b) and 4,7-O-bis(2-fluorocinnamic acid)acyl BFA (Compound 2c)

According to the preparation method of Example 1, white solids 2a, 2b and 2c were obtained in yields of 20%, 45% and 30%, respectively.

Structural characterization: Compound 2a: $^1$H NMR (600 MHz, Chloroform-d) δ=7.78 (d, J=16.2, 1H), 7.53 (td, J=7.6, 1.7, 1H), 7.39-7.32 (m, 2H), 7.16 (td, J=7.5, 1.1, 1H), 7.10 (ddd, J=10.8, 8.2, 1.1, 1H), 6.50 (d, J=16.2, 1H), 5.93 (dd, J=15.7, 2.0, 1H), 5.73 (ddd, J=15.0, 10.3, 4.6, 1H), 5.31-5.22 (m, 2H), 4.86 (dqd, J=12.6, 6.3, 1.7, 1H), 4.15 (dt, J=9.6, 2.5, 1H), 2.47-2.26 (m, 3H), 2.06-1.81 (m, 5H), 1.78-1.64 (m, 2H), 1.58-1.48 (m, 1H), 1.26 (d, J=6.2, 3H), 0.99-0.90 (m, 1H). $^{13}$C NMR (150 MHz, Chloroform-d) δ=166.6, 162.3, 160.6, 151.6, 137.5, 136.1, 131.9, 131.1, 129.2, 124.6, 122.6, 121.0, 117.9, 116.4, 76.0, 75.6, 71.9, 52.3, 44.1, 40.3, 38.7, 34.2, 31.9, 26.8, 21.0. ESI-MS m/z 429.21 $[M+H]^+$.

Compound 2b: $^1H$ NMR (600 MHz, Chloroform-d) δ=7.83 (d, J=16.2, 1H), 7.53 (td, J=7.6, 1.7, 1H), 7.36 (dddd, J=8.6, 7.1, 5.2, 1.7, 1H), 7.29 (dd, J=15.6, 3.3, 1H), 7.16 (td, J=7.6, 1.1, 1H), 7.10 (ddd, J=10.9, 8.3, 1.1, 1H), 6.56 (d, J=16.2, 1H), 5.77-5.67 (m, 2H), 5.38 (ddd, J=10.5, 3.4, 1.9, 1H), 5.30 (dd, J=15.2, 9.6, 1H), 4.83 (dqd, J=12.5, 6.3, 1.7, 1H), 4.31 (ddd, J=9.2, 5.2, 3.9, 1H), 2.44 (qd, J=9.2, 7.0, 1H), 2.28-2.19 (m, 2H), 2.03-1.93 (m, 2H), 1.88-1.79 (m, 2H), 1.76-1.63 (m, 2H), 1.52 (ddtd, J=13.8, 8.7, 4.8, 2.0, 2H), 1.22 (d, J=6.3, 3H), 0.96-0.87 (m, 1H). $^{13}C$ NMR (150 MHz, Chloroform-d) δ=165.8, 162.3, 160.6, 147.4, 138.5, 136.5, 132.1, 130.7, 129.3, 124.6, 120.0, 118.3, 116.4, 116.3, 76.7, 72.4, 72.0, 49.6, 44.4, 43.2, 41.1, 34.1, 31.9, 26.7, 20.9. ESI-MS m/z 429.21 $[M+H]^+$.

Compound 2c: $^1H$ NMR (600 MHz, Chloroform-d) δ=7.82 (dd, J=38.3, 16.2, 2H), 7.54 (tdd, J=7.5, 4.1, 1.7, 2H), 7.41-7.29 (m, 3H), 7.20-7.07 (m, 4H), 6.55 (dd, J=38.3, 16.2, 2H), 5.84-5.69 (m, 2H), 5.44 (ddd, J=10.2, 3.4, 1.8, 1H), 5.34-5.26 (m, 2H), 4.87 (dqd, J=10.9, 6.3, 1.8, 1H), 2.55 (qd, J=9.3, 6.7, 1H), 2.41 (ddd, J=14.9, 9.7, 5.6, 1H), 2.32-2.17 (m, 2H), 2.04 (dtd, J=12.2, 6.4, 5.3, 3.7, 1H), 1.93-1.69 (m, 5H), 1.60-1.51 (m, 1H), 1.25 (d, J=6.3, 3H), 1.02-0.92 (m, 1H). $^{13}C$ NMR (150 MHz, Chloroform-d) δ=166.5, 165.8, 165.8, 160.7, 160.7, 147.2, 138.7, 137.6, 136.0, 132.2, 131.9, 131.3, 129.4, 129.3, 124.6, 124.6, 122.6, 122.4, 121.0, 120.0, 118.6, 116.4, 116.3, 76.6, 75.7, 72.0, 50.1, 44.3, 40.3, 38.6, 34.2, 31.9, 26.7, 20.9. ESI-MS m/z 577.64 $[M+H]^+$.

Example 3

7-O-(4-fluorocinnamic acid)acyl BFA (Compound 3a), 4-O-(4-fluorocinnamic acid)acyl BFA (Compound 3b) and 4,7-O-bis(4-fluorocinnamic acid)acyl BFA (Compound 3c)

According to the preparation method of Example 1, white solids 3a, 3b and 3c were obtained in yields of 20%, 33% and 43%, respectively.

Structural characterization: Compound 3a: $^1H$ NMR (600 MHz, Chloroform-d) δ=7.61 (d, J=16.0, 1H), 7.54-7.48 (m, 2H), 7.36 (dd, J=15.7, 3.1, 1H), 7.10-7.04 (m, 2H), 6.32 (d, J=16.0, 1H), 5.93 (dd, J=15.6, 1.9, 1H), 5.73 (ddd, J=15.0, 10.2, 4.6, 1H), 5.32-5.20 (m, 2H), 4.86 (dqd, J=12.5, 6.2, 1.8, 1H), 4.15 (dt, J=9.7, 2.3, 1H), 2.42 (qd, J=9.1, 7.0, 1H), 2.40-2.33 (m, 1H), 2.29 (dddd, J=12.9, 7.3, 3.3, 1.5, 1H), 2.02 (dddd, J=10.5, 8.3, 5.0, 2.7, 1H), 1.98-1.91 (m, 1H), 1.91-1.82 (m, 2H), 1.78-1.71 (m, 1H), 1.72-1.62 (m, 2H), 1.53 (dddd, J=14.5, 10.9, 7.3, 2.3, 1H), 1.26 (d, J=6.2, 3H), 0.99-0.89 (m, 1H). $^{13}C$ NMR (125 MHz, Chloroform-d) δ=166.6, 166.3, 165.0, 163.0, 151.6, 143.6, 136.1, 131.1, 130.1, 130.1, 118.2, 117.9, 116.3, 116.1, 75.9, 75.5, 71.9, 52.4, 44.1, 40.3, 38.8, 34.2, 31.9, 26.8, 21.0. ESI-MS m/z 429.21 $[M+H]^+$.

Compound 3b: $^1H$ NMR (600 MHz, Chloroform-d) δ=7.67 (d, J=16.0, 1H), 7.55-7.47 (m, 2H), 7.29 (dd, J=15.7, 3.3, 1H), 7.08 (dd, J=9.7, 7.5, 2H), 6.38 (d, J=16.0, 1H), 5.78-5.66 (m, 2H), 5.37 (ddd, J=10.5, 3.4, 1.9, 1H), 5.34-5.27 (m, 1H), 4.83 (dqd, J=12.5, 6.2, 1.7, 1H), 4.34-4.27 (m, 1H), 2.44 (qd, J=9.2, 6.9, 1H), 2.28-2.17 (m, 2H), 2.06-1.92 (m, 2H), 1.87-1.77 (m, 2H), 1.76-1.62 (m, 2H), 1.57-1.46 (m, 2H), 1.23 (d, J=6.2, 3H), 0.97-0.88 (m, 1H). $^{13}C$ NMR (150 MHz, Chloroform-d) δ=165.9, 165.9, 165.0, 163.3, 147.5, 144.6, 136.5, 130.8, 130.5, 130.2, 118.3, 117.2, 116.3, 116.2, 76.6, 72.4, 72.0, 49.7, 44.4, 43.3, 41.1, 34.1, 31.9, 26.7, 20.9. ESI-MS m/z 429.21 $[M+H]^+$.

Compound 3c: $^1H$ NMR (600 MHz, Chloroform-d) δ=7.66 (dd, J=39.7, 16.0, 2H), 7.52 (dtd, J=9.1, 4.7, 2.0, 4H), 7.32 (dd, J=15.7, 3.4, 1H), 7.13-7.04 (m, 4H), 6.37 (dd, J=32.8, 16.0, 2H), 5.82-5.72 (m, 2H), 5.43 (ddd, J=10.2, 3.3, 1.8, 1H), 5.34-5.24 (m, 2H), 4.87 (dqd, J=10.9, 6.2, 1.7, 1H), 2.55 (qd, J=9.3, 6.6, 1H), 2.41 (ddd, J=15.0, 9.7, 5.6, 1H), 2.28-2.15 (m, 2H), 2.04 (dtt, J=10.9, 5.7, 2.4, 1H), 1.92-1.68 (m, 5H), 1.58-1.50 (m, 1H), 1.25 (d, J=6.2, 3H), 1.01-0.93 (m, 1H). $^{13}C$ NMR (150 MHz, Chloroform-d) δ=166.5, 165.8, 165.0, 165.0, 163.2, 147.3, 144.7, 143.7, 136.0, 131.4, 130.7, 130.5, 130.3, 130.2, 130.1, 130.1, 118.6, 118.1, 117.1, 116.3, 116.3, 116.2, 116.1, 76.5, 75.6, 72.0, 50.2, 44.3, 40.3, 38.7, 34.2, 31.9, 26.7, 20.9. ESI-MS m/z 577.64 $[M+H]^+$.

Example 4

7-O-(2-bromocinnamic acid)acyl BFA (Compound 4a), 4-O-(2-bromocinnamic acid)acyl BFA (Compound 4b) and 4,7-O-bis(2-bromocinnamic acid) acyl BFA (Compound 4c)

According to the preparation method of Example 1, white solids 4a, 4b and 4c were obtained in yields of 19%, 35% and 40%, respectively.

Structural characterization: Compound 4a: $^1H$ NMR (600 MHz, Chloroform-d) δ=8.03 (d, J=15.9, 1H), 7.61 (ddd, J=7.8, 4.7, 1.4, 2H), 7.37 (dd, J=15.7, 3.1, 1H), 7.32 (t, J=7.6, 1H), 7.23 (td, J=7.7, 1.6, 1H), 6.36 (dd, J=15.9, 0.9, 1H), 5.93 (dt, J=15.7, 1.5, 1H), 5.74 (ddd, J=15.0, 10.3, 4.6, 1H), 5.33-5.26 (m, 2H), 4.87 (dtd, J=11.0, 6.9, 5.1, 1H), 4.16 (d, J=10.0, 1H), 2.48-2.40 (m, 1H), 2.36 (ddd, J=14.9, 9.5, 5.6, 2H), 2.04-1.81 (m, 5H), 1.78 (d, J=5.1, 1H), 1.76-1.68 (m, 2H), 1.56-1.51 (m, 1H), 1.27 (d, J=6.3, 3H), 0.99-0.91 (m, 1H). ESI-MS m/z 489.12 $[M+H]^+$, 491.12 $[M+2+H]^+$.

Compound 4b: $^1H$ NMR (600 MHz, Chloroform-d) δ=8.11 (d, J=15.9, 1H), 7.62 (ddd, J=8.0, 5.1, 1.4, 2H), 7.37-7.21 (m, 3H), 6.42 (d, J=16.0, 1H), 5.81-5.66 (m, 2H), 5.39 (ddd, J=10.5, 3.4, 1.9, 1H), 5.35-5.27 (m, 1H), 4.85 (dtd, J=12.6, 8.1, 7.2, 5.4, 1H), 4.33 (p, J=4.7, 1H), 2.46 (qd, J=9.2, 7.0, 1H), 2.31-2.19 (m, 2H), 2.06-1.95 (m, 2H), 1.85 (tdd, J=12.3, 5.0, 2.8, 2H), 1.72 (dddd, J=28.1, 14.2, 8.3, 3.6, 3H), 1.53 (dddd, J=15.3, 7.2, 5.9, 3.3, 2H), 1.24 (d, J=6.2, 3H), 0.99-0.89 (m, 1H). $^{13}C$ NMR (150 MHz, Chloroform-d) δ=165.9, 165.4, 147.3, 144.3, 136.5, 134.3, 133.6, 131.6, 130.8, 128.0, 127.9, 125.6, 120.2, 118.5, 76.8, 72.5, 72.0, 49.7, 44.5, 43.3, 41.1, 34.2, 31.9, 26.7, 20.9. ESI-MS m/z 489.12 $[M+H]^+$, 491.12 $[M+2+H]^+$.

Compound 4c: $^1H$ NMR (600 MHz, Chloroform-d) δ=8.07 (dd, J=45.1, 16.0, 2H), 7.66-7.54 (m, 4H), 7.36-7.29 (m, 3H), 7.23 (tdd, J=7.7, 6.2, 1.6, 2H), 6.39 (dd, J=36.1, 15.9, 2H), 5.82-5.73 (m, 2H), 5.44 (ddd, J=10.2, 3.4, 1.8, 1H), 5.36-5.28 (m, 2H), 4.86 (dqd, J=10.9, 6.2, 1.7, 1H), 2.62-2.51 (m, 1H), 2.41 (ddd, J=14.9, 9.8, 5.5, 1H), 2.31-2.19 (m, 2H), 2.04 (dddd, J=13.2, 9.8, 4.9, 2.3, 1H), 1.91-1.70 (m, 5H), 1.55 (dddd, J=14.6, 10.9, 7.3, 2.4, 1H), 1.25 (d, J=6.2, 3H), 1.00-0.92 (m, 1H). $^{13}C$ NMR (150 MHz, Chloroform-d) δ=166.0, 165.8, 165.3, 147.1, 144.4, 143.3, 135.9, 134.5, 134.3, 133.6, 133.6, 131.6, 131.4, 131.3, 128.0, 127.9, 127.9, 127.8, 125.6, 125.5, 121.2, 120.1, 118.6, 76.6, 75.8, 72.0, 50.2, 44.2, 40.2, 38.6, 34.2, 31.9, 26.7, 20.9. ESI-MS m/z 699.45 $[M+H]^+$, 701.45 $[M+2+H]^+$.

Example 5

7-O-(3-chlorocinnamic acid)acyl BFA (Compound 5a), 4-O-(3-chlorocinnamic acid)acyl BFA (Compound 5b) and 4,7-O-bis(3-chlorocinnamic acid) acyl BFA (Compound 5c)

According to the preparation method of Example 1, white solids 5a, 5b and 5c were obtained in yields of 20%, 30% and 45%, respectively.

Structural characterization: Compound 5a: $^1$H NMR (600 MHz,) δ=7.58 (d, J=15.9, 1H), 7.51 (t, J=1.8, 1H), 7.40-7.30 (m, 4H), 6.40 (d, J=15.8, 1H), 5.93 (dd, J=15.6, 1.9, 1H), 5.74 (ddd, J=15.0, 10.2, 4.6, 1H), 5.33-5.21 (m, 2H), 4.87 (dqd, J=12.5, 6.0, 1.7, 1H), 4.19-4.12 (m, 1H), 2.47-2.26 (m, 3H), 2.08-1.79 (m, 5H), 1.78-1.65 (m, 2H), 1.59-1.50 (m, 2H), 1.27 (d, J=6.4, 3H), 1.00-0.92 (m, 1H). ESI-MS m/z 445.95 [M+H]$^+$, 447.95 [M+2+H]$^+$.

Compound 5b: $^1$H NMR (600 MHz,) δ=7.63 (d, J=16.0, 1H), 7.50 (t, J=1.9, 1H), 7.39 (dt, J=7.4, 1.5, 1H), 7.36-7.33 (m, 1H), 7.33-7.30 (m, 1H), 7.30-7.24 (m, 1H), 6.45 (d, J=16.0, 1H), 5.77-5.63 (m, 2H), 5.37 (ddd, J=10.5, 3.4, 2.0, 1H), 5.33-5.26 (m, 1H), 4.83 (dqd, J=10.8, 6.4, 1.8, 1H), 4.31 (ddd, J=9.5, 5.4, 4.0, 1H), 2.43 (qd, J=9.2, 6.9, 1H), 2.26-2.17 (m, 2H), 2.03-1.91 (m, 2H), 1.83 (ddtd, J=12.4, 9.6, 4.7, 2.4, 2H), 1.76-1.59 (m, 2H), 1.56-1.47 (m, 2H), 1.22 (d, J=6.2, 3H), 0.97-0.88 (m, 1H). $^{13}$C NMR (150 MHz, Chloroform-d) δ=165.8, 165.5, 147.3, 144.2, 136.5, 136.0, 135.1, 130.8, 130.5, 130.3, 128.0, 126.4, 118.9, 118.4, 76.8, 72.4, 72.0, 49.7, 44.4, 43.3, 41.1, 34.2, 31.9, 26.7, 20.9. ESI-MS m/z 445.95 [M+H]$^+$, 447.95 [M+2+H]$^+$.

Compound 5c: $^1$H NMR (600 MHz, Chloroform-d) δ=7.62 (dd, J=41.3, 16.0, 2H), 7.52 (dt, J=4.2, 1.8, 2H), 7.43-7.28 (m, 7H), 6.44 (dd, J=36.0, 16.0, 2H), 5.80-5.73 (m, 2H), 5.43 (ddd, J=10.2, 3.4, 1.8, 1H), 5.33-5.26 (m, 2H), 4.87 (dqd, J=10.9, 6.2, 1.7, 1H), 2.60-2.52 (m, 1H), 2.41 (ddd, J=15.0, 9.7, 5.6, 1H), 2.28-2.14 (m, 2H), 2.04 (dddd, J=13.0, 9.6, 4.8, 2.2, 1H), 1.92-1.67 (m, 5H), 1.54 (dddd, J=14.5, 10.8, 7.3, 2.4, 1H), 1.25 (d, J=6.3, 3H), 1.02-0.92 (m, 1H). ESI-MS m/z 610.54 [M+H]$^+$, 612.54 [M+2+H]$^+$.

Example 6

7-O-(3-methylcinnamic acid)acyl BFA (Compound 6a), 4-O-(3-methylcinnamic acid)acyl BFA (Compound 6b) and 4,7-O-bis(3-methylcinnamic acid) acyl BFA (Compound 6c)

According to the preparation method of Example 1, white solids 6a, 6b and 6c were obtained in yields of 20%, 46% and 31%, respectively.

Structural characterization: Compound 6a: $^1$H NMR (500 MHz, Chloroform-d) δ=7.63 (d, J=16.1, 1H), 7.40-7.27 (m, 4H), 7.20 (d, J=7.5, 1H), 6.39 (d, J=16.1, 1H), 5.94 (dd, J=15.7, 2.0, 1H), 5.73 (ddd, J=15.0, 10.2, 4.6, 1H), 5.31-5.21 (m, 2H), 4.87 (dtd, J=11.4, 7.1, 5.3, 1H), 4.19-4.13 (m, 1H), 2.48-2.25 (m, 6H), 2.07-1.80 (m, 6H), 1.78-1.72 (m, 1H), 1.71-1.64 (m, 1H), 1.53 (ddt, J=14.0, 7.3, 2.9, 1H), 1.27 (d, J=6.4, 3H), 1.01-0.91 (m, 1H). $^{13}$C NMR (125 MHz, Chloroform-d) δ=166.8, 166.3, 151.5, 145.1, 138.7, 136.2, 134.5, 131.3, 131.1, 128.9, 128.9, 125.4, 118.2, 117.9, 76.0, 75.4, 71.9, 52.4, 44.2, 40.3, 38.8, 34.3, 32.0, 26.8, 21.5, 21.0. ESI-MS m/z 425.54 [M+H]$^+$.

Compound 6b: $^1$H NMR (500 MHz, Chloroform-d) δ=7.70 (d, J=16.1, 1H), 7.38-7.19 (m, 5H), 6.46 (d, J=16.0, 1H), 5.79-5.68 (m, 2H), 5.39 (dt, J=10.4, 2.6, 1H), 5.32 (dd, J=15.2, 9.6, 1H), 4.85 (dtt, J=13.2, 6.9, 3.4, 1H), 4.33 (p, J=4.7, 1H), 2.46 (qd, J=9.2, 6.9, 1H), 2.38 (s, 3H), 2.29-2.19 (m, 2H), 2.09-2.01 (m, 1H), 1.99-1.94 (m, 1H), 1.91-1.81 (m, 2H), 1.78-1.61 (m, 3H), 1.55-1.50 (m, 2H), 1.24 (d, J=6.2, 3H), 0.95 (dddd, J=14.1, 11.1, 6.9, 3.2, 1H). $^{13}$C NMR (125 MHz, Chloroform-d) δ=166.1, 165.9, 147.5, 146.1, 138.7, 136.6, 134.2, 131.5, 130.8, 129.0, 128.9, 125.5, 118.4, 117.2, 76.5, 72.5, 72.0, 49.8, 44.5, 43.3, 41.2, 34.2, 31.9, 26.8, 21.4, 20.9. ESI-MS m/z 425.54 [M+H]$^+$.

Compound 6c: $^1$H NMR (600 MHz, Chloroform-d) δ=7.67 (dd, J=41.8, 16.0, 2H), 7.38-7.31 (m, 5H), 7.28 (td, J=7.3, 3.0, 2H), 7.22-7.18 (m, 2H), 6.44 (dd, J=34.8, 16.0, 2H), 5.82-5.72 (m, 2H), 5.43 (ddd, J=10.1, 3.3, 1.8, 1H), 5.34-5.26 (m, 2H), 4.87 (dqd, J=12.5, 6.2, 1.7, 1H), 2.55 (qd, J=9.3, 6.5, 1H), 2.41 (ddd, J=15.0, 9.7, 5.6, 1H), 2.37 (s, 6H), 2.28-2.17 (m, 2H), 2.04 (dddd, J=13.0, 9.6, 4.9, 2.1, 1H), 1.91-1.84 (m, 2H), 1.80 (ddd, J=13.4, 9.7, 5.5, 1H), 1.78-1.69 (m, 2H), 1.59-1.51 (m, 1H), 1.25 (d, J=6.2, 3H), 0.97 (qt, J=10.7, 3.5, 1H). $^{13}$C NMR (150 MHz, Chloroform-d) δ=166.6, 165.9, 165.8, 147.4, 146.2, 145.1, 138.7, 138.6, 136.0, 134.4, 134.2, 131.5, 131.3, 131.2, 128.9, 128.9, 128.9, 128.9, 125.5, 125.4, 118.5, 118.1, 117.1, 76.4, 75.5, 71.9, 50.2, 44.2, 40.3, 38.6, 34.2, 31.9, 26.7, 21.4, 21.4, 20.9. ESI-MS m/z 569.71 [M+H]$^+$.

Example 7

7-O-(4-methylcinnamic acid)acyl BFA (Compound 7a), 4-O-(4-methylcinnamic acid)acyl BFA (Compound 7b) and 4,7-O-bis(4-methylcinnamic acid) acyl BFA (Compound 7c According to the preparation method of Example 1, white solids 7a, 7b and 7c were obtained in yields of 15%, 50% and 30%, respectively.

Structural characterization: Compound 7a: $^1$H NMR (600 MHz, Chloroform-d) δ=7.62 (d, J=16.0, 1H), 7.45-7.34 (m, 3H), 7.19 (d, J=7.9, 2H), 6.35 (d, J=16.0, 1H), 5.93 (dd, J=15.6, 1.9, 1H), 5.73 (ddd, J=15.0, 10.2, 4.6, 1H), 5.31-5.21 (m, 2H), 4.86 (dqd, J=12.5, 6.2, 1.8, 1H), 4.15 (d, J=9.7, 1H), 2.47-2.25 (m, 6H), 2.02-1.81 (m, 5H), 1.77-1.67 (m, 2H), 1.57-1.49 (m, 1H), 1.26 (d, J=6.3, 3H), 0.99-0.90 (m, 1H). $^{13}$C NMR (150 MHz, Chloroform-d) δ=167.0, 166.3, 151.6, 144.9, 140.9, 136.2, 131.8, 131.0, 129.8, 129.8, 128.2, 128.2, 117.9, 117.3, 76.0, 75.4, 71.9, 52.4, 44.2, 40.3, 38.8, 34.2, 31.9, 26.8, 21.6, 21.0. ESI-MS m/z 425.54 [M+H]$^+$.

Compound 7b: $^1$H NMR (600 MHz, Chloroform-d) δ=7.69 (d, J=16.0, 1H), 7.42 (d, J=8.2, 2H), 7.29 (dd, J=15.7, 3.3, 1H), 7.19 (d, J=7.9, 2H), 6.41 (d, J=16.0, 1H), 5.78-5.65 (m, 2H), 5.37 (ddd, J=10.5, 3.3, 1.9, 1H), 5.33-5.27 (m, 1H), 4.83 (dqd, J=10.9, 6.2, 1.7, 1H), 4.30 (ddd, J=9.3, 5.2, 3.9, 1H), 2.43 (qd, J=9.2, 7.0, 1H), 2.35 (s, 3H), 2.27-2.17 (m, 2H), 2.03-1.92 (m, 3H), 1.89-1.79 (m, 2H), 1.76-1.63 (m, 2H), 1.51 (dddt, J=15.2, 7.0, 4.1, 1.8, 2H), 1.23 (d, J=6.3, 3H), 0.97-0.88 (m, 1H). $^{13}$C NMR (150 MHz, Chloroform-d) δ=166.2, 165.9, 147.6, 145.9, 141.10, 136.5, 131.5, 130.6, 129.7, 129.7, 128.3, 128.3, 118.2, 116.2, 76.4, 72.3, 71.9, 49.7, 44.4, 43.2, 41.0, 34.1, 31.8, 26.7, 21.6, 20.8. ESI-MS m/z 425.54 [M+H]$^+$.

Compound 7c: $^1$H NMR (600 MHz, Chloroform-d) δ=7.67 (dd, J=40.8, 16.0, 2H), 7.47-7.40 (m, 4H), 7.33 (dd, J=15.6, 3.3, 1H), 7.19 (dd, J=8.2, 2.7, 4H), 6.40 (dd, J=33.1, 15.9, 2H), 5.82-5.72 (m, 2H), 5.43 (ddd, J=10.1, 3.3, 1.8, 1H), 5.33-5.26 (m, 2H), 4.87 (dqd, J=11.1, 6.3, 1.8, 1H), 2.54 (qd, J=9.3, 6.6, 1H), 2.37 (s, 7H), 2.30-2.16 (m, 2H), 2.04 (tdd, J=9.6, 4.9, 2.2, 1H), 1.90-1.69 (m, 5H), 1.55 (dddd, J=17.0, 13.3, 8.7, 2.4, 1H), 1.25 (d, J=6.2, 3H), 1.03-0.91 (m, 1H). $^{13}C$ NMR (150 MHz, Chloroform-d) δ=166.8, 166.1, 165.8, 147.5, 146.0, 144.9, 141.1, 140.9, 136.0, 131.7, 131.5, 131.2, 129.8, 129.8, 129.7, 129.7, 128.3, 128.3, 128.2, 128.2, 118.5, 117.3, 116.2, 76.3, 75.4, 71.9, 50.1, 44.3, 40.3, 38.6, 34.2, 31.9, 26.7, 21.6, 21.6, 20.9. ESI-MS m/z 569.71 $[M+H]^+$.

Example 8

7-O-(2-methylcinnamic acid)acyl BFA (Compound 8a), 4-O-(2-methylcinnamic acid)acyl BFA (Compound 8b) and 4,7-O-bis(2-methylcinnamic acid) acyl BFA (Compound 8c)

According to the preparation method of Example 1, white solids 8a, 8b and 8c were obtained in yields of 18%, 33% and 40%, respectively.

Structural characterization: Compound 8a: $^1H$ NMR (600 MHz, Chloroform-d) δ=7.95 (d, J=15.8, 1H), 7.57-7.53 (m, 1H), 7.37 (dd, J=15.7, 3.1, 1H), 7.27 (td, J=7.2, 1.2, 1H), 7.20 (d, J=15.0, 2H), 6.32 (d, J=15.9, 1H), 5.93 (dd, J=15.7, 1.9, 1H), 5.73 (ddd, J=15.0, 10.2, 4.6, 1H), 5.31-5.23 (m, 2H), 4.86 (dqd, J=12.5, 6.2, 1.7, 1H), 4.16 (dt, J=9.8, 2.4, 1H), 2.43 (s, 4H), 2.38-2.27 (m, 2H), 2.06-1.80 (m, 5H), 1.78-1.66 (m, 3H), 1.53 (dddd, J=14.6, 10.8, 7.3, 2.3, 1H), 1.26 (d, J=6.3, 3H), 0.99-0.90 (m, 1H). $^{13}C$ NMR (150 MHz, Chloroform-d) δ=166.8, 166.4, 151.6, 142.6, 137.8, 136.2, 133.4, 131.0, 130.9, 130.2, 126.5, 126.5, 119.4, 117.8, 75.9, 75.5, 71.9, 52.4, 44.1, 40.3, 38.7, 34.2, 32.0, 26.8, 21.0, 19.9. ESI-MS m/z 425.54 $[M+H]^+$.

Compound 8b: $^1H$ NMR (600 MHz, Chloroform-d) δ=8.02 (d, J=15.9, 1H), 7.56 (dd, J=7.7, 1.4, 1H), 7.33-7.26 (m, 2H), 7.25-7.18 (m, 2H), 6.39 (d, J=15.9, 1H), 5.79-5.65 (m, 2H), 5.38 (ddd, J=10.5, 3.3, 1.8, 1H), 5.31 (dd, J=15.2, 9.6, 1H), 4.84 (dtd, J=12.5, 6.3, 4.5, 1H), 4.32 (p, J=4.7, 1H), 2.43 (s, 4H), 2.23 (ddt, J=14.3, 9.3, 7.1, 2H), 2.02 (dtd, J=10.1, 5.4, 5.0, 2.6, 1H), 1.97 (dddd, J=7.9, 5.4, 3.7, 1.6, 2H), 1.88-1.82 (m, 2H), 1.77-1.64 (m, 2H), 1.57-1.48 (m, 2H), 1.24 (d, J=6.3, 3H), 0.97-0.89 (m, 1H). $^{13}C$ NMR (150 MHz, Chloroform-d) δ=166.1, 165.9, 147.5, 143.6, 137.9, 136.5, 133.1, 130.9, 130.7, 130.4, 126.6, 126.5, 118.3, 118.3, 76.6, 72.4, 72.0, 49.6, 44.4, 43.2, 41.0, 34.1, 31.9, 26.7, 20.9, 19.8. ESI-MS m/z 425.54 $[M+H]^+$.

Compound 8c: $^1H$ NMR (600 MHz, Chloroform-d) δ=8.00 (dd, J=40.3, 15.9, 2H), 7.57 (t, J=7.2, 2H), 7.34 (ddd, J=15.7, 3.4, 1.0, 1H), 7.28 (tdd, J=7.2, 6.1, 1.3, 2H), 7.25-7.18 (m, 4H), 6.37 (ddd, J=37.0, 15.9, 1.0, 2H), 5.82-5.72 (m, 2H), 5.44 (ddd, J=10.3, 3.3, 1.9, 1H), 5.36-5.24 (m, 2H), 4.91-4.82 (m, 1H), 2.61-2.52 (m, 1H), 2.48-2.37 (m, 7H), 2.29-2.18 (m, 2H), 2.04 (tdd, J=13.3, 4.9, 2.4, 1H), 1.93-1.79 (m, 3H), 1.78-1.70 (m, 2H), 1.59-1.52 (m, 1H), 1.26 (d, J=6.0, 3H), 1.02-0.92 (m, 1H). $^{13}C$ NMR (150 MHz, Chloroform-d) δ=166.7, 166.0, 165.9, 147.4, 143.9, 142.7, 138.0, 137.8, 136.0, 133.4, 133.3, 131.3, 131.0, 131.0, 130.4, 130.2, 126.7, 126.5, 126.5, 126.5, 119.4, 118.6, 118.3, 76.5, 75.5, 72.0, 50.1, 44.3, 40.3, 38.7, 34.2, 32.0, 26.7, 20.9, 19.9, 19.9. ESI-MS m/z 569.71 $[M+H]^+$.

Example 9

7-O-((E)-3-(benzo[d][1,3]dioxa-5-yl)acrylic (Compound 9a), 4-O-((E)-3-(benzo[d][1,3]dioxa-5-yl) acrylic acid)acyl BFA (Compound 9b) and 4,7-O-bis((E)-3-(benzo[d][1,3]dioxa-5-yl)acrylic acid)acyl BFA (Compound 9c)

According to the preparation method of Example 1, white solids 9a, 9b and 9c were obtained in yields of 18%, 32% and 41%, respectively.

Structural characterization: Compound 9a: $^1H$ NMR (600 MHz, Chloroform-d) δ=7.58-7.52 (d, J=15.9, 1H), 7.39-7.34 (dd, J=15.7, 3.1, 1H), 7.04-7.02 (d, J=1.7, 1H), 7.02-6.98 (dd, J=8.0, 1.8, 1H), 6.82-6.78 (d, J=8.0, 1H), 6.26-6.19 (d, J=15.9, 1H), 6.02-5.98 (s, 2H), 5.95-5.90 (dd, J=15.6, 1.9, 1H), 5.76-5.69 (ddd, J=15.0, 10.3, 4.6, 1H), 5.28-5.22 (m, 2H), 4.90-4.82 (dqd, J=12.6, 6.3, 1.7, 1H), 4.18-4.12 (m, 1H), 2.46-2.38 (qd, J=9.1, 7.0, 1H), 2.38-2.32 (m, 1H), 2.31-2.25 (m, 1H), 2.04-1.99 (m, 2H), 1.96-1.83 (m, 4H), 1.76-1.71 (m, 1H), 1.66-1.64 (m, 1H), 1.57-1.49 (m, 1H), 1.27-1.25 (d, J=6.2, 3H), 0.98-0.91 (m, 1H). HRESIMS m/z 455.2059 $[M+H]^+$ (calcd. for $[C_{26}H_{31}O_7]^+$, 455.2064).

Compound 9b: $^1H$ NMR (600 MHz, Chloroform-d) δ=7.64-7.56 (d, J=15.8, 1H), 7.32-7.26 (dd, J=15.7, 3.3, 1H), 7.05-6.97 (m, 2H), 6.83-6.77 (d, J=7.9, 1H), 6.33-6.20 (d, J=15.8, 1H), 6.02-5.94 (s, 2H), 5.76-5.63 (m, 2H), 5.40-5.31 (m, 1H), 5.32-5.26 (dd, J=15.2, 9.6, 1H), 4.89-4.77 (m, 1H), 4.36-4.24 (m, 1H), 2.50-2.37 (m, 1H), 2.27-2.15 (m, 2H), 1.99-1.95 (d, J=8.6, 2H), 1.85-1.82 (s, 2H), 1.75-1.61 (m, 2H), 1.56-1.46 (m, 2H), 1.24-1.17 (d, J=6.2, 3H), 0.97-0.85 (m, 1H). HRESIMS m/z 455.2061 $[M+H]^+$ (calcd. for $[C_{26}H_{31}O_7]^+$, 455.2064).

Compound 9c: $^1H$ NMR (400 MHz, Chloroform-d) δ=7.67-7.59 (d, J=15.9, 1H), 7.59-7.52 (d, J=15.9, 1H), 7.37-7.28 (dd, J=15.7, 3.3, 1H), 7.06-6.98 (m, 4H), 6.84-6.78 (dd, J=8.0, 1.9, 2H), 6.33-6.26 (d, J=15.9, 1H), 6.26-6.20 (d, J=15.9, 1H), 6.05-5.97 (d, J=2.7, 4H), 5.82-5.70 (m, 2H), 5.46-5.37 (ddd, J=10.1, 3.4, 1.9, 1H), 5.31-5.25 (m, 2H), 4.91-4.80 (dqd, J=12.5, 6.2, 1.7, 1H), 2.60-2.46 (m, 1H), 2.45-2.31 (m, 1H), 2.29-2.13 (m, 2H), 2.09-2.00 (m, 1H), 1.90-1.68 (m, 5H), 1.61-1.47 (m, 1H), 1.27-1.23 (d, J=6.2, 3H), 1.03-0.90 (m, 1H). ESI-MS m/z 629.67 $[M+H]^+$.

Example 10

7-O-(4-dimethylaminocinnamic acid)acyl BFA (Compound 10a), 4-O-(4-dimethylaminocinnamic acid)acyl BFA (Compound 10b) and 4,7-O-bis(4-dimethylaminocinnamic acid)acyl BFA (Compound 10c)

According to the preparation method of Example 1, yellow solids 10a, 10b and 10c were obtained in yields of 20%, 45% and 30%, respectively.

Structural characterization: Compound 10a: $^1H$ NMR (600 MHz, $CDCl_3$) δ 7.61-7.55 (1H, d, J=15.8 Hz), 7.44-7.39 (2H, m), 7.40-7.34 (1H, dd, J=15.7, 3.1 Hz), 6.69-6.63 (2H, m), 6.21-6.15 (1H, d, J=15.8 Hz), 5.96-5.90 (1H, dd, J=15.7, 2.0 Hz), 5.78-5.67 (1H, m), 5.29-5.22 (2H, m), 4.89-4.82 (1H, dqd, J=11.0, 6.3, 1.8 Hz), 4.17-4.12 (1H, m), 3.03-3.00 (6H, s), 2.47-2.35 (1H, m), 2.38-2.28 (1H, m), 2.33-2.22 (1H, m), 2.04-2.01 (1H, m), 2.01-1.89 (1H, m), 1.91-1.81 (3H, m), 1.78-1.68 (1H, m), 1.69-1.64 (1H, m), 1.59-1.47 (1H, m), 1.27-1.25 (3H, d, J=6.2 Hz), 0.99-0.90 (1H, m). ESI-MS m/z 454.5 $[M+H]^+$.

Compound 10b: $^1H$ NMR (600 MHz, $CDCl_3$) δ 7.68-7.63 (1H, d, J=15.8 Hz), 7.44-7.40 (2H, m), 7.35-7.28 (1H, dd, J=15.7, 3.2 Hz), 6.68-6.63 (2H, m), 6.27-6.20 (1H, d, J=15.8 Hz), 5.79-5.74 (1H, dd, J=15.6, 1.9 Hz), 5.75-5.67 (1H, m), 5.40-5.35 (1H, ddd, J=10.5, 3.3, 1.9 Hz), 5.34-5.28 (1H, dd, J=15.1, 9.6 Hz), 4.87-4.80 (1H, dqd, J=12.5, 6.2, 1.7 Hz), 4.33-4.28 (1H, m), 3.04-2.98 (6H, s), 2.49-2.36 (1H, m), 2.26-2.17 (2H, m), 2.04-1.91 (2H, m), 1.86-1.81 (2H, m), 1.74-1.65 (2H, m), 1.59-1.46 (2H, m), 1.26-1.21 (3H, d, J=6.2 Hz), 0.97-0.87 (1H, m). ESI-MS m/z 454.5 $[M+H]^+$.

Compound 10c: $^1H$ NMR (600 MHz, $CDCl_3$) δ 7.69-7.55 (2H, dd, J=37.7, 15.8 Hz), 7.46-7.38 (4H, d, J=8.7 Hz), 7.36-7.30 (1H, dd, J=15.7, 3.3 Hz), 6.69-6.61 (4H, d, J=8.9 Hz), 6.29-6.11 (2H, dd, J=28.0, 15.8 Hz), 5.82-5.68 (2H, m), 5.43-5.37 (1H, ddd, J=10.3, 3.4, 1.9 Hz), 5.33-5.27 (1H, m), 5.27-5.22 (1H, m), 4.89-4.80 (1H, m), 3.02-3.00 (12H, d, J=2.4 Hz), 2.99-2.96 (1H, dd, J=8.3, 1.1 Hz), 2.57-2.48 (1H, dq, J=14.9, 7.5, 5.9 Hz), 2.42-2.33 (1H, ddd, J=14.9, 9.6, 5.5 Hz), 2.27-2.14 (2H, tq, J=19.1, 10.8, 8.8 Hz), 2.07-1.97 (1H, s), 1.90-1.64 (5H, m), 1.25-1.23 (3H, d, J=6.2 Hz), 1.01-0.91 (1H, m). ESI-MS m/z 627.7 $[M+H]^+$.

Example 11

7-O-(3,4,5-trimethoxycinnamic acid)acyl BFA (Compound 11a), 4-O-(3,4,5-trimethoxycinnamic acid)acyl BFA (Compound 11b) and 4,7-O-bis(3,4,5-trimethoxycinnamic acid)acyl BFA (Compound 11c)

According to the preparation method of Example 1, white solids 11a, 11b and 11c were obtained in yields of 22%, 30% and 41%, respectively.

Structural characterization: Compound 11a: $^1$H NMR (400 MHz, Chloroform-d) δ=7.61-7.52 (d, J=15.9, 1H), 7.42-7.33 (dd, J=15.7, 3.2, 1H), 6.78-6.73 (s, 2H), 6.36-6.26 (dd, J=15.9, 0.9, 1H), 5.98-5.89 (m, 1H), 5.80-5.67 (ddd, J=14.9, 10.1, 4.6, 1H), 5.32-5.21 (dd, J=15.2, 8.5, 2H), 4.94-4.82 (m, 1H), 4.21-4.12 (d, J=9.5, 1H), 3.91-3.87 (dd, J=5.3, 0.9, 9H), 2.50-2.26 (m, 3H), 2.09-1.80 (m, 5H), 1.79-1.47 (m, 3H), 1.28-1.26 (s, 3H), 1.02-0.91 (q, J=7.1, 1H). ESI-MS m/z 501.59 $[M+H]^+$.

Compound 11b: $^1$H NMR (400 MHz, Chloroform-d) δ=7.69-7.59 (d, J=15.9, 1H), 7.36-7.27 (dd, J=15.6, 3.2, 1H), 6.80-6.75 (s, 2H), 6.41-6.33 (d, J=15.9, 1H), 5.82-5.75 (dd, J=15.6, 1.8, 1H), 5.76-5.67 (m, 1H), 5.45-5.36 (ddd, J=10.5, 3.3, 1.9, 1H), 5.36-5.26 (dd, J=15.2, 9.5, 1H), 4.91-4.79 (m, 1H), 4.38-4.27 (m, 1H), 3.98-3.83 (d, J=6.0, 9H), 2.54-2.38 (m, 1H), 2.32-2.18 (m, 2H), 2.11-1.94 (m, 2H), 1.94-1.79 (m, 2H), 1.80-1.63 (m, 2H), 1.57-1.47 (m, 2H), 1.26-1.22 (d, J=6.3, 3H), 1.01-0.88 (m, 1H). ESI-MS m/z 501.59 $[M+H]^+$.

Compound 11c: ESI-MS m/z 721.81 $[M+H]^+$.

Example 12

7-O-(3-methoxy-4-phenoxycinnamic acid)acyl BFA (Compound 12a), 4-O-(3-methoxy-4-phenoxycinnamic acid)acyl BFA (Compound 12b) and 4,7-O-bis(3-methoxy-4-phenoxycinnamic acid)acyl BFA (Compound 12c)

According to the preparation method of Example 1, white oily solids 12a, 12b and 12c were obtained in yields of 20%, 30% and 40%, respectively.

Structural characterization: Compound 12a: ESI-MS m/z 533.63 $[M+H]^+$. Compound 12b: ESI-MS m/z 533.63 $[M+H]^+$. Compound 12c: $^1$H NMR (500 MHz, Chloroform-d) δ=7.68-7.62 (d, J=15.8, 1H), 7.61-7.55 (d, J=15.8, 1H), 7.46-7.30 (m, 10H), 7.10-7.02 (m, 4H), 6.90-6.85 (dd, J=8.3, 2.3, 2H), 6.36-6.30 (d, J=15.9, 1H), 6.29-6.24 (d, J=15.9, 1H), 5.83-5.71 (m, 2H), 5.47-5.40 (dt, J=10.3, 2.6, 1H), 5.34-5.24 (m, 2H), 5.22-5.16 (s, 1H), 4.92-4.82 (m, 1H), 3.96-3.89 (d, J=3.5, 6H), 2.60-2.49 (qd, J=9.3, 6.6, 1H), 2.45-2.35 (ddd, J=14.9, 9.7, 5.5, 1H), 2.29-2.14 (dq, J=17.5, 7.9, 2H), 2.09-1.97 (m, 1H), 1.91-1.68 (m, 5H), 1.59-1.54 (ddd, J=15.1, 7.2, 3.1, 1H), 1.27-1.23 (d, J=6.2, 3H), 1.02-0.92 (td, J=13.4, 5.7, 1H). ESI-MS m/z 785.90 $[M+H]^+$

Example 13

7-O-(4-trifluoromethylcinnamic acid)acyl BFA (Compound 13a), 4-O-(4-trifluoromethylcinnamic acid)acyl BFA (Compound 13b) and 4,7-O-bis(4-trifluoromethyl cinnamic acid)acyl BFA (Compound 13c)

According to the preparation method of Example 1, white solids 13a, 13b and 13c were obtained in yields of 20%, 35% and 42%, respectively.

Structural characterization: Compound 13a: $^1$H NMR (400 MHz, Chloroform-d) δ=7.70-7.58 (m, 5H), 7.41-7.31 (dd, J=15.7, 3.1, 1H), 6.52-6.42 (d, J=16.0, 1H), 5.97-5.90 (dd, J=15.7, 1.9, 1H), 5.80-5.67 (m, 1H), 5.33-5.20 (m, 2H), 4.93-4.80 (m, 1H), 4.20-4.12 (m, 1H), 2.49-2.26 (m, 3H), 2.02-1.84 (m, 5H), 1.76-1.66 (m, 2H), 1.57-1.48 (m, 1H), 1.28-1.25 (d, J=6.3, 3H), 1.00-0.91 (m, 1H). ESI-MS m/z 479.51 $[M+H]^+$.

Compound 13b: $^1$H NMR (400 MHz, Chloroform-d) δ=7.77-7.68 (d, J=16.1, 1H), 7.69-7.58 (d, J=2.3, 4H), 7.34-7.26 (dd, J=15.7, 3.3, 1H), 6.58-6.47 (d, J=16.1, 1H), 5.81-5.63 (m, 2H), 5.43-5.35 (ddd, J=10.5, 3.4, 1.9, 1H), 5.35-5.26 (dd, J=15.2, 9.5, 1H), 4.90-4.78 (dqd, J=12.5, 6.3, 1.7, 1H), 4.36-4.27 (m, 1H), 2.51-2.38 (m, 1H), 2.31-2.17 (m, 2H), 2.02-1.96 (m, 2H), 1.91-1.78 (m, 2H), 1.75-1.63 (m, 2H), 1.59-1.45 (m, 2H), 1.26-1.19 (d, J=6.2, 3H), 0.98-0.85 (m, 1H). ESI-MS m/z 479.51 $[M+H]^+$.

Compound 13c: $^1$H NMR (400 MHz, Chloroform-d) δ=7.80-7.71 (d, J=16.1, 1H), 7.70-7.58 (m, 9H), 7.37-7.28 (dd, J=15.6, 3.4, 1H), 6.61-6.52 (d, J=16.0, 1H), 6.51-6.45 (d, J=16.1, 1H), 5.86-5.71 (m, 2H), 5.49-5.40 (ddd, J=10.1, 3.4, 1.8, 1H), 5.36-5.24 (m, 2H), 4.94-4.81 (dqd, J=12.5, 6.2, 1.7, 1H), 2.64-2.50 (m, 1H), 2.49-2.36 (m, 1H), 2.32-2.16 (m, 2H), 2.11-1.98 (m, 1H), 1.95-1.70 (m, 5H), 1.62-1.48 (m, 1H), 1.29-1.23 (d, J=6.3, 3H), 1.04-0.90 (m, 1H). ESI-MS m/z 677.65 $[M+H]^+$.

Example 14

7-O-(3-(pyridine-4-yl)acrylic acid)acyl BFA (Compound 14a), 4-O-(3-pyridine-4-yl)acrylic acid)acyl BFA (Compound 14b) and 4,7-O-bis(3-pyridine-4-yl)acrylic acid)acyl BFA (Compound 14c)

According to the preparation method of Example 1, white solids 14a, 14b and 14c were obtained in yields of 20%, 40% and 35%, respectively.

Compound 14a: $^1$H NMR (400 MHz, $CDCl_3$) δ 8.69-8.61 (2H, m), 7.61-7.53 (1H, d, J=16.0 Hz), 7.41-7.32 (3H, m), 6.60-6.52 (1H, d, J=16.0 Hz), 5.98-5.88 (1H, dd, J=15.7, 1.9 Hz), 5.80-5.68 (1H, m), 5.34-5.19 (2H, m), 4.94-4.81 (1H, m), 4.21-4.11 (1H, d, J=9.6 Hz), 2.50-2.27 (3H, m), 2.03-1.83 (5H, m), 1.79-1.66 (2H, m), 1.57-1.48 (1H, m), 1.28-1.26 (3H, d, J=6.3 Hz), 1.01-0.90 (1H, m). ESI-MS m/z 412.2 $[M+H]^+$.

Compound 14b: $^1$H NMR (400 MHz, $CDCl_3$) δ 8.73-8.60 (2H, s), 7.67-7.59 (1H, d, J=16.0 Hz), 7.41-7.36 (2H, d, J=5.5 Hz), 7.32-7.26 (1H, dd, J=15.7, 3.3 Hz), 6.68-6.57 (1H, d, J=16.0 Hz), 5.79-5.66 (2H, dd, J=15.7, 1.8 Hz), 5.44-5.37 (1H, ddd, J=10.5, 3.3, 1.8 Hz), 5.36-5.27 (1H, dd, J=15.2, 9.5 Hz), 4.91-4.79 (1H, m), 4.38-4.30 (1H, m), 2.53-2.40 (1H, m), 2.32-2.19 (2H, m), 2.07-1.93 (2H, m), 1.91-1.80 (2H, m), 1.78-1.73 (1H, m), 1.69-1.62 (1H, m), 1.60-1.47 (2H, m), 1.29-1.19 (3H, d, J=6.2 Hz), 1.02-0.86 (1H, m). ESI-MS m/z 412.2 $[M+H]^+$. Compound 14c: ESI-MS m/z 543.6 $[M+H]^+$.

Example 15

7-O-(3-(pyridine-2-yl)acrylic acid)acyl BFA (Compound 15a), 4-O-(3-pyridine-2-yl)acrylic acid)acyl BFA (Compound 15b) and 4,7-O-bis(3-pyridine-2-yl)acrylic acid)acyl BFA (Compound 15c)

According to the preparation method of Example 1, white solids 15a, 15b and 15c were obtained in yields of 23%, 41% and 35%, respectively.

Compound 15a: $^1$H NMR (400 MHz, $CDCl_3$) δ 8.69-8.56 (1H, m), 7.74-7.69 (1H, td, J=7.7, 1.8 Hz), 7.68-7.62 (1H, d, J=15.7 Hz), 7.46-7.41 (1H, d, J=7.8 Hz), 7.40-7.33 (1H, dd, J=15.7, 3.1 Hz), 7.29-7.26 (1H, m), 6.95-6.83 (1H, d, J=15.7 Hz), 5.98-5.87 (1H, dd, J=15.7, 1.9 Hz), 5.79-5.65 (1H, m), 5.34-5.21 (2H, m), 4.92-4.80 (1H, m), 4.19-4.11 (1H, d, J=9.4 Hz), 2.51-2.25 (3H, m), 2.03-1.83 (5H, m), 1.76-1.63 (2H, m), 1.58-1.48 (1H, m), 1.28-1.23 (3H, d, J=6.3 Hz), 1.01-0.88 (1H, m). ESI-MS m/z 412.2 $[M+H]^+$.

Compound 15b: $^1$H NMR (400 MHz, $CDCl_3$) δ 8.70-8.62 (1H, m), 7.77-7.67 (2H, m), 7.47-7.40 (1H, dt, J=7.8, 1.1 Hz), 7.33-7.26 (2H, m), 7.01-6.92 (1H, d, J=15.7 Hz), 5.83-5.64 (2H, m), 5.43-5.36 (1H, ddd, J=10.5, 3.4, 1.9 Hz), 5.36-5.27 (1H, dd, J=15.2, 9.5 Hz), 4.90-4.78 (1H, m), 4.36-4.28 (1H, m), 2.53-2.37 (1H, m), 2.32-2.14 (2H, m), 2.06-1.93 (2H, m), 1.91-1.79 (2H, m), 1.73-1.65 (2H, m), 1.58-1.48 (2H, m), 1.27-1.20 (3H, d, J=6.3 Hz), 1.01-0.87 (1H, m). ESI-MS m/z 412.2 $[M+H]^+$. Compound 15c: ESI-MS m/z 543.6 $[M+H]^+$.

Example 16

7-O-(3-(pyridine-3-yl)acrylic acid)acyl BFA (Compound 16a), 4-O-(3-pyridine-3-yl)acrylic acid)acyl BFA (Compound 16b) and 4,7-O-bis(3-pyridine-3-yl)acrylic acid)acyl BFA (Compound 16c)

According to the preparation method of Example 1, white solids 16a, 16b and 16c were obtained in yields of 20%, 40% and 35%, respectively.

Compound 16a: $^1$H NMR (400 MHz, $CDCl_3$) δ 8.82-8.72 (1H, s), 8.68-8.56 (1H, d, J=4.2 Hz), 7.91-7.83 (1H, dt, J=8.0, 2.0 Hz), 7.72-7.62 (1H, d, J=16.1 Hz), 7.43-7.32 (2H, m), 6.55-6.46 (1H, d, J=16.1 Hz), 6.01-5.92 (1H, dd, J=15.7, 1.9 Hz), 5.82-5.70 (1H, m), 5.35-5.24 (2H, m), 4.95-4.83 (1H, m), 4.26-4.13 (1H, dt, J=9.4, 2.6 Hz), 2.52-2.28 (3H, m), 2.09-2.03 (1H, m), 2.01-1.91 (2H, m), 1.89-1.84 (1H, m), 1.77-1.69 (3H, m), 1.63-1.49 (1H, m), 1.31-1.27 (3H, d, J=6.3 Hz), 1.05-0.91 (1H, m). ESI-MS m/z 412.2 $[M+H]^+$.

Compound 16b: $^1$H NMR (400 MHz, $CDCl_3$) δ 8.79-8.70 (1H, s), 8.64-8.56 (1H, d, J=4.9 Hz), 7.90-7.81 (1H, dt, J=8.0, 2.0 Hz), 7.76-7.63 (1H, d, J=16.1 Hz), 7.37-7.32 (1H, dd, J=8.0, 4.8 Hz), 7.32-7.26 (1H, dd, J=15.7, 3.3 Hz), 6.58-6.49 (1H, d, J=16.1 Hz), 5.79-5.64 (2H, m), 5.45-5.36 (1H, dt, J=10.6, 2.6 Hz), 5.36-5.26 (1H, dd, J=15.5, 9.8 Hz), 4.90-4.78 (1H, m), 4.37-4.28 (1H, m), 2.51-2.38 (1H, m), 2.32-2.17 (2H, m), 2.01-1.96 (2H, m), 1.90-1.80 (2H, m), 1.79-1.61 (2H, m), 1.59-1.46 (2H, m), 1.28-1.19 (3H, d, J=6.2 Hz), 1.00-0.85 (1H, m). ESI-MS m/z 412.2 $[M+H]^+$. Compound 16c: ESI-MS m/z 543.6 $[M+H]^+$.

Example 17

7-O-(3-(quinoline-3-yl)acrylic acid)acyl BFA (Compound 17a), 4-O-(3-quinoline-3-yl)acrylic acid)acyl BFA (Compound 17b) and 4,7-O-bis(3-quinoline-3-yl)acrylic acid)acyl BFA (Compound 17c)

According to the preparation method of Example 1, white solids 17a, 17b and 17c were obtained in yields of 20%, 37% and 35%, respectively.

Compound 17a: ESI-MS m/z 462.5 $[M+H]^+$. Compound 17b: ESI-MS m/z 462.5 $[M+H]^+$. 17c: ESI-MS m/z 643.7 $[M+H]^+$.

Example 18

7-O-(3-(isoquinoline-4-yl)acrylic acid)acyl BFA (Compound 18a), 4-O-(3-isoquinoline-4-yl)acrylic acid)acyl BFA (Compound 18b) and 4,7-O-bis(3-isoquinoline-4-yl)acrylic acid)acyl BFA (Compound 18c)

According to the preparation method of example 1, white solid 18a, 18b and 18c were obtained in yields of 20%, 40% and 35%, respectively.

Compound 18a: ESI-MS m/z 462.5 $[M+H]^+$. Compound 18b: ESI-MS m/z 462.5 $[M+H]^+$. 18c: ESI-MS m/z 643.7 $[M+H]^+$.

Example 19

7-O-(3-(4-aminopyridine-3-yl)acrylic acid)acyl BFA (Compound 19a), 4-O-(3-(4-aminopyridine-3-yl) acrylic acid)acyl BFA (Compound 19b) and 4,7-O-bis(3-(4-aminopyridine-3-yl)acrylic acid)acyl BFA (Compound 19c)

According to the preparation method of example 1, white solid 19a, 19b and 19c were obtained in yields of 20%, 44% and 35%, respectively.

19a: ESI-MS m/z 427.5 $[M+H]^+$. 19b: ESI-MS m/z 427.5 $[M+H]^+$. 19c: ESI-MS m/z 573.6 $[M+H]^+$.

Example 20 Solubility Test

Objective: To compare the difference in solubility of the compounds disclosed herein with BFA.

Methods: Excess BFA and the compounds disclosed herein were added to 10 mL of three solvents, methanol, acetone and 5% DMSO+95% $H_2O$, respectively, and shaken on a shaker at 37° C. at 100 r/min for 24 h. After 24 h, the samples were centrifuged at 15,000 r/min for 15 min to remove the undissolved compounds. The supernatant was filtered using a 0.45 μm membrane filter. The supernatant was appropriately diluted with methanol and contents of the compounds were determined by HPLC method to calculate the solubility.

Results

TABLE 1

Solubility of the compounds disclosed herein (x ± s, n = 3)

| Compounds | Solubility ($mg \cdot mL^{-1}$) Methanol | Acetone | 5% DMSO + 95% $H_2O$ |
|---|---|---|---|
| BFA | 3.13 ± 1.24 | 3.13 ± 1.24 | 0.085 ± 0.03 |
| Compound 1a | 21.34 ± 1.52 | 21.89 ± 1.53 | 0.33 ± 0.13 |
| Compound 1b | 21.13 ± 1.32 | 21.02 ± 1.42 | 0.32 ± 0.05 |
| Compound 1c | 12.23 ± 1.59 | 12.14 ± 0.91 | 0.20 ± 0.91 |
| Compound 10a | 25.28 ± 4.35 | 25.61 ± 1.74 | 0.75 ± 1.60 |
| Compound 10b | 24.17 ± 1.22 | 23.18 ± 1.32 | 0.72 ± 0.13 |
| Compound 10c | 13.34 ± 0.91 | 12.54 ± 0.92 | 0.44 ± 0.08 |
| Compound 16a | 30.57 ± 1.02 | 31.60 ± 0.72 | 0.76 ± 0.23 |
| Compound 16b | 29.88 ± 1.52 | 30.28 ± 0.52 | 0.73 ± 0.13 |
| Compound 16c | 20.45 ± 0.52 | 21.40 ± 0.77 | 0.45 ± 0.28 |
| Compound 17a | 32.55 ± 1.12 | 33.20 ± 0.72 | 0.76 ± 0.23 |
| Compound 17b | 31.88 ± 1.52 | 32.28 ± 0.52 | 0.73 ± 0.13 |
| Compound 17c | 20.45 ± 0.52 | 20.40 ± 0.77 | 0.45 ± 0.28 |
| Compound A | 9.48 ± 1.01 | 9.46 ± 1.26 | 0.22 ± 0.13 |
| Compound B | 9.41 ± 1.51 | 9.48 ± 3.23 | 0.22 ± 0.16 |
| Compound C | 5.30 ± 2.51 | 5.36 ± 3.13 | 0.10 ± 0.23 |

Note: The present disclosure tests, in parallel, the compounds, in which Z is benzene ring, $R_3$ is H, in the preparation process for control, namely compound A ( 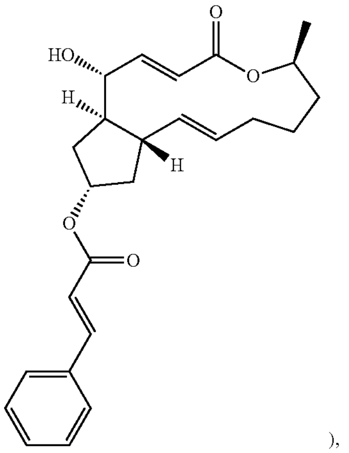 ), compound B ( 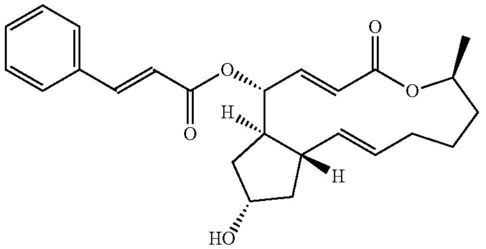 ), compound C ( 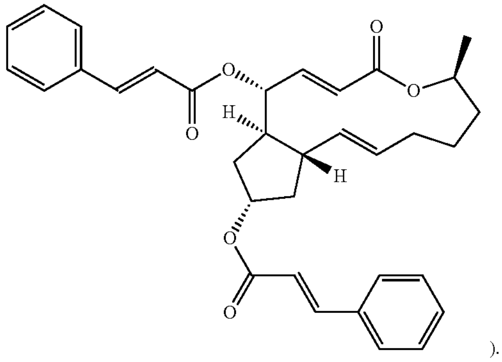 ).

The results showed that the compounds disclosed herein exhibited higher solubility in the three solvents, methanol, acetone and 5% DMSO+95% $H_2O$, than BFA as well as the compounds, in which Z is benzene ring and $R_3$ is H, which showed significant advantages.

Example 21: Bioactivity Test

Test 1 Cell Proliferation Assay

1) Principle

CCK-8 method: The CCK-8 method is a highly sensitive, non-radioactive colorimetric assay for the determination of the number of viable cells in cell proliferation or cytotoxicity assays. The orange formazan dye produced by the bioreduction of CCK-8 by intracellular dehydrogenase is soluble in the cell culture medium, and the amount of formazan dye produced is proportional to the number of living cells. The kit used in this method is the tetrazolium salt-WST-8 (2-(2-methoxy-4-nitrophenyl)-3-(4-nitrophenyl)-5-(2,4-disulfophenyl)-2H-tetrazolium monosodium salt) developed by Dojindo Chemical Research Institute (Dojindo), which is capable of being reduced to a water-soluble formazan dye in the presence of the electronic carrier 1-Methoxy PMS.

2) Cell Culture and Preparation of Test Compounds

Human cervical cancer Hela cells, pancreatic cancer PANC-1cells, esophageal cancer Eca-109 cells, human leukemia K562 cells, human lung cancer A549 cells, human liver cancer HepG2 cells, human gastric cancer MKN-45 cells, human breast cancer MCF7 cells were cultured in DMEM medium containing 10% FBS (fetal bovine serum), 100 U/mL penicillin and 100 μg/ml streptomycin. Hepatocellular carcinoma cells Bel-7402 were cultured in RPMI-1640 medium containing 10% FBS (fetal bovine serum), 100 U/ml penicillin and 100 μg/ml streptomycin. All cells were placed in a cell culture incubator at 37° C. with 5% $CO_2$. Cells fluid was changed every 3-5 days, and after 80% cell fusion, trypsin digestion and passaging were performed to keep the cells in good logarithmic growth phase.

All the samples to be tested were dissolved in DMSO.

3) Assay Method

Cells in logarithmic growth phase were inoculated in 96-well plates with 5000 cells/well respectively, and after 24 h of incubation, samples were added (final concentrations as shown in the table), and biplicate wells were set up for each sample. The amount of solvent of DMSO was not higher than 2%. After 72 h, 10 μL of CCK-8 solution was added to each well and incubated for 1.5~3 h at 37° C. The OD value at 450 nm was measured on an plate reader.

$$\text{Inhibition rate }(\%)=(1-[(OD_{450}\text{ dosed well}-OD_{450}\text{ blank well})/(OD_{450}\text{ control well}-OD_{450}\text{ blank well})])\times 100\%$$

The fitted $IC_{50}$ values were calculated using the log (inhibitor) vs. response—Variable slop analysis method in GraphPad Prism software.

4) Results:

TABLE 2

Effect of compounds disclosed herein on tumor cell proliferation

| Compounds | $IC_{50}$ (μM) HepG2 | Hela | Eca-109 | K562 | PANC-1 | MKN-45 | MCF7 | A549 |
|---|---|---|---|---|---|---|---|---|
| BFA | B | B | B | B | A | B | A | B |
| 1a | B | C | C | B | B | B | B | B |
| 1b | B | B | B | B | B | B | B | B |
| 1c | C | C | C | B | C | B | C | C |
| 2a | B | C | C | B | B | B | B | B |
| 2b | B | C | C | B | B | B | B | B |
| 2c | C | C | C | B | C | B | C | C |
| 3a | B | C | C | B | B | B | B | B |
| 3b | B | B | C | B | B | B | B | B |
| 3c | C | C | C | C | B | C | C | B |
| 4a | B | B | B | B | B | B | B | B |
| 4b | B | B | B | B | B | B | B | B |
| 4c | C | B | C | C | C | B | C | B |
| 5a | B | B | C | B | B | B | B | B |
| 5b | B | B | B | B | B | B | B | B |
| 5c | C | B | C | C | C | B | C | B |
| 6a | C | C | B | B | B | B | B | B |
| 6b | B | B | B | B | B | B | B | B |
| 6c | C | C | B | C | C | B | C | C |
| 7a | C | C | C | C | B | B | C | B |
| 7b | B | C | B | C | B | B | B | B |
| 7c | C | C | B | C | C | B | C | C |
| 8a | C | C | B | C | B | B | B | B |
| 8b | B | C | B | C | B | B | B | B |
| 8c | C | C | B | C | C | B | C | C |
| 9a | C | C | C | B | B | B | B | B |
| 9b | C | C | C | B | B | B | B | B |
| 9c | C | C | C | B | C | B | C | C |
| 10a | C | C | C | B | C | B | B | B |
| 10b | B | B | C | B | B | B | B | B |
| 10c | C | C | C | B | C | B | C | B |
| 11a | B | C | C | B | B | B | B | B |
| 11b | B | C | C | B | B | B | B | B |
| 11c | C | C | C | B | C | C | C | B |
| 13a | B | B | B | B | B | B | B | B |
| 13b | B | B | B | B | B | B | B | B |
| 13c | C | C | C | B | C | C | C | B |
| 14a | A | B | C | B | A | B | B | B |
| 14b | A | B | C | B | A | B | B | B |
| 14c | B | C | C | B | C | B | C | B |
| 15a | A | B | C | B | A | B | B | B |
| 15b | A | B | B | B | A | B | B | B |
| 15c | B | C | C | B | B | C | B | B |
| 16a | A | B | B | B | A | B | B | B |
| 16b | A | B | B | B | A | B | B | B |
| 160 | B | C | C | B | B | C | C | B |
| 17a | A | B | B | B | A | B | B | B |
| 17b | A | B | B | B | A | B | B | B |
| 17c | B | C | C | B | B | C | B | C |
| Compound A | C | C | C | B | B | C | B | C |
| Compound B | C | C | C | B | B | C | B | C |

TABLE 2-continued

Effect of compounds disclosed herein on tumor cell proliferation

| Compounds | $IC_{50}$ (μM) HepG2 | Hela | Eca-109 | K562 | PANC-1 | MKN-45 | MCF7 | A549 |
|---|---|---|---|---|---|---|---|---|
| Compound C | C | C | C | C | C | C | C | C |
| Adriamycin | D | B | B | C | A | B | C | B |

Note:
"A" represents an $IC_{50}$ value less than 0.1 μM; "B" represents an $IC_{50}$ value in the range of 0.1-1.0 μM; "C" represents an $IC_{50}$ value in the range of 1.0-10 μM and "D" represents an $IC_{50}$ value higher than 10 μM.. In addition, compounds A, B, and C disclosed herein were tested the effects on the proliferation of tumor cells in parallel.

In the screening of in vitro cellular assay, the compounds disclosed herein exhibited high cytotoxic activity against multiple cancer cell lines, somewhat comparable to the positive drug adriamycin, better than compounds A, B, and C. Some of the compounds also exhibited good selectivity. Thus, the compounds disclosed herein have better potential application prospect in tumor proliferation inhibiting activity.

Test 2 Toxicity Test

Objective: Observation of toxic effects of compounds after intraperitoneally administration (ip.) to mice

Materials

1) Agents: Compounds disclosed herein were formulated to a suitable concentration.

2) Animals: Kunming breed mice, weight 18-22 g, male. Provided by Jinan Pengyue Laboratory Animal Breeding Co., Ltd. Animal license number: SCXK (Shandong 20140007)

Method: Kunming breed mice, were randomly grouped by weight, 6 mice per group, namely normal control group, BFA high and low dose groups (100 mg/kg and 50 mg/kg, respectively), and high and low dose groups of some compounds disclosed herein (BFA effective amount conversion). After a single administration, the animals were observed for behavior, mental status, feeding, drinking and other status responses and mortality. After 14 d of continuous administration, all the animals were weighed, and the animals were executed to observe whether there were any abnormalities in the organs.

Results a) Death occurred on the 12th day after administration in the high-dose group of BFA and occurred on the 14th day after administration in the low-dose group of BFA.

b) The animals were in good mental condition after the administration of high and low doses of Compounds 1a, 1b, 1c, 10a, 10b, 10c, 16a, 16b and 16c herein with no deaths. During administration, the fur of mice treated with the compounds disclosed herein was smoother than that of the mice treated with BFA. The results of anatomy on the 14 th day showed that there was no significant abnormality in all organs.

c) The weights of the animals in the administered group were slightly lower than those of the normal control group, but there was no significant difference by statistical comparison.

The results have shown that the compounds disclosed herein possess a significant reduction in toxicity after administration to mice compared to BFA, exhibiting a large degree of toxicity reduction.

Finally, it is important to note that there are other ways to implement the present disclosure. Accordingly, the embodiments herein are to be illustrated as examples, but are not limited to what is described in the present disclosure. It may be also an amendment made in the scope of this disclosure or an equivalent addition to the claims. All publications or patents cited herein will be used as references.

The invention claimed is:

1. An ester derivative of brefeldin A, wherein the ester derivative of brefeldin A is a compound represented by Formula (I), or a stereoisomer, a tautomer, a solvate, or a pharmaceutical acceptable salt of the compound represented by Formula (I), (I)

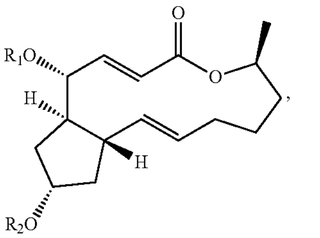

wherein $R_1$ and $R_2$ are each independently H or

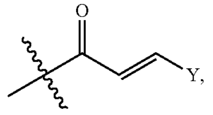

$R_1$ and $R_2$ are not H simultaneously; Y is selected from the group consisting of benzene ring having at least one substituent, pyridine ring optionally having a substituent, quinoline ring optionally having a substituent and isoquinoline ring optionally having a substituent;

when Y is benzene ring, the at least one substituent is optionally fused to the benzene ring, and the at least one substituent is selected from

| | | |
|---|---|---|
| F | Cl | Br |
| OH | CN | $CF_3$ |
| $NH_2$ | COOH | $NHOCH_3$ |
| $COOC_2H_5$ | $NHOC_2H_5$ | $CONH_2$ |
| $CH(CH_3)OH$ | $C(CH_3)_3$ | $CH_2Br$ |
| 2,3-2OH | 2,4-2OH | 2,5-2OH |
| 2,3,4-3OH | 2,3,5-3OH | 2,3,6-3OH |
| 3,4,5-3OH | 3,4,6-3OH | 3,5,6-3OH |
| 2,3-2F | 2,3-2Cl | 2,3-2Br |
| 2,4-2F | 2,4-2Cl | 2,4-2Br |
| 2,5-2F | 2,5-2Cl | 2,5-2Br |
| 2,6-2F | 2,6-2Cl | 2,6-2Br |
| 3,4-2F | 3,4-2Cl | 3,4-2Br |
| 3,5-2F | 3,5-2Cl | 3,5-2Br |
| 2,3,4-3F | 2,3,4-3Cl | 2,3,4-3Br |
| 2,3,5-3F | 2,3,5-3Cl | 2,3,5-3Br |
| 2,3,6-3F | 2,3,6-3Cl | 2,3,6-3Br |
| 2,4,5-3F | 2,4,5-3Cl | 2,4,5-3Br |
| 2,4,6-3F | 2,4,6-3Cl | 2,4,6-3Br |
| 2,5,6-3F | 2,5,6-3Cl | 2,5,6-3Br |
| 3,4,5-3F | 3,4,5-3Cl | 3,4,5-3Br |

-continued

| | | |
|---|---|---|
| 3,4,6-3F | 3,4,6-3Cl | 3,4,6-3Br |
| 3,5,6-3F | 3,5,6-3Cl | 3,5,6-3Br |
| 2,3,4,5-4F | 2,3,4,5-4Cl | 2,3,4,5-4Br |
| 2,3,4,6-4F | 2,3,4,6-4Cl | 2,3,4,6-4 Br |
| 2,3,4,5,6-5F | 2,3,4,5,6-5Cl | 2,3,4,5,6-5Br |
| 2,3-$2CF_3$ | 2,3,4-$3CF_3$ | 3,4,5-$3CF_3$ |
| 2,4-$2CF_3$ | 2,3,5-$3CF_3$ | 3,4,6-$3CF_3$ |
| 2,5-$2CF_3$ | 2,3,6-$3CF_3$ | 3,5,6-$3CF_3$ |
| 2,6-$2CF_3$ | 2,4,5-$3CF_3$ | 2,3,4,5-$4CF_3$ |
| 3,4-$2CF_3$ | 2,4,6-$3CF_3$ | 2,3,4,6-4 $CF_3$ |
| 3,5-$2CF_3$ | 2,5,6-$3CF_3$ | 2,3,4,5,6-5 $CF_3$ |
| I | $CH_3$ | $OCH_3$ |
| $OCF_3$ | $NO_2$ | $SO_2CH_3$ |
| $COOCH_3$ | $N(CH_3)_2$ | $C_2H_5$ |
| $CONHCH_3$ | $CON(CH_3)_2$ | $CH_2CH_2OH$ |
| | 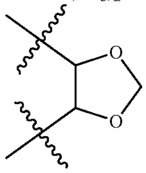 | 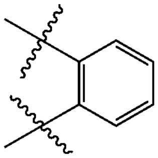 [SMILES: *c1ccccc1*] |
| 2,6-2OH | 3,4-2OH | 3,5-2OH |
| 2,4,5-3OH | 2,4,6-3OH | 2,5,6-3OH |
| 2,3,4,5-4OH | 2,3,4,6-4OH | 2,3,4,5,6-5OH |
| 2,3-2I | 2,3-$2CH_3$ | 2,3-$2OCH_3$ |
| 2,4-2I | 2,4-$2CH_3$ | 2,4-$2OCH_3$ |
| 2,5-2I | 2,5-$2CH_3$ | 2,5-$2OCH_3$ |
| 2,6-2I | 2,6-$2CH_3$ | 2,6-$2OCH_3$ |
| 3,4-2I | 3,4-$2CH_3$ | 3,4-$2OCH_3$ |
| 3,5-2I | 3,5-$2CH_3$ | 3,5-$2OCH_3$ |
| 2,3,4-3I | 2,3,4-$3CH_3$ | 2,3,4-$3OCH_3$ |
| 2,3,5-3I | 2,3,5-$3CH_3$ | 2,3,5-$3OCH_3$ |
| 2,3,6-3I | 2,3,6-$3CH_3$ | 2,3,6-$3OCH_3$ |
| 2,4,5-3I | 2,4,5-$3CH_3$ | 2,4,5-$3OCH_3$ |
| 2,4,6-3I | 2,4,6-$3CH_3$ | 2,4,6-$3OCH_3$ |
| 2,5,6-3I | 2,5,6-$3CH_3$ | 2,5,6-$3OCH_3$ |
| 3,4,5-3I | 3,4,5-$3CH_3$ | 3,4,5-$3OCH_3$ |
| 3,4,6-3I | 3,4,6-$3CH_3$ | 3,4,6-$3OCH_3$ |
| 3,5,6-3I | 3,5,6-$3CH_3$ | 3,5,6-$3OCH_3$ |
| 2,3,4,5-4I | 2,3,4,5-$4CH_3$ | 2,3,4,5-$4OCH_3$ |
| 2,3,4,6-4I | 2,3,4,6-4 $CH_3$ | 2,3,4,6-4 $OCH_3$ |
| 2,3,4,5,6-5I | 2,3,4,5,6-5 $CH_3$ | 2,3,4,5,6-5 $OCH_3$ |
| 2,3-$2OCF_3$ | 2,3,4-$3OCF_3$ | 3,4,5-$3OCF_3$ |
| 2,4-$2OCF_3$ | 2,3,5-$3OCF_3$ | 3,4,6-$3OCF_3$ |
| 2,5-$2OCF_3$ | 2,3,6-$3OCF_3$ | 3,5,6-$3OCF_3$ |
| 2,6-$2OCF_3$ | 2,4,5-$3OCF_3$ | 2,3,4,5-4 $OCF_3$ |
| 3,4-$2OCF_3$ | 2,4,6-$3OCF_3$ | 2,3,4,6-4 $OCF_3$ |
| 3,5-$2OCF_3$ | 2,5,6-$3OCF_3$ | 2,3,4,5,6-5 $OCF_3$. |

when Y is pyridine ring optionally having a substituent, quinoline ring optionally having a substituent or isoquinoline ring optionally having a substituent, the substituent is selected from:

| | | |
|---|---|---|
| F | Cl | Br |
| I | $CH_3$ | $OCH_3$ |
| OH | CN | $CF_3$ |
| $OCF_3$ | $NO_2$ | $SO_2CH_3$ |
| $NH_2$ | COOH | $NHOCH_3$ |
| $COOCH_3$ | $N(CH_3)_2$ | $C_2H_5$ |
| $COOC_2H_5$ | $NHOC_2H_5$ | $CONH_2$ |
| $CONHCH_3$ | $CON(CH_3)_2$ | $CH_2CH_2OH$ |
| $CH(CH_3)OH$ | $C(CH_3)_3$ | $CH_2Br$ |

2. The ester derivative of brefeldin A according to claim 1, wherein the stereoisomer of the compound represented by Formula (I) comprises a geometric isomer of the compound represented by Formula (I).

3. The ester derivative of brefeldin A according to claim 1, wherein the solvate of the compound represented by Formula (I) comprises a hydrate of the compound represented by Formula (I).

4. A pharmaceutical composition, comprising the ester derivative of brefeldin A according to claim 1.

5. The pharmaceutical composition according to claim 4, wherein the pharmaceutical composition further comprises a pharmaceutically acceptable excipient, a carrier, an adjuvant, a solvent or a combination thereof.

6. The pharmaceutical composition according to claim 5, wherein the excipient is selected from a diluent, a filler, a binder, a disintegrant, a lubricant, a glidant, a granulating agent, a coating agent, a wetting agent, a solvent, a co-solvent, a suspending agent, a emulsifier, a sweetener, a corrigent, a taste masking agent, a colorant, an anti-caking agent, a humectant, a chelating agent, a plasticizer, a tackifier, an antioxidant, a preservative, a stabilizer, a surfactant or a buffer.

7. The pharmaceutical composition according to claim 5, wherein the carrier is selected from a disintegrant, a controlled-release polymer, a lubricant, a diluent or a colorant.

8. A method for treatment of hyperproliferative diseases in mammals, comprising administering an effective amount of the ester derivative of brefeldin A according to claim 1.

9. The method according to claim 8, wherein the mammals comprise humans.

10. The method according to claim 8, wherein the hyperproliferative diseases are selected from the group consisting of liver cancer, leukemia, breast cancer, colon adenocarcinoma, gastric cancer, lung cancer, Bart's esophageal cancer, cervical cancer, pancreatic cancer, endometrial cancer, bone cancer, lymphoma, kidney cancer, brain cancer, nerve cancer, nasopharyngeal cancer, oral cancer and colorectal cancer.

* * * * *